US012715906B2

(12) United States Patent
Mueller et al.

(10) Patent No.: US 12,715,906 B2
(45) Date of Patent: Aug. 25, 2026

(54) SINGLE CHAIN VH AND HEAVY CHAIN ANTIBODIES

(71) Applicant: TRIANNI, INC., Wilmington, DE (US)

(72) Inventors: Werner Mueller, Cologne (DE); Matthias Wabl, San Francisco, CA (US)

(73) Assignee: TRIANNI, INC., San Francisco, CA (US)

( * ) Notice: Subject to any disclaimer, the term of this patent is extended or adjusted under 35 U.S.C. 154(b) by 1099 days.

(21) Appl. No.: 17/839,024

(22) Filed: Jun. 13, 2022

(65) Prior Publication Data

US 2023/0010106 A1 Jan. 12, 2023

Related U.S. Application Data

(62) Division of application No. 16/631,437, filed as application No. PCT/US2018/043096 on Jul. 20, 2018, now Pat. No. 11,414,478.

(30) Foreign Application Priority Data

Jul. 21, 2017 (EP) .................................... 17182507

(51) Int. Cl.
*C07K 16/00* (2006.01)
*A01K 67/0275* (2024.01)
*A01K 67/0278* (2024.01)

(52) U.S. Cl.
CPC .......... *C07K 16/00* (2013.01); *A01K 67/0275* (2013.01); *A01K 67/0278* (2013.01); *A01K 2207/15* (2013.01); *A01K 2217/05* (2013.01); *A01K 2227/105* (2013.01); *A01K 2267/01* (2013.01); *C07K 2317/522* (2013.01); *C07K 2317/524* (2013.01); *C07K 2317/526* (2013.01); *C07K 2317/622* (2013.01); *C07K 2317/64* (2013.01); *C07K 2319/03* (2013.01)

(58) Field of Classification Search
None
See application file for complete search history.

(56) References Cited

U.S. PATENT DOCUMENTS 5,591,669 A 1/1997 Krimpenfort et al.
5,593,598 A 1/1997 Mcginness et al.
5,612,205 A 3/1997 Kay et al.
5,661,016 A 8/1997 Lonberg et al.
5,789,650 A 8/1998 Lonberg et al.
5,814,318 A 9/1998 Lonberg et al.
5,874,299 A 2/1999 Lonberg et al.
5,877,397 A 3/1999 Lonberg et al.
6,023,010 A 2/2000 Krimpenfort et al.
6,091,001 A 7/2000 Jakobovits et al.
6,130,364 A 10/2000 Jakobovits et al.
6,162,963 A 12/2000 Kucherlapati et al.
6,570,061 B1 5/2003 Rajewsky et al.
6,596,541 B2 7/2003 Murphy et al.
6,673,986 B1 1/2004 Kucherlapati et al.
7,041,871 B1 5/2006 Lonberg et al.
7,064,244 B2 6/2006 Jakobovits et al.
7,145,056 B2 12/2006 Jakobovits et al.
8,754,287 B2 6/2014 Macdonald et al.
8,796,424 B2 8/2014 Croasdale et al.
8,940,871 B2 1/2015 Wu et al.
10,519,234 B2 12/2019 Morel et al.
2013/0219535 A1 8/2013 Wabl et al.
2014/0120123 A1 5/2014 Wilhelmina Dooper et al.
2017/0058052 A1 3/2017 Wabl et al.
2017/0226162 A1 8/2017 Killeen et al.
2020/0048345 A1 2/2020 Rossi et al.

FOREIGN PATENT DOCUMENTS

JP 2012-528092 A 11/2012
JP 2013-116897 A 6/2013
KR 2016-0103109 A 8/2016
WO 2006/033413 A1 3/2006
WO 2009/018386 A1 2/2009
WO 2010/136172 A1 12/2010
WO 2013/119966 A2 8/2013

(Continued)

OTHER PUBLICATIONS

Araki K et al., "Targeted integration of DNA using mutant lox sites in embryonic stem cells," Nucleic Acids Research, 1997, vol. 25, No. 4, pp. 868-872.
Baer A. et al., "Coping with kinetic and thermodynamic barriers: RMCE, an efficient strategy for the targeted integration of transgenes," Current Opinion in Biotechnology, 2001, vol. 12, No. 5, pp. 473-480.
Bassing C et al., "The Mechanism and Regulation of Chromosomal V(D)J Recombination," Cell, vol. 109 Suppl, Apr. 2002 pp. 45-55.
Bole D. et al., "Post translational assocation of immunogloubulin Heavy Chain Binding Protein with Nascent Heavy Chains in Nonsecreting and Secreting Hybridomas," The Journal of Cell Biology, vol. 102, No. 5, pp. 1558-1566.
Brekke O H et al., "The structural requirements for complement activation by IgG: does it hinge on the hinge?" Immunology today, 1995, vol. 16, No. 2, pp. 85-89.

(Continued)

*Primary Examiner* — Celine X Qian
(74) *Attorney, Agent, or Firm* — MEDLER FERRO WOODHOUSE & MILLS PLLC

(57) ABSTRACT

The present invention provides cells, transgenic animals, including transgenic mammals and particularly rodents comprising engineered immunoglobulin (Ig) alleles. Such engineered alleles, wherein an Ig light chain CL exon [Cκ or Cλ (Cλ1, Cλ2 or Cλ3)] is incorporated into the Ig heavy chain locus, are capable of producing heavy chain-only antibodies as a single chain VH antibody (scVHAb) or heavy chain antibody (HCAb) comprising two extended scVHAbs. The scVHAb comprises an antigen-binding part consisting of a VH domain and the immunoglobulin constant domains CL, which is either Cκ or Cλ, and CH1, in the orderfrom N-terminus to C-terminus: VH-L1-CL-L2-CH1, wherein L1 and L2 are each, independently, peptidic linkers; and wherein CL is paired with CH1 through beta-sheet contact thereby obtaining a CL/CH1 dimer.

10 Claims, 34 Drawing Sheets

Figures 2A, 2B:
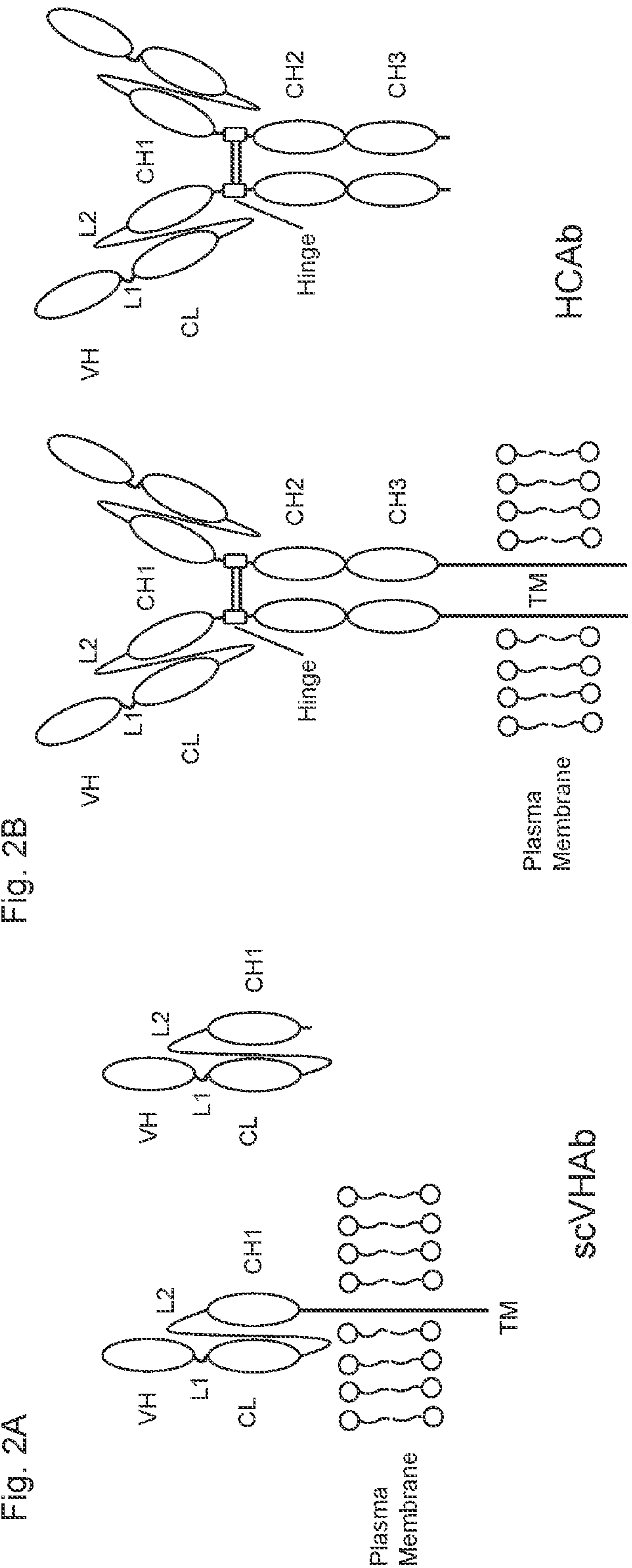

Specification includes a Sequence Listing.

(56) References Cited

FOREIGN PATENT DOCUMENTS

| | | |
|---|---|---|
| WO | 2014/141192 A2 | 9/2014 |
| WO | 2015/103072 A1 | 7/2015 |
| WO | 2015/168643 A2 | 11/2015 |
| WO | 2016/207273 A2 | 12/2016 |
| WO | 2017/035252 A1 | 3/2017 |
| WO | 2017/055388 A2 | 4/2017 |

OTHER PUBLICATIONS

Brevini T A L et al., “No shortcuts to pig embryonic stem cells,” Theriogenology, 2010, vol. 74, No. 4, pp. 544-550.
Burton et al., Structure and function of antibodies, 1987, vol. 17, chapter: 1, pp. 1-50.
Chenna R. et al., “Mulitple sequence alignment with the Clustal series of programs,” Nucleic Acids Research, 2003, vol. 31, No. 13, pp. 3497-3500.
Corcos D. et al., “B-cell receptors and heavy chain diseases: guilty by association?” Blood, 2011, vol. 117, No. 26, pp. 6991-6998.
De Los Rios M. et al., “Structural and genetic diversity in antibody repertoires from diverse species,” Current Opinion Structure Biology, 2015, vol. 33, pp. 27-41.
Ezashi T et al., “Pluripotent Stem Cells from Domesticated Mammals,” Annu Rev Anim Biosci, 2016, vol. 4, pp. 223-253.
Franklin E. C. et al., “Heavy Chain Disease—A New Disorder of Serum v-Gloubulins,” American Journal of Medicine, vol. 37, pp. 332-350.
Guidicelli V. et al., “IMGT/LIGM-DB, the IMGT® comprehensive database of immunoglobulin and T cell receptor nucleotide sequences,” Nucleic Acids Research, 2006, vol. 34, pp. 781-784.
Guo X et al., “Targeted genome editing in primate embryos,” Cell Res., 2015, vol. 25, No. 7, pp. 767-768.
Haas I. et al., “Immunoglobulin heavy chain binding protein,” Nature, 2006, vol. 306, No. 5941, pp. 387-389.
He X. et al., “Knock-in of large reporter genes in human cells via CRISPR/Cas9-induced homology-dependent and independent DNA repair,” Nucleic Acids Research, 2016, vol. 44, No. 9, e85.
Hoess R. et al., “The role of the loxP spacer region in P1 site-specific recombination,” Nucleic Acids Research, 1986, vol. 14, No. 5, pp. 2287-2300.
Hong J et al., “Derivation and characterization of embryonic stem cells lines derived from transgenic Fischer 344 and Dark Agouti rats,” Stem Cells and Development, 2012, vol. 21, No. 9, pp. 1571-1586.
Hsu P D et al., “DNA targeting specificity of RNA-guided Cas9 nucleases,” Nat Biotechnology, 2013, vol. 31, No. 9, pp. 827-832.
Ivics Z et al., “Germline transgenesis in pigs by cytoplasmic microinjection of Sleeping Beauty transposons,” Nature Prot., 2014, vol. 9, No. 4, pp. 810-827.
Jakobovits A et al., “Germ-line transmission and expression of human-derived yeast artificial chromosome,” Nature, 1993, 362(6417):255-258.
Kaushik A, et al., “Novel insight into antibody diversification from cattle,” Veterinary Immunology and inmunopathology, 2002, vol. 87, No. 3-4, pp. 347-350.
Khodarovich et al., “Expression of eukaryotic recombinant proteins and deriving them from the milk of transgenic animals,” Applied Biochem and Microbiol., 2013, vol. 49, No. 9, pp. 711-722.
Klein M. et al., “Equilibrium and Kinetic Aspects of the Interaction of Isolated Variable and Constant Domains of Light Chain with the Fd' Fragment of Immunoglobulin G,” Domain Association in Immunglobulin G, 1979, vol. 18, No. 8, pp. 1473-1481.
Kohler G. et al., “Continuous cultures of fused cells secreting antibody of predefined specificity,” Nature, 1975, vol. 256, No. 5517, pp. 495-497.
Kozbor D. et al., “A Human Hybrid Myeloma for Production of Human Monoclonal Anitbodies,” The Journal of Immunology, 1984, vol. 133, No. 6, pp. 3001-3005.
Kunkel T., “Rapid and efficient site-specific mutagenesis without phenotypic selection,” Proc. Natl. Acad. Sci. USA, 1985, vol. 82, pp. 488-492.
Langer S. et al., “A genetic screen identifies novel non-compatible loxP sites,” Nucleic Acids Research, 2002, vol. 30, No. 14, pp. 3067-3077.
Lee G. et al., “Role of nucleotide sequences of loxP spacer region in Cre-mediated recombination,” Gene: An International Journal on Genes and Genomes, 1998, vol. 216, No. 1, pp. 55-65.
Lee L. et al., “Strand Selection by the Tyrosine Recombinases,” Progress in Nucleic Acid Research and Molecular Biology, 2005, vol. 80, pp. 1-42.
Lee et al., “Developing genetically engineered mouse models using engineered nucleases: Current status, challenges, and the way forward,” Drug Discovery Today: Disease Models, 2016, vol. 20, pp. 13-20.
Liu X et al., “Trisomy eight in ES cells is a common potential problem in gene targeting and interferes with germ line transmission,” Developmental Dynamics, 1997, vol. 209, No. 1, pp. 85-91.
Lundvist M L et al., “Immunoglobulins of the non-galliform birds: Antibody expression and repertoire in the duck,” Developmental and Comparative Immunol., 2006, vol. 30, No. 1-2, pp. 93-100.
Maksimenko O G et al., “Use of Transgenic Animals in Biotechnology: Prospects and Problems,” Acta Naturae, 2013, vol. 5, No. 1, pp. 33-46.
Meng et al., “Optimized production of transgenic buffalo embryos and offspring by cytoplasmic zygote injection,” J. Animal Sci. and Biotech, 2015, 6,:44, pp. 1-7.
Munoz M et al., “Conventional pluripotency markers are unspecific for bovine embryonic-derived cell-lines,” Theriogenology, 2008, vol. 69, No. 9, pp. 1159-1164.
Munoz M et al., “Constraints to progress in embryonic stem cells from domestic species,” Stem Cell Rev and Rep, 2009, vol. 5, No. 1, pp. 6-9.
Paris D B B P et al., “Equine embryos and embryonic stem cells: Defining reliable markers of pluripotency,” Theriogenology, 2010, vol. 74, No. 4, pp. 516-524.
Parng C L, “Gene conversion contributes to lg light chain diversity in cattle,” J Immunol, 1996, vol. 157, No. 12, pp. 5478-5486.
Patil et al., “Transgenic animals and drug development: A review,” Indian J of Public Health research & Development, 2011, vol. 2, No. 1, pp. 106-109.
Schusser B. et al., “Expression of heavy chain-only antibodies can support B-cell development in light chain knockout chickens,” European Journal of Immunology, 2016, vol. 46, No. 9, pp. 2137-2148.
Tonegawa D., “Somatic generation of antibody diversity,” Nature, 1983, vol. 302, No. 5909, pp. 575-581.
Tong et al., “Production of p53 gene knockout rats by homologous recombination in embryonic stem cells,” Nature, 2010, vol. 467, No. 7312, pp. 211-213.
Übelhart R et al., “Assembly and Function of the Precursor B-Cell Receptor,” Current Topics in Microbiology and Immunology, 2016, vol. 393, pp. 3-25.
Vertebrate—Wikipedia p. 1 of 12; downloaded Sep. 10, 2021.
Weiner M. et al, “Site-directed mutagenesis of double-stranded DNA by the polymerase chain reaction,” Gene, 1994, vol. 151, No. 1-2, pp. 119-123.
West J et al., “Genome Editing in Large Animals,” J Equine Vet. Sci., 2016, vol. 41, pp. 1-6.
Wienands J. et al., “Multitasking of Ig-α and Ig-β to Regulate B cell antigen receptor function,” Intern. Rev. Immunol., 2001, vol. 20, pp. 679-696.
Yang C et al., “Mutant PFN1 causes ALS phenotypes and progressive motor neuron degeneration in mice by a gain of toxicity,” PNAS, 2016, vol. 113, No. 41, E6209-E6218, pp. 1-10.
Zou X. et al., “Heavy chain-only antibodies are spontaneously produced in light chain-deficient mice,” Journal of Experimental Medicine, 2007, vol. 204, No. 13, pp. 3271-3283.
Extended European Search Report issued Dec. 11, 2017, in EP Patent Application No. 17182507.8.
International Search Report issued Oct. 30, 2018, in International Application No. PCT/US2018/043096.

(56) References Cited

OTHER PUBLICATIONS

International Preliminary Report on Patentability issued Jan. 30, 2020 in International Application No. PCT/US2018/043096.
Office Action issued Feb. 21, 2020 in European Patent Application No. 18 749 716.9.
Japanese Office Action issued Feb. 17, 2021 in corresponding Japanese Patent Application No. 2020-502656.

Fig. 1

No HC
1
2
3
4
35
65
38
62
38
62
32
68
38
62
99
1
35
65
47
53
33
67
43
57
99.9
0.1
28
72
26
74
27
73
34
66
Surface hCD4
Surface migG1
Intracellular migG1
Cell number Reducing
Supernatants
Lysates
mIgG1
mIgG2a
Empty vector
VH-Fc
VH-Ck-(GGGGS)6-CH1-Fc
VH-Cκ-(GGGGS)10-CH1-Fc
VH-Cλ1-(GGGGS)10-CH1-Fc
VH-Cλ2-(GGGGS)10-CH1-Fc
VH-Fc
VH-Cκ-(GGGGS)6-CH1-Fc
VH-Cλ1-(GGGGS)10-CH1-Fc
VH-Cλ2-(GGGGS)10-CH1-Fc
1 2 3 4 5 6 7 8 9
185
115
80
65
50
30
25
15
10

A.
Pgk_TK_pA
IGHJ2-6
SHA
T3 promoter
FRT F5
CAG_PuroR_pA
FRT F5
Eμ
Ighg1 5' intron
Igkc 5' intron
IgCL
Targeting Vector
B.
Ighg1
L2
CH1
Hinge
CH2
CH3_S
TM1
TM2
3'UTR
3' intron
5' intron
Ighm
CH1
CH2
CH3
CH4_S
TM1
TM2
3'UTR
LHA F.
IGHD
IGHJ1-6
T3 promoter
FRT F5
Eμ
Ighg1 5' intron
Igkc 5' intron
IgCL
Targeted Igh locus
Δ CAG_PuroR_pA
G.
Ighg1
Ighm
L2
CH1
Hinge
CH2
CH3_S
TM1
TM2
3'UTR
3' intron
5' intron
CH1
CH2
CH3
CH4_S
TM1
TM2
3'UTR

Fig. 14B

Endogenous Igh locus

IGHD

IGHJ1-6

Eμ

S region

CH1

CH2

CH3

CH4_S

Ighm

3' intron

TM1

TM2

3'UTR

Fig. 14C

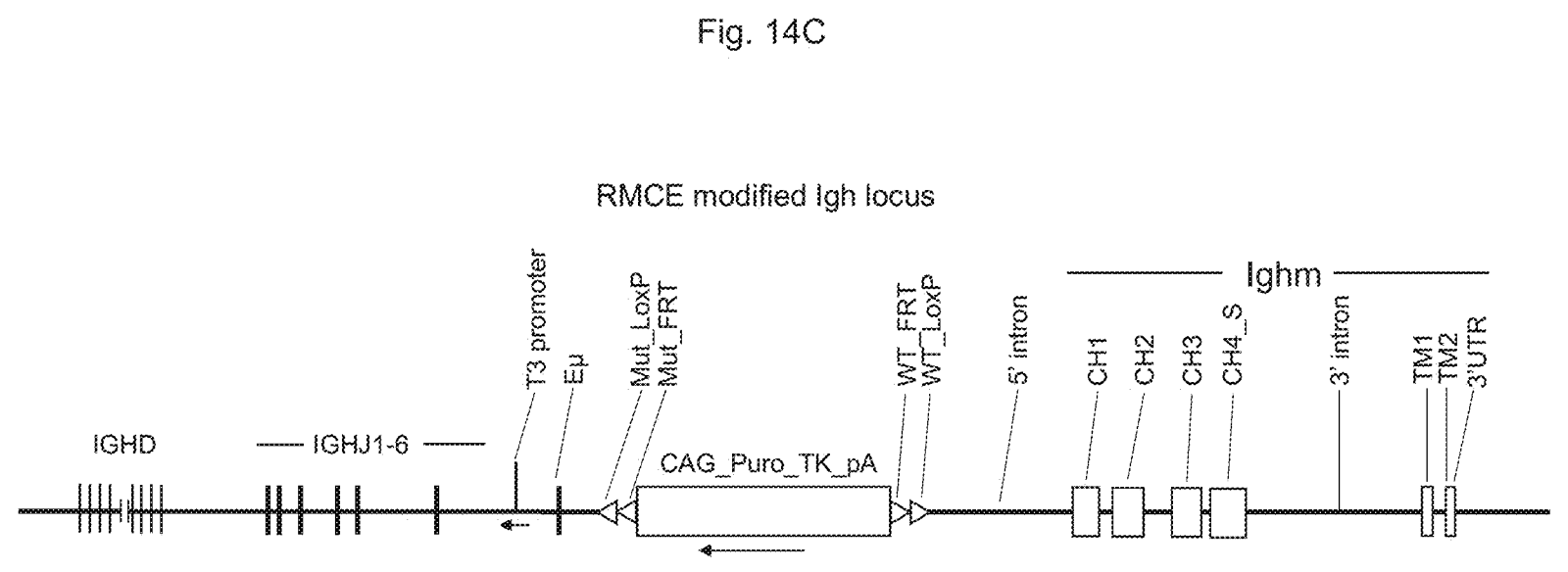

RMCE modified Igh locus

IGHD
IGHJ1-6
T3 promoter
Eμ
Mut_LoxP
Mut_FRT
CAG_Puro_TK_pA
WT_FRT
WT_LoxP
5' intron
CH1
CH2
CH3
CH4_S
Ighm
3' intron
TM1
TM2
3'UTR A.
Targeting vector
Ighg1
WT LoxP
WT FRT
3'UTR
TM2
TM1
3' intron
CH3_S
CH2
Hinge
CH1
L2
IgCL
Igkc 5' intron
Ighg1 5' intron
Mut FRT
Mut LoxP Fig. 15 (continued)

C.

IGHD
IGHJ1-6
T3 promoter
Eμ
Mut LoxP
Mut FRT
Ighg1 5' intron
Igkc 5' intron
IgCL
Targeted Igh locus

D.

Ighg1
L2
CH1
Hinge
CH2
CH3_S
3' intron
TM1
TM2
3'UTR
Ighm
5' intron
CH1
CH2
CH3
CH4_S
3' intron
TM1
TM2
3'UTR

Fig. 16

SEQ ID NO 1: PGK_TK_pA agtcagcttctgatggaattagaacttggcaaaacaatactgagaatgaagtgtatgtggaacagaggctgctgatctc
gttcttcaggctatgaaactgacacatttggaaaccacagtacttagaaccacaaagtgggaatcaagagaaaaacaat
gatcccacgagagatctatagatctatagatcatgagtgggaggaatgagctggcccttaatttggttttgcttgttta
aattatgatatccaactatgaaacattatcataaagcaatagtaaagagccttcagtaaagagcaggcatttatctaat
cccaccccacccccacccccgtagctccaatccttccattcaaaatgtaggtactctgttctcacccttcttaacaaag
tatgacaggaaaaacttccattttagtggacatctttattgtttaatagatcatcaatttctgcagacttacaggacgg
atcgatcccctcagttagcctcccccatctcccgggcaaacgtgcgcgccaggtcgcatatcgtcggtatggagccggg
ggtggtgacgtgggtctggaccatcccggaggtaagttgcagcagggcgtcccggcagccggcgggcgattggtcgtaa
tccaggataaagacgtgcatggaacggaggcgtttggccaagacgtccaaggcccaggcaaacacgttatacaggtcgc
cgttgggggccagcaactcgggggcccgaaacagggtaaataacgtgtccccgatatggggtcgtgggcccgcgttgct
ctggggctcggcaccctggggcggcacggccgtccccgaaagctgtccccagtcctcccgccacgacccgccgcactgc
agataccgcaccgtattggcaagtagcccgtaaacgcggcgaatcgcagccagcatagccaggtccagccgctcgccgg
ggcgctggcgtttggccaggcggtcgatgtgtctgtcctccggaagggccccaagcacgatgttggtgccgggcaaggt
cggcgggatgagggccacgaacgccagcacggcctgggggtcatgctgcccataaggtaccgcgcggccgggtagcac
aggagggcggcgatgggatggcggtcgaagatgagggtgagggccgggggcggggcatgtgagctcccagcctcccccc
cgatatgaggagccagaacggcgtcggtcacggcataaggcatgcccattgttatctgggcgcttgtcattaccaccgc
cgcgtccccggccgatatctcaccctggtcgaggcggtgttgtgtggtgtagatgttcgcgattgtctcggaagccccc
agcacccgccagtaagtcatcggctcgggtacgtagacgatatcgtcgcgcgaacccagggccaccagcagttgcgtgg
tggtggttttccccatcccgtggggaccgtctatataaacccgcagtagcgtgggcattttctgctccgggcggacttc
cgtggcttcttgctgccggcgagggcgcaacgccgtacgtcggttgctatggccgcgagaacgcgcagcctggtcgaac
gcagacgcgtgttgatggccggggtacgaggccatgatggcaaggacggtgcattggctgcaggtcgaaaggcccggag
atgaggaagaggagaacagcgcggcagacgtgcgcttttgaagcgtgcagaatgccgggcctccggaggaccttcgggc
gcccgccccgcccctgagcccgcccctgagcccgcccccggacccaccccttcccagcctctgagcccagaaagcgaag
gagcaaagctgctattggccgctgccccaaaggcctacccgcttccattgctcagcggtgctgtccatctgcacgagac
tagtgagacgtgctacttccatttgtcacgtcctgcacgacgcgagctgcggggcgggggggaacttcctgactagggg
aggagtagaaggtggcgcgaaggggccaccaaagaacggagccggttggcgcctaccggtggatgtggaatgtgtgcga
ggccagaggccacttgtgtagcgccaagtgcccagcggggctgctaaagcgcatgctccagactgccttgggaaaagcg
cctcccctacccggtagaattgacctgccggggccctcgaatcctgcag Fig. 16 (continued)

SEQ ID NO 2: Short homology arm (SHA)
GGGTCTATAATTACTCTGATGTCTAGGACCAGGGGGCTCAGGTCACTCAGGTCAGGTGAGTCCTGCATCTGGGGACTGT
GGGGTTCAGGTGGCCTAAGGCAGGATGTGGAGAGAGTTTTAGTATAGGAACAGAGGCAGAACAGAGACTGTGCTACTGG
TACTTCGATGTCTGGGGCACAGGGACCACGGTCACCGTCTCCTCAGGTAAGCTGGCTTTTTTCTTTCTGCACATTCCAT
TCTGAAACGGGAAAAGATATTCTCAGATCTCCCCATGTCAGGCCATCTGCCACACTCTGCATGCTGCAGAAGCTTTTCT
GTAAGGATAGGGTCTTCACTCCCAGGAAAAGAGGCAGTCAGAGGCTAGCTGCCTGTGGAACAGTGACAATCATGGAAAA
TAGGCATTTACATTGTTAGGCTACATGGGTAGATGGGTTTTTGTACACCCACTAAAGGGGTCTATGATAGTGTGACTAC
TTTGACTACTGGGGCCAAGGCACCACTCTCACAGTCTCCTCAGGTGAGTCCTTACAACCTCTCTCTTCTATTCAGCTTA
AATAGATTTTACTGCATTTGTTGGGGGGAAATGTGTGTATCTGAATTTCAGGTCATGAAGGACTAGGGACACCTTGGG
AGTCAGAAAGGGTCATTGGGAGCCCTGGCTGACGCAGACAGACATCCTCAGCTCCCATACTTCATGGCCAGAGATTTAT
AGGGATCCTGGCCAGCATTGCCGCTAGGTCCCTCTCTTCTATGCTTTCTTTGTCCCTCACTGGCCTCCATCTGAGATCA
TCCTGGAGCCCTAGCCAAGGATCATTTATTGTCAGGGGTCTAATCATTGTTGTCACAATGTGCCTGGTTTGCTTACTGG
GGCCAAGGGACTCTGGTCACTGTCTCTGCAGGTGAGTCCTAACTTCTCCCATTCTAAATGCATGTTGGGGGGATTCTGG
GCCTTCAGGACCAAGATTCTCTGCAAACGGGAATCAAGATTCAACCCCTTTGTCCCAAAGTTGAGACATGGGTCTGGGT
CAGGGACTCTCTGCCTGCTGGTCTGTGGTGACATTAGAACTGAAGTATGATGAAGGATCTGCCAGAACTGAAGCTTGAA
GTCTGAGGCAGAATCTTGTCCAGGGTCTATCGGACTCTTGTGAGAATTAGGGGCTGACAGTTGATGGTGACAATTTCAG
GGTCAGTGACTGTCTGGTTTCTCTGAGGTGAGGCTGGAATATAGGTCACCTTGAAGACTAAAGAGGGGTCCAGGGGCTT
CTGCACAGGCAGGGAACAGAATGTGGAACAATGACTTGAATGGTTGATTCTTGTGTGACACCAGGAATTGGCATAATGT
CTGAGTTGCCCAGGGGTGATTCTAGTCAGACTCTGGGGTTTTTGTCGGGTATAGAGGAAAAATCCACTATTGTGATTAC
TATGCTATGGACTACTGGGGTCAAGGAACCTCAGTCACCGTCTCCTCAGGTAAGAATGGCCTCTCCAGGTCTTTATTTT
TAACCTTTGTTATGGAGTTTTCTGAGCATTGCAGACTAATCTTGGATATTTGTCCCTGAGGGAGCCGGCTGAGAGAAGT
TGGGAAATAAACTGTCTAGGGATCTCAGAGCCTTTAGGACAGATTATCTCCACATCTTTGAAAAACTAAGAATCTGTGT
GATGGTGTTGGTGGAGTCCCTGGATGATGGGATAGGGACTTTGGAGGCTCATTTGAAGAAGATGCTAAAACAATCCTAT
GGCTGGAGGGATAGTTGGGGCTGTAGTTGGAGATTTTCAGTTTTTAGAATAAAAGTATTAGTTGTGGAATATACTTCAG
GACCACCTCTGTGACAGCATTTATACAGTATCCGATGCATAGGGACAAAGAGTGGAGTGGGGCACTTTCTTTAGATTTG
TGAGGAATGTTCCGCACTAGATTGTTTAAAACTTCATTTGTTGGAAGGAGAGCTGTCTTAGTGATTGAGTCAAGGGAGA
AAGGCATCTAGCCTCGGTCTCAAAAGGGTAGTTGCTGTCTAGAGAGGTCTGGTGGAGCCTGCAAAAGTCCAGCTTTCAA
AGGAACACAGAAGTATGTGTATGGAATATTAGAAGATGTTGCTTTTACTCTTAAGTTGGTTCCTAGGAAAAATAGTTAA
ATACTGTGACTTTAAAATGTGAGAGGGTTTTCAAGTACTCATTTTTTTAAATGTCCAAAATTCTTGTCAATCAGTTTGA
GGTCTTGTTTGTGTAGAACTGATATTACTTAAAGTTTAACCGAGGAATGGGAGTGAGGCTCTCTCATAACCTATTCAGA
ACTGACTTTTAACAATAATAAATTAAGTTTCAAATATTTTTAAATGAATTGAGCAATGTTGAGTTGGAGTCAAGATGGC
CGATCAGAACCAGAACACCTGCAGCAGCTGGCAGGAAGCAGGTCATGTGGCAAGGCTATTTGGGGAAGGGAAAATAAAA
CCACTAGGTAAACTTGTAGCTGTGGTTTGAAGAAGTGGTTTTGAAACACTCTGTCCAGC SEQ ID NO 3: T3 promoter
cctttagtgagggttaatt SEQ ID NO 4: 5' FRT site
gaagttcctattccgaagttcctattcttcaaaaggtataggaacttc Fig. 16 (continued)

SEQ ID NO 5: CAG_PuroR_pA
tcattctggcctcccctcccccaaggtcattctggcctcccctcccccaaggtcattctggcctcccctccccctt
ggccgcgcctcattctggcctcccctcccccaaggcacacaaaaaaccaacacacagatctattgaaaataatgatct
tttattgatccgcgcctggatctcgaaccggttcaggcaccgggcttgcgggtcatgcaccaggtgcgcggtccttcgg
gcacctcgacgtcggcggtgacggtgaagccgagccgctcgtagaaggggaggttgcggggcgcggaggtctccaggaa
ggcgggcaccccggcgcgctcggccgcctccactccggggagcacgacggcgctgcccagacccttgccctggtggtcg
ggcgagacgccgacggtggccaggaaccacgcgggctccttgggccggtgcggcgccaggaggccttccatctgttgct
gcgcggccagccgggaaccgctcaactcggccatgcgcgggccgatctcggcgaacaccgcccccgcttcgacgctctc
cggcgtggtccagaccgccaccgcggcgccgtcgtccgcgacccacaccttgccgatgtcgagcccgacgcgcgtgagg
aagagttcttgcagctcggtgacccgctcgatgtggcggtccgggtcgacggtgtggcgcgtggcggggtagtcggcga
acgcggcggcgagggtgcgtacggcccggggacgtcgtcgcgggtggcgaggcgcaccgtgggcttgtactcggtcat
ggaaggctaggcggatcggcgatcgctccggaggccgccctgggagtggacacctgtggagagaaaggcaaagtggatg
tcaatgtcactcaagtgtatggccagatctcaagcctgccacacctcaagcttgacaacaaaaagattgtcttttctga
ccagatggacgcggccaccctcaaaggcatcaccgcgggccaggtgaatatcaaatcctcctcgttttggaaactgac
aatcttagcgcagaagtcatgcccgcttttgagagggagtactcaccccaacgcttctagagccgccggtcacacgcca
gaagccgaaccccgccctgccccgtcccccccgaaggcagccgtcccccgcggacagccccgaggctggagagggaga
aggggacggcggcgcggcgacgcacgaaggccctccccgcccatttccttcctgccggcgccgcaccgcttcgccccgc
gcccgctagagggggtgcggcggcgcctcccagatttcggctccgcacagatttgggacaaaggaagtccctgcgccct
ctcgcacgattaccataaaaggcaatggctgcggctcgccgcgcctcgacagccgccggcgctccgggggccgccgcgc
ccctcccccgagccctccccggcccgaggcggccccgccccgcccggcaccccacctgccgccacccccgcccggca
cggcgagccccgcgccacgccccgtacggagccccgcacccgaagccgggccgtgctcagcaactcggggaggggggtg
caggggggggttgcagcccgaccgacgcgcccacaccccctgctcacccccccacgcacacaccccgcacgcagcctttg
ttcccctcgcagcccccccgcaccgcggggcaccgccccggccgcgctcccctcgcgcacactgcggagcgcacaaa
gccccgcgccgcgcccgcagcgctcacagccgccgggcagcgcggagccgcacgcggcgctccccacgcacacacacac
gcacgcacccccccgagccgctcccccgcacaaagggccctcccggagcccctcaaggctttcacgcagccacagaaaa
gaaacaagccgtcattaaaccaagcgctaattacagcccggaggagaagggccgtcccgcccgctcacctgtgggagta
acgcggtcagtcagagccggggcgggcggcgcgaggcggcggcggagcggggcacggggcgaaggcagcgcgcagcgac
tcccgcccgccgcgcgcttcgcttttttatagggccgccgccgccgccgcctcgccataaaggaaactttcggagcgcg
ccgctctgattggctgccgccgcacctctccgcctcgccccgccccgcccctcgccccgccccgccccgcctggcgcgc
gcccccccccccccccgccccatcgctgcacaaaataattaaaaaataaataaatacaaaattggggggtggggagggggg
gggagatggggagagtgaagcagaacgtggggctcacctcgaccatggtaatagcgatgactaatacgtagatgtactg
ccaagtaggaaagtcccataaggtcatgtactgggcataatgccaggcgggccatttaccgtcattgacgtcaataggg
ggcgtacttggcatatgatacacttgatgtactgccaagtgggcagtttaccgtaaatactccacccattgacgtcaat
ggaaagtccctattggcgttactatgggaacatacgtcattattgacgtcaatgggcgggggtcgttgggcggtcagcc
aggcgggccatttaccgtaagttatgtaacgcggaactccatatatgggctatgaactaatgaccccgtaattgattac
tattaataactagtcaataatcaat SEQ ID NO 6: 3′ FRT site
gaagttcctattccgaagttcctattcttcaaaaggtataggaacttc SEQ ID NO 7: Mouse Igh Eμ
ctgcagcagctggcaggaagcaggtcatgtggcaaggctatttggggaagggaaaataaaaccactaggtaaacttgta
gctgtggtttgaagaagtggttttgaaacactctgtccagccccaccaaaccgaaagtccaggctgagcaaaacaccac
ctgggtaatttgcatttctaaaataagttgaggattcagccgaaactggagaggtcctcttttaacttattgagttcaa
ccttttaatttagcttgagtagttctagtttccccaaacttaagtttatcgacttctaaaatgtatttagaattc Fig. 16 (continued)

SEQ ID NO 8: Ighg1 5' intron
ttaaaaaaaaaaaaaaaggaaagggacttctctgtgtttggcaacacaagtgcgatgcacaggcaggaagatcaaatct
gtcccaacaatacaggggacagagggtcaacctacaaaggaaagaacctggggcagtgtgaagacaacactgtagaag
ccaaggctgagttcactgagctctcgttagtgagactacacagcaaggaggtggcgggcactgagcagtgaggccccgg
gaagtgggggtgatggtggtgacggtggtaactgttaagaactggggaaagaattgtggagaaccaagctaaatagtt
atgtcaaaccacatgtttaggagcctgggttgacttcatagggagtaggcatggaggctaatctagaggtttgtgtata
ggcaagaagtgaatcctgacccaagaatagagagtgctaaacggacttagttcaaagacaactgaaaaagacaatgcct
gcaaaacaaagctaaggccagagctcttggactatgaagagttcagggaacctaagaacagggaccatctgtgtacagg
ccaaggccggtagaagcagcctaggaagtgtcaagagccaacgtggctgggtgggcaaagacaggaagggactgttagg
ctgcagggatgtgccgacttcaatgtgcttcagtattgtccagattgtgtgcagccatatggcccaggtataagaggtt
taacagtggaacacagatgcccacatcagacagctgggggcgggggtgaacacagatacccatactggaaagcaggtg
gggcattttcctaggaacgggactgggctcaatggcctcaggtctcatctggtctggtgatcctgacattgataggccc
aaatgttggatatcacctactccatgtagagagtcggggacatgggaagggtgcaaaagagcggccttctagaaggttt
ggtcctgtcctgtcctgtctgacagtgtaatcacatatactttttcttgtag SEQ ID NO 9: Mouse IgkC (Cκ) 5' intron sequence
ataatacactgaaatggagcccttccttgttacttcataccatcctctgtgcttccttcctcag SEQ ID NO 10: Mouse IgkC (Cκ). (The tgt codon at the 3′ end of this sequence encodes the Cys that forms the interchain disulfide bond with CH1)
gggctgatgctgcaccaactgtatccatcttcccaccatccagtgagcagttaacatctggaggtgcctcagtcgtgtg
cttcttgaacaacttctaccccaaagacatcaatgtcaagtggaagattgatggcagtgaacgacaaaatggcgtcctg
aacagttggactgatcaggacagcaaagacagcacctacagcatgagcagcaccctcacgttgaccaaggacgagtatg
aacgacataacagctatacctgtgaggccactcacaagacatcaacttcacccattgtcaagagcttcaacaggaatga
gtgt SEQ ID NO 11: Linker 2 repeat sequence
GGAGGAGGGGGTCC SEQ ID NO 12: Mouse Ighg1_CH1
aaaacgacacccccatctgtctatccactggcccctggatctgctgcccaaactaactccatggtgaccctgggatgcc
tggtcaagggctatttccctgagccagtgacagtgacctggaactctggatccctgtccagcggtgtgcacaccttccc
agctgtcctgcagtctgacctctacactctgagcagctcagtgactgtcccctccagcacctggcccagccagaccgtc
acctgcaacgttgcccacccggccagcagcaccaaggtggacaagaaaattg SEQ ID NO 13: Mouse Ighg1_CH1 protein sequence. (The Cys at position 81 forms the interchain disulfide bond with Cκ.)
KTTPPSVYPL APGSAAQTNS MVTLGCLVKG YFPEPVTVTW NSGSLSSGVH TFPAVLQSDL
YTLSSSVTVP SSTWPSQTVT CNVAHPASST KVDKKI SEQ ID NO 14: Mouse Ighg1_Hinge
tgcccagggattgtggttgtaagccttgcatatgtacag SEQ ID NO 15: Mouse Ighg1_CH2
tcccagaagtatcatctgtcttcatcttccccccaaagcccaaggatgtgctcaccattactctgactcctaaggtcac
gtgtgttgtggtagacatcagcaaggatgatcccgaggtccagttcagctggtttgtagatgatgtggaggtgcacaca
gctcagacgaaaccccgggaggagcagatcaacagcactttccgttcagtcagtgaacttcccatcatgcaccaggact
ggctcaatggcaaggagttcaaatgcagggtcaacagtgcagctttccctgcccccatcgagaaaaccatctccaaaac
caaag Fig. 16 (continued)

SEQ ID NO 16: Mouse Ighg1_CH3
gcagaccgaaggctccacaggtgtacaccattccacctcccaaggagcagatggccaaggataaagtcagtctgacctg
catgataacaaacttcttccctgaagacattactgtggagtggcagtggaatgggcagccagcggagaactacaagaac
actcagcccatcatggacacagatggctcttacttcgtctacagcaagctcaatgtgcagaagagcaactgggaggcag
gaaatactttcacctgctctgtgttacatgagggcctgcacaaccaccatactgagaagagcctctcccactctcctgg
taaa SEQ ID NO 17: Mouse Ighg1_TM1
gggctgcaactggacgagacctgtgctgaggcccaggacggggagctggacgggctctggacgaccatcaccatcttca
tcagcctcttcctgctcagtgtgtgctacagcgctgctgtcacactcttcaag SEQ ID NO 18: Mouse Ighg1_TM2
gtaaagtggatcttctcctcggtggtggagctgaagcagacactggttcctgaatacaagaacatgattgggcaagcac
cc SEQ ID NO 19: Mouse Ighg1_3' UTR
taggccacctcctgtaatggcatttcccaggccccgaaggaccctgtccaatatgccaagcagcacaactgagatcaca
ctgtctgctcatctcgctttcctccgaccccgagactcagctactctcaaattttccctctctgaaggaccatgtggac
attacattgctccaggccacagccaccaggacctaaaacaccatcacagcagcaccaaagacactggatagacccacaa
gggcaatagtttcctcaacagtatatccaaactgttgggacaaacgagcaatcactgaagaagtgacaagttcccacaa
tgtcagtgtccagctgagaagggacaaaaagtggtaccagccctgtccacaccaccttctaattcacaggaatacgtga
tagaagaggcaggttgtagatccgaaagatgagacagattttatcaactccagaaagagctgggtccaactgaattatt
ctagcgaccttggcattgtcatgacctgccatgaccttcctccttaacacttcgataaaccctgggatatggaaaatgc
ctgtgtttctcagggtttgggaaagaaccatccatgttgggattcttgtgtagatcctccttctggtcacagatgcaat
acactggattttcaggcaaaggagcaaattcacagacaactctggccctacagccctaagacctagacaccaccatctc
cttggaattatcaaatttaacacccggcacacaacaaagaaggactgggactttgaggcctttgtgtagccctagaggg
ggcagaggccactgagcagggattgggtgatcacaaggacctcctggagagggacctgaggagcaggttccaattgggc
caaagaaagaagaacaacaatagagatgaaggatgctggaaagagccatggtacagcagtcttgtccttcagacatgac
tcttacagcccaggactcttacagtagctagctggagcagaagtccaagggattaccatgccctagggccacaggctac
tggagggtggagtgagtctactacacaggtccaatgcctgtttctccattgcttctcagccaatgagaaatcagagtct
ccacctccaagaaaaaggaaggtggaaatgaaaggtgagcacctgccttcccgtgactggcagaaagatctccacggac
tcaaggctttgacttcaaacttcccgtagatccctgatgtctttaaggactctgtctgctttgttggttttgtttgttt
gttttgtactttgtcaataaaacattttcaaatattctacaattgctgtgctcttcctatgcaaactggccctgg SEQ ID NO 20: Mouse Ighg1_3' intron
cacttcaaaacatggcacagttaagttgaccagtgggccatgcagagcatactacccctcctggtcctgtgtcctacca
gatatcctctaagtgtcccttcactgctgggctccagttctgctgccctgaaccacacaggtcctcagtctgtcctccc
tatgggcagtttcatcccagccagaagctgccctgtggcccctaggctgcccaggcatggtctcccacaccaaccacac
aaactaagaagcctgtcccatacattgacctcaggctcagtgataacatttctatagaaaaggaaaggaataagaaaa
aaaaaactccatattacatgggggctgcctaccttgctgatgcttattgtctcaagcaagtttggagaagttccaaatc
aggcactgacagggtgggttctcagccatgctcttcttacctggtaggtgccttctcccccatggcacctcacaggctc
tccatctgtgtgtgtctgggtcctgatctcttctcataagtacaaagtcaggctggaagaggtacaccctagccctcat
tataacttaccagtttatgatcctgtctgcaaacatctgaggtccctgtggctcaaatgtcaattagtgagtcttctgg
ggacagaatttagtccacattagctctc Fig. 16 (continued)

SEQ ID NO 21: Long homology arm (LHA)
ggtgttcatgcccctagagttggctgaagggccagatccacctactctagaggcatctctccctgtctgtgaaggcttccaaa
gtcacgttcctgtggctagaaggcagctccatagccctgctgcagtttcgtcctgtataccaggttcacctactaccatatct
agccctgcctgccttaagagtagcaacaaggaaatagcagggtgtagagggatctcctgtctgacaggaggcaagaagacaga
ttcttacccctccatttctcttttatccctctctggtcctcagagagtcagtccttcccaaatgtcttcccccctcgtctcctg
cgagagccccctgtctgataagaatctggtggccatgggctgcctggcccgggacttcctgcccagcaccatttccttcacct
ggaactaccagaacaacactgaagtcatccagggtatcagaaccttcccaacactgaggacaggggcaagtacctagccacc
tcgcaggtgttgctgtctcccaagagcatccttgaaggttcagatgaatacctggtatgcaaaatccactacggaggcaaaaa
caaagatctgcatgtgcccattccaggtaagaaccaaaccctcccagcaggggtgcccaggcccaggcatggcccagagggag
cagcggggtggggcttaggccaagctgagctcacaccttgacctttcattccagctgtcgcagagatgaaccccaatgtaaat
gtgttcgtcccaccacgggatggcttctctggccctgcaccacgcaagtctaaactcatctgcgaggccacgaacttcactcc
aaaaccgatcacagtatcctggctaaaggatgggaagctcgtggaatctggcttcaccacagatccggtgaccatcgagaaca
aaggatccacaccccaaacctacaaggtcataagcacacttaccatctctgaaatcgactggctgaacctgaatgtgtacacc
tgccgtgtggatcacaggggtctcaccttcttgaagaacgtgtcctccacatgtgctgccagtgagtggcctgggctaagccc
aatgcctagccctcccagattagggaagtcctcctacaattatggccaatgccacccagacatggtcatttgctccttgaact
ttggctccccagagtggccaaggacaagaatgagcaataggcagtagaggggtgagaatcagctggaaggaccagcatcttcc
cttaagtaggtttggggg atggagactaagctttttccaacttcacaactagatatgtcataacctgacacagtgttctctt
gactgcaggtccctccacagacatcctaaccttcaccatcccccctcctttgccgacatcttcctcagcaagtccgctaacc
tgacctgtctggtctcaaacctggcaacctatgaaaccctgaatatctcctgggcttctcaaagtggtgaaccactggaaacc
aaaattaaaatcatggaaagccatcccaatggcaccttcagtgctaagggtgtggctagtgtttgtgtggaagactggaataa
caggaaggaatttgtgtgtactgtgactcacagggatctgccttcaccacagaagaaattcatctcaaaacccaatggtaggt
atcccccctcccttcccctccaattgcaggacccttcctgtacctcatagggagggcaggtcctcttccaccctatcctcac
tactgtcttcatttacagaggtgcacaaacatccacctgctgtgtacctgctgccaccagctcgtgagcaactgaacctgagg
gagtcagccacagtcacctgcctggtgaagggcttctctcctgcagacatcagtgtgcagtggcttcagagagggcaactctt
gccccaagagaagtatgtgaccagtgccccgatgccagagcctggggccccaggcttctactttacccacagcatcctgactg
tgacagaggaggaatggaactccggagagacctatacctgtgttgtaggccacgaggccctgccacacctggtgaccgagagg
accgtggacaagtccactggtaaacccacactgtacaatgtctccctgatcatgtctgacacaggcggcacctgctattgacc
atgctagcgctcaaccaggcaggccctgggtgtccagttgctctgtgtatgcaaactaaccatgtcagagtgagatgttgcat
tttataaaaattagaaataaaaaaaatccattcaaacgtcactggttttgattatacaatgctcatgcctgctgagacagttg
tgttttgcttgctctgcacacaccctgcatacttgcctccaccctggcccttcctctaccttgccagtttcctccttgtgtgt
gaactcagtcaggcttacaacagacagagtatgaacatgcgattcctccagctacttctagatatatggctgaaagcttgcct
aacctggtgcaggcagcattcaggcacatatatagacacacatgcatttatacatagatatataggtacacatgtgTAGACAC
ATACATGAATGTGTATTCATGGACACACAGACAAAGGTACACATATATACACATGAGTTCATGCGCACACACATGCATGGACA
CTTACAAACGCCTTCAGAGACAAATAGGCATAGACACACAACCACTCACAGAAACAGATACCAATATGCATGGTCCTGTGTAC
ACAGAAACAGACTATAGGCAAATATACACAAATAAACTATATAGATACAAAGATATGCATATACACACATGTACAGAAACATC
TTCACATGTGTACACTAACATGTGAACAGGTATAGCACACAGATACACCTGGACTCTGACCAGGGCTGTAATCTCCAAGGCTC
ACGGCTCAGAGAGCCTACACTAGGCTGGGTCACTGATACTCCTCAGGAGCCCACTCTATGATTGGGAGAGATAACCCCAGGTA
CAAAGTATGCCTATCTGTCTCAACACCATGGGGCAGAAGATACTCCACTAACCACCCATGACAGAAAGTTAGCCTTGGCTGTG
TCTCCATTAATAGAACACCTCAGAAGACCAATGTGAAATTGCCTAACCCACTCACACCCACCCTGATCTCCAGTTCAAAATGC
AGAAAACATAATGCAGTTGTCCAAAAGATGCCCCAACCACACACACACACACACACACACACACACACACACACACACACACA
CACACACACACACACCATCAAGGAGCCTCTGTAAGGAGTCACCACCCAATAACACTGCCTCTTTGGGCTCATATCCTGGACAT
TCTTCATATTCATATCCATTTGGGGCCTAGGCTTTAGATATCCCCAAGGGCTCATCTTTACAGGGATCAGAGATCCCAATAAA
TGCCCTGGTCCCACAGCCTCCCTCAGGTATCTGTCTGTTTATCTCTTGGTACCAAGACCCAACATTGCTGGCAGGGGTAGGAC
AAGCAACGCACGGGAACTCTGATCAAAGAAAGTCATGAGATGCCTGAGTCCTTCAGGAAGTAAGGAGGGACAACCTCTGGTAT
CCCTGTTCTTATTGCTAAAGCCCAAGAGACAGGGAGACCTGCTCTAAATTCTCAGTCTAAACAGCACCGATGGCACCACCTGC
TCAGGGAAAGTCCAGAGCACACCAATATCATTTTGCCACAGTTCCTGAGTCTGCCTTTACCCAGGTCCATACATTGCATCTGT
CTTGCTTGCTCTGCTGCCCCAGGGCTCCTGGAACAAAGGCTCCAAATTAGTGTGTCCTACAGCTTGGCCTGTTCTGTGCCTCC
GTCTAGCTTGAGCTATTAGGGGACCAGTCAATACTCGCTAAGATTCTCCAGAACCATCAGGGCACCCCAACCCTTATGCAAAT
GCTCAGTCACCCCAAGACTTGGCTTGACCCTCCCTCTCTGTGTCCCTTCATAGAGGGGGAGGTGAATGCTGAGGAGGAAGGCT
TTGAGAACCTGTGGACCACTGCCTCCACCTTCATCGTCCTCTTCCTCCTGAGCCTCTTCTACAGCACCACCGTCACCCTGTTC
AAGGTAGTGTGGTTGTGGGGCTGAGGACACAGGGCTGGGACAGGGAGTCACCAGTCCTCACTGCCTCTACCTCTACTCCCTAC
AAGTGGACAGCAATTCACACTGTCTCTGTCACCTGCAGGTGAAATGACTCTCAGCATGGAAGGACAGCAGAGACCAAGAGATC
CTCCCACAGGGACACTACCTCTGGGCCTGGGATACCTGACTGTATGACTAGTAAACTTATTCTTACGTCTTTCCTGTGTTGCC
CTCCAGCTTTTATCTCTGAGATGGTCTTCTTTCTAGACTGACCAAAGACTTTTTGTCAACTTGTACAATCTGAAGCAATGTCT
GGCCCACAGACAGCTGAGCTGTAAACAAATGTCACATGGAAATAAATACTTTATCTTGTGAACTCACTTTATTGTGAAGGAAT
TTGTTTTGTTTTTCAAACCTTTCCTGCGGTGTTGACAGCCCAAGGATTATCTGAATAGAGCTTAGGAACTGGAAATGGAACAG
T Fig. 16 (continued)

SEQ ID NO 22: Human IGHG1 Hinge
gagcccaaatcttgtgacaaaactcacacatgcccaccgtgccca

SEQ ID NO 23: Human IGHG2 Hinge
gagcgcaaatgttgtgtcgagtgcccaccgtgccca

SEQ ID NO 24: Human IGHG3 Hinge
gagctcaaaaccccacttggtgacacaactcacacatgcccacggtgccca SEQ ID NO 25: Human IGHG4 Hinge
gagtccaaatatggtcccccatgcccatcatgccca SEQ ID NO 26: Human IGHA1 Hinge
gttccctcaactccacctaccccatctccctcaactccacctaccccatctccctca SEQ ID NO 27: Human IGHA2 Hinge
gttcccccacctcccccca SEQ ID NO 28: Mouse Ighg1 Hinge
tgcccagggattgtggttgtaagccttgcatatgtacag SEQ ID NO 29: Mouse Ighg2a Hinge
gagcccagagggcccacaatcaagccctgtcctccatgcaaatgccca SEQ ID NO 30: Mouse Ighg2b Hinge
gagcccagcgggcccatttcaacaatcaacccctgtcctccatgcaaggagtgtcacaaatgccca SEQ ID NO 31: Mouse Ighg2c Hinge
gagcccagagtgcccataacacagaacccctgtcctccactcaaagagtgtcccccatgcgca SEQ ID NO 32: Mouse Ighg3 Hinge
gagcctagaatacccaagcccagtacccccccaggttcttcatgcccac SEQ ID NO 33: Mouse Igha Hinge
ggtcctactcctcctcctcctattactattcct SEQ ID NO 34: Diphtheria toxin A (DTA) gene
gatgatgttgttgattcttctaaatcttttgtgatggaaaacttttcttcgtaccacgggactaaacctggttatgtag
attccattcaaaaaggtatacaaaagccaaaatctggtacacaaggaaattatgacgatgattggaaagggttttatag
taccgacaataaatacgacgctgcgggatactctgtagataatgaaaacccgctctctggaaaagctggaggcgtggtc
aaagtgacgtatccaggactgacgaaggttctcgcactaaaagtggataatgccgaaactattaagaaagagttaggtt
taagtctcactgaaccgttgatggagcaagtcggaacggaagagtttatcaaaaggttcggtgatggtgcttcgcgtgt
agtgctcagccttcccttcgctgaggggagttctagcgttgaatatattaataactgggaacaggcgaaagcgttaagc
gtagaacttgagattaattttgaaacccgtggaaaacgtggccaagatgcgatgtatgagtatatggctcaagcctgtg
caggaaatcgtgtcaggcga SEQ ID No 35: Linker 1 repeat sequence
GlyGlyGlyGlySer Fig. 16 (continued)

SEQ ID NO 36: mouse Cλ1 coding sequence
ggccagcccaagtcttcgccatcagtcaccctgtttccaccttcctctgaagagctcgagactaacaaggccacactgg
tgtgtacgatcactgatttctacccaggtgtggtgacagtggactggaaggtagatggtacccctgtcactcagggtat
ggagacaacccagccttccaaacagagcaacaacaagtacatggctagcagctacctgaccctgacagcaagagcatgg
gaaaggcatagcagttacagctgccaggtcactcatgaaggtcacactgtggagaagagtttgtcccgtgctgactgtt
cc SEQ ID NO 37: mouse Cλ2 coding sequence
ggtcagcccaagtccactcccactctcaccgtgtttccaccttcctctgaggagctcaaggaaaacaaagccacactgg
tgtgtctgatttccaacttttccccgagtggtgtgacagtggcctggaaggcaaatggtacacctatcacccagggtgt
ggacacttcaaatcccaccaaagagggcaacaagttcatggccagcagcttcctacatttgacatcggaccagtggaga
tctcacaacagttttacctgtcaagttacacatgaaggggacactgtggagaagagtctgtctcctgcagaatgtctc SEQ ID NO 38: mouse Cλ3 coding sequence
gtcagcccaagtccactcccacactcaccatgtttccaccttcccctgaggagctccaggaaaacaaagccacactcgt
gtgtctgatttccaattttccccaagtggtgtgacagtggcctggaaggcaaatggtacacctatcacccagggtgtg
gacacttcaaatcccaccaaagaggacaacaagtacatggccagcagcttcttacatttgacatcggaccagtggagat
ctcacaacagttttacctgccaagttacacatgaaggggacactgtggagaagagtctgtctcctgcagaatgtct SEQ ID NO 39: amino acid sequence of human Cκ
ArgThrValAlaAlaProSerValPheIlePheProProSerAspGluGlnLeuLysSerGlyThrAlaSerValValC
ysLeuLeuAsnAsnPheTyrProArgGluAlaLysValGlnTrpLysValAspAsnAlaLeuGlnSerGlyAsnSerGl
nGluSerValThrGluGlnAspSerLysAspSerThrTyrSerLeuSerSerThrLeuThrLeuSerLysAlaAspTyr
GluLysHisLysValTyrAlaCysGluValThrHisGlnGlyLeuSerSerProValThrLysSerPheAsnArgGlyG
luCys SEQ ID NO 40: amino acid sequence of human Cλ1
GlnProLysAlaAsnProThrValThrLeuPheProProSerSerGluGluLeuGlnAlaAsnLysAlaThrLeuValC
ysLeuIleSerAspPheTyrProGlyAlaValThrValAlaTrpLysAlaAspGlySerProValLysAlaGlyValGl
uThrThrLysProSerLysGlnSerAsnAsnLysTyrAlaAlaSerSerTyrLeuSerLeuThrProGluGlnTrpLys
SerHisArgSerTyrSerCysGlnValThrHisGluGlySerThrValGluLysThrValAlaProThrGluCysSer There are several Cλ1 alleles. The sequence shown is that of IMGT allele IGLC1*02.

SEQ ID NO 41: amino acid sequence of human Cλ2
GlnProLysAlaAlaProSerValThrLeuPheProProSerSerGluGluLeuGlnAlaAsnLysAlaThrLeuValC
ysLeuIleSerAspPheTyrProGlyAlaValThrValAlaTrpLysAlaAspSerSerProValLysAlaGlyValGl
uThrThrThrProSerLysGlnSerAsnAsnLysTyrAlaAlaSerSerTyrLeuSerLeuThrProGluGlnTrpLys
SerHisArgSerTyrSerCysGlnValThrHisGluGlySerThrValGluLysThrValAlaProThrGluCysSer There are several Cλ2 alleles. The sequence shown is that of IMGT allele IGLC2*02

SEQ ID NO 42: amino acid sequence of human Cλ3
GlnProLysAlaAlaProSerValThrLeuPheProProSerSerGluGluLeuGlnAlaAsnLysAlaThrLeuValC
ysLeuIleSerAspPheTyrProGlyAlaValThrValAlaTrpLysAlaAspSerSerProValLysAlaGlyValGl
uThrThrThrProSerLysGlnSerAsnAsnLysTyrAlaAlaSerSerTyrLeuSerLeuThrProGluGlnTrpLys
SerHisLysSerTyrSerCysGlnValThrHisGluGlySerThrValGluLysThrValAlaProThrGluCysSer There are several Cλ3 alleles. The sequence shown is that of IMGT allele IGLC3*03.

Fig. 16 (continued)

SEQ ID NO 43: amino acid sequence of human Cλ6
GlyGlnProLysAlaAlaProSerValThrLeuPheProProSerSerGluGluLeuGlnAlaAsnLysAlaThrLeuV
alCysLeuIleSerAspPheTyrProGlyAlaValLysValAlaTrpLysAlaAspGlySerProValAsnThrGlyVa
lGluThrThrThrProSerLysGlnSerAsnAsnLysTyrAlaAlaSerSerTyrLeuSerLeuThrProGluGlnTrp
LysSerHisArgSerTyrSerCysGlnValThrHisGluGlySerThrValGluLysThrValAlaProAlaGluCysS
er There are several Cλ6 alleles. The sequence shown is that of IMGT allele IGLC6*01.

SEQ ID NO 44: amino acid sequence of human Cλ7
GlyGlnProLysAlaAlaProSerValThrLeuPheProProSerSerGluGluLeuGlnAlaAsnLysAlaThrLeuV
alCysLeuValSerAspPheAsnProGlyAlaValThrValAlaTrpLysAlaAspGlySerProValLysValGlyVa
lGluThrThrLysProSerLysGlnSerAsnAsnLysTyrAlaAlaSerSerTyrLeuSerLeuThrProGluGlnTrp
LysSerHisArgSerTyrSerCysArgValThrHisGluGlySerThrValGluLysThrValAlaProAlaGluCysS
er There are several Cλ7 alleles. The sequence shown is that of IMGT allele IGLC7*03

SEQ ID NO 45-47: amino acid sequence of human IgG1 (IGHG1) constant (CH) domains
There are several IGHG1 alleles. The sequence shown is that of IMGT allele IGHG1*05.

SEQ ID NO 45: amino acid sequence of human IGHG1 CH1
AlaSerThrLysGlyProSerValPheProLeuAlaProSerSerLysSerThrSerGlyGlyThrAlaAlaLeuGlyC
ysLeuValLysAspTyrPheProGluProValThrValSerTrpAsnSerGlyAlaLeuThrSerGlyValHisThrPh
eProAlaValLeuGlnSerSerGlyLeuTyrSerLeuSerSerValValThrValProSerSerSerLeuGlyThrGln
ThrTyrIleCysAsnValAsnHisLysProSerAsnThrLysValAspLysLysVal SEQ ID NO 46: amino acid sequence of human IGHG1 CH2
ProCysProAlaProGluLeuLeuGlyGlyProSerValPheLeuPheProProLysProLysAspThrLeuMetIleS
erArgThrProGluValThrCysValValValAspValSerHisGluAspProGluValLysPheAsnTrpTyrValAs
pGlyValGluValHisAsnAlaLysThrLysProArgGluGluGlnTyrAsnSerThrTyrArgValValSerValLeu
ThrValLeuHisGlnAspTrpLeuAsnGlyLysGluTyrLysCysLysValSerAsnLysAlaLeuProAlaProIleG
luLysThrIleSerLysAlaLys SEQ ID NO 47: amino acid sequence of human IGHG1 CH3
GlyGlnProArgGluProGlnValTyrThrLeuProProSerArgAspGluLeuThrLysAsnGlnValSerLeuThrC
ysLeuValLysGlyPheTyrProSerAspIleAlaValGluTrpGluSerAsnGlyGlnProGluAsnAsnTyrLysTh
rThrProProValLeuAspSerAspGlySerPhePheLeuTyrSerLysLeuThrValAspLysSerArgTrpGlnGln
GlyAsnValPheSerCysSerValMetHisGluAlaLeuHisAsnHisTyrThrGlnLysSerLeuSerLeuSerProG
lyLys Fig. 16 (continued)

Figure 7A:
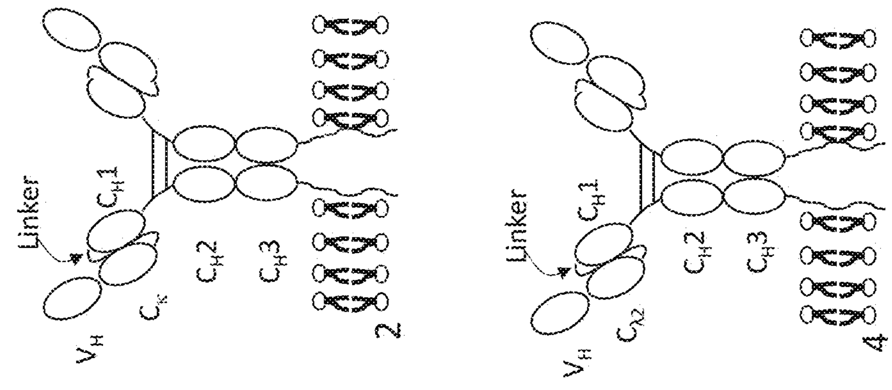
Figure 7A:
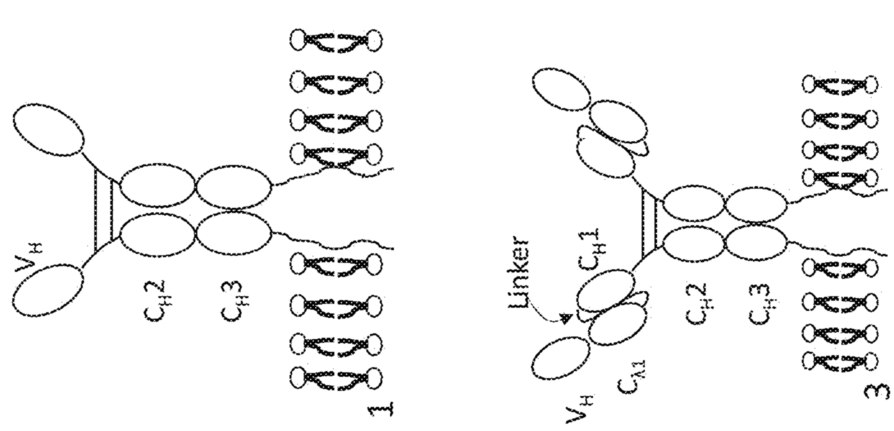

SEQ ID NO 48: nucleotide sequence of construct 3 in Figure 7.
atggagtttgggctgagctgggttttccttgttgctattataaaaggtgtccagtgtcaggtgcagctggtggagtctg
ggggaggcttggtcaagcctggagggtccctgagactctcctgtgcagcctctggattcaccttcagtgaccactacat
gagctggatccgccaggctccagggaaggggctggagtgggtttcatacattagtagtagtggtagtatcatatactac
gcagactctgtgaagggccgattcaccatctccagggacaacgccaagaactcactgtatctgcaaatgaacagcctga
gagccgaggacacggccgtgtattactgtgcgagaggcgtgccggcgaccgatagctggggccagggaaccctggtcac
cgtctcctcaggccagcccaagtcttcgccatcagtcaccctgtttccaccttcctctgaagagctcgagactaacaag
gccacactggtgtgtacgatcactgatttctacccaggtgtggtgacagtggactggaaggtagatggtacccctgtca
ctcagggtatggagacaacccagccttccaaacagagcaacaacaagtacatggctagcagctacctgaccctgacagc
aagagcatgggaaaggcatagcagttacagctgccaggtcactcatgaaggtcacactgtggagaagagtttgtcccgt
gctgactgttccggtggtggaggatccggtggaggggggatcaggaggaggcggtagtggggaggtggcagtggcggtg
gggatctggaggaggtgggtctggtggcggcgggtcaggcgggggcgggtcaggaggggggggttctggaggtggagg
gagcgctaaaacgacacccccatctgtctatccactggcccctggatctgctgcccaaactaactccatggtgaccctg
ggatgcctggtcaagggctatttccctgagccagtgacagtgacctggaactctggatccctgtccagcggtgtgcaca
ccttcccagctgtcctgcagtctgacctctacactctgagcagctcagtgactgtcccctccagcacctggcccagcca
gaccgtcacctgcaacgttgcccacccggccagcagcaccaaggtggacaagaaaattgtgcccagggattgtggttgt
aagccttgcatatgtacagtcccagaagtatcatctgtcttcatcttccccccaaagcccaaggatgtgctcaccatta
ctctgactcctaaggtcacgtgtgttgtggtagacatcagcaaggatgatcccgaggtccagttcagctggtttgtaga
tgatgtggaggtgcacacagctcagacgaaaccccgggaggagcagatcaacagcactttccgttcagtcagtgaactt
cccatcatgcaccaggactggctcaatggcaaggagttcaaatgcagggtcaacagtgcagctttccctgcccccatcg
agaaaaccatctccaaaaccaaaggcagaccgaaggctccacaggtgtacaccattccacctcccaaggagcagatggc
caaggataaagtcagtctgacctgcatgataacaaacttcttccctgaagacattactgtggagtggcagtggaatggg
cagccagcggagaactacaagaacactcagcccatcatggacacagatggctcttacttcgtctacagcaagctcaatg
tgcagaagagcaactgggaggcaggaaatactttcacctgctctgtgttacatgagggcctgcacaaccaccatactga
gaagagcctctcccactctcctgggctgcaactggacgagacctgtgctgaggcccaggacggggagctggacgggctc
tggacgaccatcaccatcttcatcagcctcttcctgctcagtgtgtgctacagcgctgctgtcacactcttcaaggtaa
agtggatcttctcctcggtggtggagctgaagcagacactggttcctgaatacaagaacatgattgggcaagcacccta
g Fig. 16 (continued)

SEQ ID NO 49: amino acid sequence of construct 3 in Figure 7.
MetGluPheGlyLeuSerTrpValPheLeuValAlaIleIleLysGlyValGlnCysGlnValGlnLeuValGluSerG
lyGlyGlyLeuValLysProGlyGlySerLeuArgLeuSerCysAlaAlaSerGlyPheThrPheSerAspHisTyrMe
tSerTrpIleArgGlnAlaProGlyLysGlyLeuGluTrpValSerTyrIleSerSerSerGlySerIleIleTyrTyr
AlaAspSerValLysGlyArgPheThrIleSerArgAspAsnAlaLysAsnSerLeuTyrLeuGlnMetAsnSerLeuA
rgAlaGluAspThrAlaValTyrTyrCysAlaArgGlyValProAlaThrAspSerTrpGlyGlnGlyThrLeuValTh
rValSerSerGlyGlnProLysSerSerProSerValThrLeuPheProProSerSerGluGluLeuGluThrAsnLys
AlaThrLeuValCysThrIleThrAspPheTyrProGlyValValThrValAspTrpLysValAspGlyThrProValT
hrGlnGlyMetGluThrThrGlnProSerLysGlnSerAsnAsnLysTyrMetAlaSerSerTyrLeuThrLeuThrAl
aArgAlaTrpGluArgHisSerSerTyrSerCysGlnValThrHisGluGlyHisThrValGluLysSerLeuSerArg
AlaAspCysSerGlyGlyGlyGlySerGlyGlyGlyGlySerGlyGlyGlyGlySerGlyGlyGlyGlySerGlyGlyG
lyGlySerGlyGlyGlyGlySerGlyGlyGlyGlySerGlyGlyGlyGlySerGlyGlyGlyGlySerGlyGlyGlyGl
ySerAlaLysThrThrProProSerValTyrProLeuAlaProGlySerAlaAlaGlnThrAsnSerMetValThrLeu
GlyCysLeuValLysGlyTyrPheProGluProValThrValThrTrpAsnSerGlySerLeuSerSerGlyValHisT
hrPheProAlaValLeuGlnSerAspLeuTyrThrLeuSerSerSerValThrValProSerSerThrTrpProSerGl
nThrValThrCysAsnValAlaHisProAlaSerSerThrLysValAspLysLysIleValProArgAspCysGlyCys
LysProCysIleCysThrValProGluValSerSerValPheIlePheProProLysProLysAspValLeuThrIleT
hrLeuThrProLysValThrCysValValValAspIleSerLysAspAspProGluValGlnPheSerTrpPheValAs
pAspValGluValHisThrAlaGlnThrLysProArgGluGluGlnIleAsnSerThrPheArgSerValSerGluLeu
ProIleMetHisGlnAspTrpLeuAsnGlyLysGluPheLysCysArgValAsnSerAlaAlaPheProAlaProIle
GluLysThrIleSerLysThrLysGlyArgProLysAlaProGlnValTyrThrIleProProProLysGluGlnMetA
laLysAspLysValSerLeuThrCysMetIleThrAsnPhePheProGluAspIleThrValGluTrpGlnTrpAsnGl
yGlnProAlaGluAsnTyrLysAsnThrGlnProIleMetAspThrAspGlySerTyrPheValTyrSerLysLeuAsn
ValGlnLysSerAsnTrpGluAlaGlyAsnThrPheThrCysSerValLeuHisGluGlyLeuHisAsnHisHisThrG
luLysSerLeuSerHisSerProGlyLeuGlnLeuAspGluThrCysAlaGluAlaGlnAspGlyGluLeuAspGlyLe
uTrpThrThrIleThrIlePheIleSerLeuPheLeuLeuSerValCysTyrSerAlaAlaValThrLeuPheLysVal
LysTrpIlePheSerSerValValGluLeuLysGlnThrLeuValProGluTyrLysAsnMetIleGlyGlnAlaPro

SEQUENCE LISTING

```
<160> NUMBER OF SEQ ID NOS: 49

<210> SEQ ID NO 1
<211> LENGTH: 2182
<212> TYPE: DNA
<213> ORGANISM: Artificial Sequence
<220> FEATURE:
<223> OTHER INFORMATION: PGK_TK_pA

<400> SEQUENCE: 1

agtcagcttc tgatggaatt agaacttggc aaaacaatac tgagaatgaa gtgtatgtgg     60

aacagaggct gctgatctcg ttcttcaggc tatgaaactg acacatttgg aaaccacagt    120

acttagaacc acaaagtggg aatcaagaga aaaacaatga tcccacgaga gatctataga    180

tctatagatc atgagtggga ggaatgagct ggcccttaat ttggttttgc ttgtttaaat    240

tatgatatcc aactatgaaa cattatcata aagcaatagt aaagagcctt cagtaaagag    300
```

caggcattta tctaatccca ccccaccccc acccccgtag ctccaatcct tccattcaaa 360
atgtaggtac tctgttctca cccttcttaa caaagtatga caggaaaaac ttccatttta 420
gtggacatct ttattgttta atagatcatc aatttctgca gacttacagg acggatcgat 480
cccctcagtt agcctccccc atctcccggg caaacgtgcg cgccaggtcg catatcgtcg 540
gtatggagcc gggggtggtg acgtgggtct ggaccatccc ggaggtaagt tgcagcaggg 600
cgtcccggca gccggcgggc gattggtcgt aatccaggat aaagacgtgc atggaacgga 660
ggcgtttggc caagacgtcc aaggcccagg caaacacgtt atacaggtcg ccgttggggg 720
ccagcaactc gggggcccga aacagggtaa ataacgtgtc ccgatatggg ggtcgtgggc 780
ccgcgttgct ctggggctcg gcaccctggg gcggcacggc cgtccccgaa agctgtcccc 840
agtcctcccg ccacgacccg ccgcactgca gataccgcac cgtattggca agtagcccgt 900
aaacgcggcg aatcgcagcc agcatagcca ggtccagccg ctcgccgggg cgctggcgtt 960
tggccaggcg gtcgatgtgt ctgtcctccg gaagggcccc aagcacgatg ttggtgccgg 1020
gcaaggtcgg cgggatgagg gccacgaacg ccagcacggc ctgggggtc atgctgccca 1080 taaggtaccg cgcggccggg tagcacagga gggcggcgat gggatggcgg tcgaagatga 1140
gggtgagggc cgggggcggg gcatgtgagc tcccagcctc ccccccgata tgaggagcca 1200
gaacggcgtc ggtcacggca taaggcatgc ccattgttat ctgggcgctt gtcattacca 1260
ccgccgcgtc cccggccgat atctcaccct ggtcgaggcg gtgttgtgtg gtgtagatgt 1320
tcgcgattgt ctcggaagcc cccagcaccc gccagtaagt catcggctcg ggtacgtaga 1380
cgatatcgtc gcgcgaaccc agggccacca gcagttgcgt ggtggtggtt ttccccatcc 1440
cgtggggacc gtctatataa acccgcagta gcgtgggcat ttctgctcc gggcggactt 1500 ccgtggcttc ttgctgccgg cgagggcgca acgccgtacg tcggttgcta tggccgcgag 1560
aacgcgcagc ctggtcgaac gcagacgcgt gttgatggcc ggggtacgag gccatgatgg 1620
caaggacggt gcattggctg caggtcgaaa ggcccggaga tgaggaagag gagaacagcg 1680
cggcagacgt gcgcttttga agcgtgcaga atgccgggcc tccggaggac cttcgggcgc 1740
ccgccccgcc cctgagcccg cccctgagcc cgcccccgga cccacccctt cccagcctct 1800
gagcccagaa agcgaaggag caaagctgct attggccgct gccccaaagg cctacccgct 1860
tccattgctc agcggtgctg tccatctgca cgagactagt gagacgtgct acttccattt 1920
gtcacgtcct gcacgacgcg agctgcgggg cgggggggaa cttcctgact aggggaggag 1980
tagaaggtgg cgcgaagggg ccaccaaaga acggagccgg ttggcgccta ccggtggatg 2040
tggaatgtgt gcgaggccag aggccacttg tgtagcgcca agtgcccagc ggggctgcta 2100
aagcgcatgc tccagactgc cttgggaaaa gcgcctcccc tacccggtag aattgacctg 2160
ccggggccct cgaatcctgc ag 2182

<210> SEQ ID NO 2
<211> LENGTH: 2508
<212> TYPE: DNA
<213> ORGANISM: Mus musculus

<400> SEQUENCE: 2
gggtctataa ttactctgat gtctaggacc agggggctca ggtcactcag gtcaggtgag 60
tcctgcatct ggggactgtg gggttcaggt ggcctaaggc aggatgtgga gagagtttta 120
gtataggaac agaggcagaa cagagactgt gctactggta cttcgatgtc tggggcacag 180
ggaccacggt caccgtctcc tcaggtaagc tggctttttt ctttctgcac attccattct 240

```
gaaacgggaa aagatattct cagatctccc catgtcaggc catctgccac actctgcatg    300
ctgcagaagc ttttctgtaa ggatagggtc ttcactccca ggaaaagagg cagtcagagg    360
ctagctgcct gtggaacagt gacaatcatg gaaaataggc atttacattg ttaggctaca    420
tgggtagatg ggtttttgta cacccactaa aggggtctat gatagtgtga ctactttgac    480
tactggggcc aaggcaccac tctcacagtc tcctcaggtg agtccttaca acctctctct    540
tctattcagc ttaaatagat tttactgcat ttgttggggg ggaaatgtgt gtatctgaat    600
ttcaggtcat gaaggactag ggacaccttg ggagtcagaa agggtcattg ggagccctgg    660
ctgacgcaga cagacatcct cagctcccat acttcatggc cagagattta tagggatcct    720
ggccagcatt gccgctaggt ccctctcttc tatgctttct ttgtccctca ctggcctcca    780
tctgagatca tcctggagcc ctagccaagg atcatttatt gtcaggggtc taatcattgt    840
tgtcacaatg tgcctggttt gcttactggg gccaagggac tctggtcact gtctctgcag    900
gtgagtccta acttctccca ttctaaatgc atgttggggg gattctgggc cttcaggacc    960
aagattctct gcaaacggga atcaagattc aaccccttg tcccaaagtt gagacatggg    1020
tctgggtcag ggactctctg cctgctggtc tgtggtgaca ttagaactga agtatgatga    1080
aggatctgcc agaactgaag cttgaagtct gaggcagaat cttgtccagg gtctatcgga    1140
ctcttgtgag aattaggggc tgacagttga tggtgacaat ttcagggtca gtgactgtct    1200
ggtttctctg aggtgaggct ggaatatagg tcaccttgaa gactaaagag ggtccaggg    1260
gcttctgcac aggcagggaa cagaatgtgg aacaatgact tgaatggttg attcttgtgt    1320
gacaccagga attggcataa tgtctgagtt gcccaggggt gattctagtc agactctggg    1380
gtttttgtcg ggtatagagg aaaaatccac tattgtgatt actatgctat ggactactgg    1440
ggtcaaggaa cctcagtcac cgtctcctca ggtaagaatg gcctctccag gtctttattt    1500
ttaacctttg ttatggagtt ttctgagcat tgcagactaa tcttggatat ttgtccctga    1560
gggagccggc tgagagaagt tgggaaataa actgtctagg gatctcagag cctttaggac    1620
agattatctc cacatctttg aaaaactaag aatctgtgtg atggtgttgg tggagtccct    1680
ggatgatggg atagggactt tggaggctca tttgaagaag atgctaaaac aatcctatgg    1740
ctggagggat agttggggct gtagttggag attttcagtt tttagaataa aagtattagt    1800
tgtggaatat acttcaggac cacctctgtg acagcattta tacagtatcc gatgcatagg    1860
gacaaagagt ggagtggggc actttcttta gatttgtgag gaatgttccg cactagattg    1920
tttaaaactt catttgttgg aaggagagct gtcttagtga ttgagtcaag ggagaaaggc    1980
atctagcctc ggtctcaaaa gggtagttgc tgtctagaga ggtctggtgg agcctgcaaa    2040
agtccagctt tcaaaggaac acagaagtat gtgtatggaa tattagaaga tgttgctttt    2100
actcttaagt tggttcctag gaaaaatagt taaatactgt gactttaaaa tgtgagaggg    2160
ttttcaagta ctcatttttt taaatgtcca aaattcttgt caatcagttt gaggtcttgt    2220
ttgtgtagaa ctgatattac ttaaagttta accgaggaat gggagtgagg ctctctcata    2280
acctattcag aactgacttt taacaataat aaattaagtt tcaaatattt ttaaatgaat    2340
tgagcaatgt tgagttggag tcaagatggc cgatcagaac cagaacacct gcagcagctg    2400
gcaggaagca ggtcatgtgg caaggctatt tggggaaggg aaaataaaac cactaggtaa    2460
acttgtagct gtggtttgaa gaagtggttt tgaaacactc tgtccagc                2508
```

<210> SEQ ID NO 3

```
<211> LENGTH: 19
<212> TYPE: DNA
<213> ORGANISM: Artificial Sequence
<220> FEATURE:
<223> OTHER INFORMATION: T3 promoter

<400> SEQUENCE: 3

cctttagtga gggttaatt                                                19


<210> SEQ ID NO 4
<211> LENGTH: 48
<212> TYPE: DNA
<213> ORGANISM: Artificial Sequence
<220> FEATURE:
<223> OTHER INFORMATION: 5' FRT site

<400> SEQUENCE: 4

gaagttccta ttccgaagtt cctattcttc aaaaggtata ggaacttc                48


<210> SEQ ID NO 5
<211> LENGTH: 2711
<212> TYPE: DNA
<213> ORGANISM: Artificial Sequence
<220> FEATURE:
<223> OTHER INFORMATION: CAG_PuroR_pA

<400> SEQUENCE: 5

tcattctggc ctccccctcc cccaaggtca ttctggcctc cccctccccc aaggtcattc     60

tggcctcccc ctccccccttg gccgcgcctc attctggcct cccccctcccc caaggcacac    120

aaaaaaccaa cacacagatc tattgaaaat aatgatcttt tattgatccg cgcctggatc    180

tcgaaccggt tcaggcaccg ggcttgcggg tcatgcacca ggtgcgcggt ccttcgggca    240

cctcgacgtc ggcggtgacg gtgaagccga gccgctcgta gaaggggagg ttgcggggcg    300

cggaggtctc caggaaggcg ggcaccccgg cgcgctcggc cgcctccact ccggggagca    360

cgacggcgct gcccagaccc ttgccctggt ggtcgggcga gacgccgacg gtggccagga    420

accacgcggg ctccttgggc cggtgcggcg ccaggaggcc ttccatctgt tgctgcgcgg    480

ccagccggga accgctcaac tcggccatgc gcgggccgat ctcggcgaac accgcccccg    540

cttcgacgct ctccggcgtg gtccagaccg ccaccgcggc gccgtcgtcc gcgacccaca    600

ccttgccgat gtcgagcccg acgcgcgtga ggaagagttc ttgcagctcg gtgacccgct    660

cgatgtggcg gtccgggtcg acggtgtggc gcgtggcggg gtagtcggcg aacgcggcgg    720

cgagggtgcg tacggcccgg gggacgtcgt cgcgggtggc gaggcgcacc gtgggcttgt    780

actcggtcat ggaaggctag gcggatcggc gatcgctccg gaggccgccc tgggagtgga    840

cacctgtgga gagaaaggca aagtggatgt caatgtcact caagtgtatg gccagatctc    900

aagcctgcca cacctcaagc ttgacaacaa aaagattgtc ttttctgacc agatggacgc    960

ggccaccctc aaaggcatca ccgcgggcca ggtgaatatc aaatcctcct cgtttttgga   1020

aactgacaat cttagcgcag aagtcatgcc cgcttttgag agggagtact caccccaacg   1080

cttctagagc cgccggtcac acgccagaag ccgaaccccg ccctgccccg tcccccccga   1140

aggcagccgt cccccccgcgg acagccccga ggctggagag ggagaagggg acggcggcgc   1200

ggcgacgcac gaaggccctc cccgcccatt tccttcctgc cggcgccgca ccgcttcgcc   1260

ccgcgcccgc tagaggggggt gcggcggcgc ctcccagatt tcggctccgc acagatttgg   1320

gacaaaggaa gtccctgcgc cctctcgcac gattaccata aaggcaatg gctgcggctc    1380

gccgcgcctc gacagccgcc ggcgctccgg gggccgccgc gcccctcccc cgagccctcc   1440
```

```
ccggcccgag gcggccccgc cccgcccggc acccccacct gccgccaccc cccgcccggc   1500

acggcgagcc ccgcgccacg ccccgtacgg agccccgcac ccgaagccgg gccgtgctca   1560

gcaactcggg gaggggggtg caggggggt tgcagcccga ccgacgcgcc cacacccccct   1620

gctcaccccc ccacgcacac accccgcacg cagcctttgt tcccctcgca gccccccccg   1680

caccgcgggg caccgccccc ggccgcgctc ccctcgcgca cactgcggag cgcacaaagc   1740

cccgcgccgc gcccgcagcg ctcacagccg ccgggcagcg cggagccgca cgcggcgctc   1800

cccacgcaca cacacacgca cgcacccccc gagccgctcc ccccgcacaa agggccctcc   1860

cggagcccct caaggctttc acgcagccac agaaaagaaa caagccgtca ttaaaccaag   1920

cgctaattac agcccggagg agaagggccg tcccgcccgc tcacctgtgg gagtaacgcg   1980

gtcagtcaga gccggggcgg gcggcgcgag gcggcggcgg agcggggcac ggggcgaagg   2040

cagcgcgcag cgactcccgc ccgccgcgcg cttcgctttt tatagggccg ccgccgccgc   2100

cgcctcgcca taaaaggaaa ctttcggagc gcgccgctct gattggctgc cgccgcacct   2160

ctccgcctcg ccccgccccg cccctcgccc cgccccgccc cgcctggcgc gcgccccccc   2220

ccccccgcc cccatcgctg cacaaaataa ttaaaaaata aataaataca aaattggggg   2280

tggggagggg ggggagatgg ggagagtgaa gcagaacgtg ggctcacct cgaccatggt   2340

aatagcgatg actaatacgt agatgtactg ccaagtagga aagtcccata aggtcatgta   2400

ctgggcataa tgccaggcgg gccatttacc gtcattgacg tcaatagggg gcgtacttgg   2460

catatgatac acttgatgta ctgccaagtg ggcagtttac cgtaaatact ccacccattg   2520

acgtcaatgg aaagtcccta ttggcgttac tatgggaaca tacgtcatta ttgacgtcaa   2580

tgggcggggg tcgttgggcg gtcagccagg cgggccattt accgtaagtt atgtaacgcg   2640

gaactccata tatgggctat gaactaatga ccccgtaatt gattactatt aataactagt   2700

caataatcaa t                                                        2711


<210> SEQ ID NO 6
<211> LENGTH: 48
<212> TYPE: DNA
<213> ORGANISM: Artificial Sequence
<220> FEATURE:
<223> OTHER INFORMATION: 3' FRT site

<400> SEQUENCE: 6

gaagttccta ttccgaagtt cctattcttc aaaaggtata ggaacttc                 48


<210> SEQ ID NO 7
<211> LENGTH: 313
<212> TYPE: DNA
<213> ORGANISM: Mus musculus

<400> SEQUENCE: 7

ctgcagcagc tggcaggaag caggtcatgt ggcaaggcta tttggggaag ggaaaataaa     60

accactaggt aaacttgtag ctgtggtttg aagaagtggt tttgaaacac tctgtccagc    120

cccaccaaac cgaaagtcca ggctgagcaa aacaccacct gggtaatttg catttctaaa    180

ataagttgag gattcagccg aaactggaga ggtcctcttt taacttattg agttcaacct    240

tttaatttta gcttgagtag ttctagtttc cccaaactta agtttatcga cttctaaaat    300

gtatttagaa ttc                                                       313


<210> SEQ ID NO 8
```

<211> LENGTH: 1000
<212> TYPE: DNA
<213> ORGANISM: Mus musculus

<400> SEQUENCE: 8

```
ttaaaaaaaa aaaaaaagga aagggacttc tctgtgtttg gcaacacaag tgcgatgcac     60
aggcaggaag atcaaatctg tcccaacaat acaggggaca gagggtcaac ctacaaaagg    120
aaagaacctg gggcagtgtg aagacaacac tgtagaagcc aaggctgagt tcactgagct    180
ctcgttagtg agactacaca gcaaggaggt ggcgggcact gagcagtgag gccccgggaa    240
gtgggggtga tggtggtgac ggtggtaact gttaagaact gggggaaaga attgtggaga    300
accaagctaa atagttatgt caaaccacat gtttaggagc ctgggttgac ttcataggga    360
gtaggcatgg aggctaatct agaggtttgt gtataggcaa gaagtgaatc ctgacccaag    420
aatagagagt gctaaacgga cttagttcaa agacaactga aaaagacaat gcctgcaaaa    480
caaagctaag gccagagctc ttggactatg aagagttcag ggaacctaag aacagggacc    540
atctgtgtac aggccaaggc cggtagaagc agcctaggaa gtgtcaagag ccaacgtggc    600
tgggtgggca aagacaggaa gggactgtta ggctgcaggg atgtgccgac ttcaatgtgc    660
ttcagtattg tccagattgt gtgcagccat atggcccagg tataagaggt ttaacagtgg    720
aacacagatg cccacatcag acagctgggg ggcgggggtg aacacagata cccatactgg    780
aaagcaggtg gggcattttc ctaggaacgg gactgggctc aatggcctca ggtctcatct    840
ggtctggtga tcctgacatt gataggccca aatgttggat atcacctact ccatgtagag    900
agtcggggac atgggaaggg tgcaaaagag cggccttcta gaaggtttgg tcctgtcctg    960
tcctgtctga cagtgtaatc acatatactt tttcttgtag                         1000
```

<210> SEQ ID NO 9
<211> LENGTH: 64
<212> TYPE: DNA
<213> ORGANISM: Mus musculus

<400> SEQUENCE: 9

```
ataatacact gaaatggagc ccttccttgt tacttcatac catcctctgt gcttccttcc     60
tcag                                                                  64
```

<210> SEQ ID NO 10
<211> LENGTH: 320
<212> TYPE: DNA
<213> ORGANISM: Mus musculus

<400> SEQUENCE: 10

```
gggctgatgc tgcaccaact gtatccatct tcccaccatc cagtgagcag ttaacatctg     60
gaggtgcctc agtcgtgtgc ttcttgaaca acttctaccc caaagacatc aatgtcaagt    120
ggaagattga tggcagtgaa cgacaaaatg gcgtcctgaa cagttggact gatcaggaca    180
gcaaagacag cacctacagc atgagcagca ccctcacgtt gaccaaggac gagtatgaac    240
gacataacag ctatacctgt gaggccactc acaagacatc aacttcaccc attgtcaaga    300
gcttcaacag gaatgagtgt                                                320
```

<210> SEQ ID NO 11
<211> LENGTH: 15
<212> TYPE: DNA
<213> ORGANISM: Artificial Sequence
<220> FEATURE:
<223> OTHER INFORMATION: Linker 2

<400> SEQUENCE: 11

```
ggaggagggg ggtcc                                                    15
```

<210> SEQ ID NO 12
<211> LENGTH: 289
<212> TYPE: DNA
<213> ORGANISM: Mus musculus

<400> SEQUENCE: 12

```
aaaacgacac ccccatctgt ctatccactg gcccctggat ctgctgccca aactaactcc     60

atggtgaccc tgggatgcct ggtcaagggc tatttccctg agccagtgac agtgacctgg    120

aactctggat ccctgtccag cggtgtgcac accttcccag ctgtcctgca gtctgacctc    180

tacactctga gcagctcagt gactgtcccc tccagcacct ggcccagcca gaccgtcacc    240

tgcaacgttg cccacccggc cagcagcacc aaggtggaca agaaaattg                289
```

<210> SEQ ID NO 13
<211> LENGTH: 96
<212> TYPE: PRT
<213> ORGANISM: Mus musculus

<400> SEQUENCE: 13

```
Lys Thr Thr Pro Pro Ser Val Tyr Pro Leu Ala Pro Gly Ser Ala Ala
1               5                   10                  15

Gln Thr Asn Ser Met Val Thr Leu Gly Cys Leu Val Lys Gly Tyr Phe
            20                  25                  30

Pro Glu Pro Val Thr Val Thr Trp Asn Ser Gly Ser Leu Ser Ser Gly
        35                  40                  45

Val His Thr Phe Pro Ala Val Leu Gln Ser Asp Leu Tyr Thr Leu Ser
    50                  55                  60

Ser Ser Val Thr Val Pro Ser Ser Thr Trp Pro Ser Gln Thr Val Thr
65                  70                  75                  80

Cys Asn Val Ala His Pro Ala Ser Ser Thr Lys Val Asp Lys Lys Ile
                85                  90                  95
```

<210> SEQ ID NO 14
<211> LENGTH: 39
<212> TYPE: DNA
<213> ORGANISM: Mus musculus

<400> SEQUENCE: 14

```
tgcccaggga ttgtggttgt aagccttgca tatgtacag                          39
```

<210> SEQ ID NO 15
<211> LENGTH: 321
<212> TYPE: DNA
<213> ORGANISM: Mus musculus

<400> SEQUENCE: 15

```
tcccagaagt atcatctgtc ttcatcttcc ccccaaagcc caaggatgtg ctcaccatta     60

ctctgactcc taaggtcacg tgtgttgtgg tagacatcag caaggatgat cccgaggtcc    120

agttcagctg gtttgtagat gatgtggagg tgcacacagc tcagacgaaa ccccgggagg    180

agcagatcaa cagcactttc cgttcagtca gtgaacttcc catcatgcac caggactggc    240

tcaatggcaa ggagttcaaa tgcagggtca acagtgcagc tttccctgcc cccatcgaga    300

aaaccatctc caaaaccaaa g                                              321
```

<210> SEQ ID NO 16
<211> LENGTH: 320
<212> TYPE: DNA
<213> ORGANISM: Mus musculus

<400> SEQUENCE: 16
gcagaccgaa ggctccacag gtgtacacca ttccacctcc caaggagcag atggccaagg 60
ataaagtcag tctgacctgc atgataacaa acttcttccc tgaagacatt actgtggagt 120
ggcagtggaa tgggcagcca gcggagaact acaagaacac tcagcccatc atggacacag 180
atggctctta cttcgtctac agcaagctca atgtgcagaa gagcaactgg gaggcaggaa 240
atactttcac ctgctctgtg ttacatgagg gcctgcacaa ccaccatact gagaagagcc 300
tctcccactc tcctggtaaa 320

<210> SEQ ID NO 17
<211> LENGTH: 132
<212> TYPE: DNA
<213> ORGANISM: Mus musculus

<400> SEQUENCE: 17
gggctgcaac tggacgagac ctgtgctgag gcccaggacg gggagctgga cgggctctgg 60
acgaccatca ccatcttcat cagcctcttc ctgctcagtg tgtgctacag cgctgctgtc 120
acactcttca ag 132

<210> SEQ ID NO 18
<211> LENGTH: 81
<212> TYPE: DNA
<213> ORGANISM: Mus musculus

<400> SEQUENCE: 18
gtaaagtgga tcttctcctc ggtggtggag ctgaagcaga cactggttcc tgaatacaag 60
aacatgattg ggcaagcacc c 81

<210> SEQ ID NO 19
<211> LENGTH: 1340
<212> TYPE: DNA
<213> ORGANISM: Mus musculus

<400> SEQUENCE: 19
taggccacct cctgtaatgg catttcccag gccccgaagg accctgtcca atatgccaag 60
cagcacaact gagatcacac tgtctgctca tctcgctttc ctccgacccc gagactcagc 120
tactctcaaa ttttccctct ctgaaggacc atgtggacat tacattgctc caggccacag 180
ccaccaggac ctaaaacacc atcacagcag caccaaagac actggataga cccacaaggg 240
caatagtttc ctcaacagta tatccaaact gttgggacaa acgagcaatc actgaagaag 300
tgacaagttc ccacaatgtc agtgtccagc tgagaaggga caaaaagtgg taccagccct 360
gtccacacca ccttctaatt cacaggaata cgtgatagaa gaggcaggtt gtagatccga 420
aagatgagac agattttatc aactccagaa agagctgggt ccaactgaat tattctagcg 480
accttggcat tgtcatgacc tgccatgacc ttcctcctta acacttcgat aaaccctggg 540
atatggaaaa tgcctgtgtt tctcagggtt tgggaaagaa ccatccatgt tgggattctt 600
gtgtagatcc tccttctggt cacagatgca atacactgga ttttcaggca aaggagcaaa 660
ttcacagaca actctggccc tacagcccta agacctagac accaccatct ccttggaatt 720
atcaaattta acacccggca cacaacaaag aaggactggg actttgaggc ctttgtgtag 780

```
ccctagaggg ggcagaggcc actgagcagg gattgggtga tcacaaggac ctcctggaga    840

gggacctgag gagcaggttc caattgggcc aaagaaagaa gaacaacaat agagatgaag    900

gatgctggaa agagccatgg tacagcagtc ttgtccttca gacatgactc ttacagccca    960

ggactcttac agtagctagc tggagcagaa gtccaaggga ttaccatgcc ctagggccac   1020

aggctactgg agggtggagt gagtctacta cacaggtcca atgcctgttt ctccattgct   1080

tctcagccaa tgagaaatca gagtctccac ctccaagaaa aaggaaggtg gaaatgaaag   1140

gtgagcacct gccttcccgt gactggcaga aagatctcca cggactcaag gctttgactt   1200

caaacttccc gtagatccct gatgtcttta aggactctgt ctgctttgtt ggttttgttt   1260

gtttgttttg tactttgtca ataaaacatt tttcaaatat tctacaattg ctgtgctctt   1320

cctatgcaaa ctggccctgg                                               1340


<210> SEQ ID NO 20
<211> LENGTH: 660
<212> TYPE: DNA
<213> ORGANISM: Mus musculus

<400> SEQUENCE: 20

cacttcaaaa catggcacag ttaagttgac cagtgggcca tgcagagcat actacccctc     60

ctggtcctgt gtcctaccag atatcctcta agtgtccctt cactgctggg ctccagttct    120

gctgccctga accacacagg tcctcagtct gtcctcccta tgggcagttt catcccagcc    180

agaagctgcc ctgtggcccc taggctgccc aggcatggtc tcccacacca accacacaaa    240

ctaagaagcc tgtcccatac attgacctca ggctcagtga taacatttct atagaaaaag    300

gaaaggaata agaaaaaaaa aactccatat tacatggggg ctgcctacct tgctgatgct    360

tattgtctca agcaagtttg gagaagttcc aaatcaggca ctgacagggt gggttctcag    420

ccatgctctt cttacctggt aggtgccttc tcccccatgg cacctcacag gctctccatc    480

tgtgtgtgtc tgggtcctga tctcttctca taagtacaaa gtcaggctgg aagaggtaca    540

ccctagccct cattataact taccagttta tgatcctgtc tgcaaacatc tgaggtccct    600

gtggctcaaa tgtcaattag tgagtcttct ggggacagaa tttagtccac attagctctc    660


<210> SEQ ID NO 21
<211> LENGTH: 4566
<212> TYPE: DNA
<213> ORGANISM: Mus musculus

<400> SEQUENCE: 21

ggtgttcatg cccctagagt tggctgaagg gccagatcca cctactctag aggcatctct     60

ccctgtctgt gaaggcttcc aaagtcacgt tcctgtggct agaaggcagc tccatagccc    120

tgctgcagtt tcgtcctgta taccaggttc acctactacc atatctagcc ctgcctgcct    180

taagagtagc aacaaggaaa tagcagggtg tagagggatc tcctgtctga caggaggcaa    240

gaagacagat tcttacccct ccatttctct tttatccctc tctggtcctc agagagtcag    300

tccttcccaa atgtcttccc cctcgtctcc tgcgagagcc ccctgtctga taagaatctg    360

gtggccatgg gctgcctggc ccgggacttc ctgcccagca ccatttcctt cacctggaac    420

taccagaaca acactgaagt catccagggt atcagaacct tcccaacact gaggacaggg    480

ggcaagtacc tagccacctc gcaggtgttg ctgtctccca agagcatcct tgaaggttca    540

gatgaatacc tggtatgcaa aatccactac ggaggcaaaa acaaagatct gcatgtgccc    600
```

```
attccaggta agaaccaaac cctcccagca ggggtgccca ggcccaggca tggcccagag    660
ggagcagcgg ggtggggctt aggccaagct gagctcacac cttgaccttt cattccagct    720
gtcgcagaga tgaaccccaa tgtaaatgtg ttcgtcccac cacgggatgg cttctctggc    780
cctgcaccac gcaagtctaa actcatctgc gaggccacga acttcactcc aaaaccgatc    840
acagtatcct ggctaaagga tgggaagctc gtggaatctg gcttcaccac agatccggtg    900
accatcgaga acaaaggatc cacaccccaa acctacaagg tcataagcac acttaccatc    960
tctgaaatcg actggctgaa cctgaatgtg tacacctgcc gtgtggatca caggggtctc   1020
accttcttga agaacgtgtc ctccacatgt gctgccagtg agtggcctgg gctaagccca   1080
atgcctagcc ctcccagatt agggaagtcc tcctacaatt atggccaatg ccacccagac   1140
atggtcattt gctccttgaa ctttggctcc ccagagtggc caaggacaag aatgagcaat   1200
aggcagtaga ggggtgagaa tcagctggaa ggaccagcat cttcccttaa gtaggtttgg   1260
gggatggaga ctaagctttt ttccaacttc acaactagat atgtcataac ctgacacagt   1320
gttctcttga ctgcaggtcc ctccacagac atcctaacct tcaccatccc cccctccttt   1380
gccgacatct tcctcagcaa gtccgctaac ctgacctgtc tggtctcaaa cctggcaacc   1440
tatgaaaccc tgaatatctc ctgggcttct caaagtggtg aaccactgga aaccaaaatt   1500
aaaatcatgg aaagccatcc caatggcacc ttcagtgcta agggtgtggc tagtgtttgt   1560
gtggaagact ggaataacag gaaggaattt gtgtgtactg tgactcacag ggatctgcct   1620
tcaccacaga agaaattcat ctcaaaaccc aatggtaggt atcccccctt cccttcccct   1680
ccaattgcag gacccttcct gtacctcata gggagggcag gtcctcttcc accctatcct   1740
cactactgtc ttcatttaca gaggtgcaca aacatccacc tgctgtgtac ctgctgccac   1800
cagctcgtga gcaactgaac ctgagggagt cagccacagt cacctgcctg gtgaagggct   1860
tctctcctgc agacatcagt gtgcagtggc ttcagagagg gcaactcttg ccccaagaga   1920
agtatgtgac cagtgccccg atgccagagc ctggggcccc aggcttctac tttacccaca   1980
gcatcctgac tgtgacagag gaggaatgga actccggaga gacctatacc tgtgttgtag   2040
gccacgaggc cctgccacac ctggtgaccg agaggaccgt ggacaagtcc actggtaaac   2100
ccacactgta caatgtctcc ctgatcatgt ctgacacagg cggcacctgc tattgaccat   2160
gctagcgctc aaccaggcag gccctgggtg tccagttgct ctgtgtatgc aaactaacca   2220
tgtcagagtg agatgttgca ttttataaaa attagaaata aaaaaaatcc attcaaacgt   2280
cactggtttt gattatacaa tgctcatgcc tgctgagaca gttgtgtttt gcttgctctg   2340
cacacaccct gcatacttgc ctccaccctg gcccttcctc taccttgcca gtttcctcct   2400
tgtgtgtgaa ctcagtcagg cttacaacag acagagtatg aacatgcgat tcctccagct   2460
acttctagat atatggctga aagcttgcct aacctggtgc aggcagcatt caggcacata   2520
tatagacaca catgcattta tacatagata tataggtaca catgtgtaga cacatacatg   2580
aatgtgtatt catggacaca cagacaaagg tacacatata tacacatgag ttcatgcgca   2640
cacacatgca tggacactta caaacgcctt cagagacaaa taggcataga cacacaacca   2700
ctcacagaaa cagataccaa tatgcatggt cctgtgtaca cagaaacaga ctataggcaa   2760
atatacacaa ataaactata tagatacaaa gatatgcata tacacacatg tacagaaaca   2820
tcttcacatg tgtacactaa catgtgaaca ggtatagcac acagatacac ctggactctg   2880
accagggctg taatctccaa ggctcacggc tcagagagcc tacactaggc tgggtcactg   2940
atactcctca ggagcccact ctatgattgg gagagataac cccaggtaca aagtatgcct   3000
```

```
atctgtctca acaccatggg gcagaagata ctccactaac cacccatgac agaaagttag   3060
ccttggctgt gtctccatta atagaacacc tcagaagacc aatgtgaaat tgcctaaccc   3120
actcacaccc accctgatct ccagttcaaa atgcagaaaa cataatgcag ttgtccaaaa   3180
gatgccccaa ccacacacac acacacacac acacacacac acacacacac acacacacac   3240
acacacacac accatcaagg agcctctgta aggagtcacc acccaataac actgcctctt   3300
tgggctcata tcctggacat tcttcatatt catatccatt tggggcctag gctttagata   3360
tccccaaggg ctcatcttta cagggatcag agatcccaat aaatgccctg gtcccacagc   3420
ctccctcagg tatctgtctg tttatctctt ggtaccaaga cccaacattg ctggcagggg   3480
taggacaagc aacgcacggg aactctgatc aaagaaagtc atgagatgcc tgagtccttc   3540
aggaagtaag gagggacaac ctctggtatc cctgttctta ttgctaaagc ccaagagaca   3600
gggagacctg ctctaaattc tcagtctaaa cagcaccgat ggcaccacct gctcagggaa   3660
agtccagagc acaccaatat cattttgcca cagttcctga gtctgccttt acccaggtcc   3720
atacattgca tctgtcttgc ttgctctgct gccccagggc tcctggaaca aaggctccaa   3780
attagtgtgt cctacagctt ggcctgttct gtgcctccgt ctagcttgag ctattagggg   3840
accagtcaat actcgctaag attctccaga accatcaggg caccccaacc cttatgcaaa   3900
tgctcagtca ccccaagact tggcttgacc ctccctctct gtgtcccttc atagaggggg   3960
aggtgaatgc tgaggaggaa ggctttgaga acctgtggac cactgcctcc accttcatcg   4020
tcctcttcct cctgagcctc ttctacagca ccaccgtcac cctgttcaag gtagtgtggt   4080
tgtggggctg aggacacagg gctgggacag ggagtcacca gtcctcactg cctctacctc   4140
tactccctac aagtggacag caattcacac tgtctctgtc acctgcaggt gaaatgactc   4200
tcagcatgga aggacagcag agaccaagag atcctcccac agggacacta cctctgggcc   4260
tgggatacct gactgtatga ctagtaaact tattcttacg tctttcctgt gttgccctcc   4320
agcttttatc tctgagatgg tcttctttct agactgacca aagacttttt gtcaacttgt   4380
acaatctgaa gcaatgtctg gcccacagac agctgagctg taaacaaatg tcacatggaa   4440
ataaatactt tatcttgtga actcacttta ttgtgaagga atttgttttg tttttcaaac   4500
ctttcctgcg gtgttgacag cccaaggatt atctgaatag agcttaggaa ctggaaatgg   4560
aacagt                                                              4566
```

<210> SEQ ID NO 22
<211> LENGTH: 45
<212> TYPE: DNA
<213> ORGANISM: Homo sapiens

<400> SEQUENCE: 22

```
gagcccaaat cttgtgacaa aactcacaca tgcccaccgt gccca                     45
```

<210> SEQ ID NO 23
<211> LENGTH: 36
<212> TYPE: DNA
<213> ORGANISM: Homo sapiens

<400> SEQUENCE: 23

```
gagcgcaaat gttgtgtcga gtgcccaccg tgccca                               36
```

<210> SEQ ID NO 24
<211> LENGTH: 51
<212> TYPE: DNA

<213> ORGANISM: Homo sapiens

<400> SEQUENCE: 24
gagctcaaaa ccccacttgg tgacacaact cacacatgcc cacggtgccc a 51

<210> SEQ ID NO 25
<211> LENGTH: 36
<212> TYPE: DNA
<213> ORGANISM: Homo sapiens

<400> SEQUENCE: 25
gagtccaaat atggtccccc atgcccatca tgccca 36

<210> SEQ ID NO 26
<211> LENGTH: 57
<212> TYPE: DNA
<213> ORGANISM: Homo sapiens

<400> SEQUENCE: 26
gttccctcaa ctccacctac cccatctccc tcaactccac ctaccccatc tccctca 57

<210> SEQ ID NO 27
<211> LENGTH: 18
<212> TYPE: DNA
<213> ORGANISM: Homo sapiens

<400> SEQUENCE: 27
gttcccccac ctccccca 18

<210> SEQ ID NO 28
<211> LENGTH: 39
<212> TYPE: DNA
<213> ORGANISM: Mus musculus

<400> SEQUENCE: 28
tgcccaggga ttgtggttgt aagccttgca tatgtacag 39

<210> SEQ ID NO 29
<211> LENGTH: 48
<212> TYPE: DNA
<213> ORGANISM: Mus musculus

<400> SEQUENCE: 29
gagcccagag ggcccacaat caagccctgt cctccatgca aatgccca 48

<210> SEQ ID NO 30
<211> LENGTH: 66
<212> TYPE: DNA
<213> ORGANISM: Mus musculus

<400> SEQUENCE: 30
gagcccagcg ggcccatttc aacaatcaac ccctgtcctc catgcaagga gtgtcacaaa 60
tgccca 66

<210> SEQ ID NO 31
<211> LENGTH: 63
<212> TYPE: DNA
<213> ORGANISM: Mus musculus

<400> SEQUENCE: 31
gagcccagag tgcccataac acagaacccc tgtcctccac tcaaagagtg tcccccatgc 60
gca 63

<210> SEQ ID NO 32
<211> LENGTH: 49
<212> TYPE: DNA
<213> ORGANISM: Mus musculus

<400> SEQUENCE: 32
gagcctagaa tacccaagcc cagtaccccc ccaggttctt catgcccac 49

<210> SEQ ID NO 33
<211> LENGTH: 33
<212> TYPE: DNA
<213> ORGANISM: Mus musculus

<400> SEQUENCE: 33
ggtcctactc ctcctcctcc tattactatt cct 33

<210> SEQ ID NO 34
<211> LENGTH: 573
<212> TYPE: DNA
<213> ORGANISM: Corynebacterium diphtheriae

<400> SEQUENCE: 34
gatgatgttg ttgattcttc taaatctttt gtgatggaaa acttttcttc gtaccacggg 60
actaaacctg gttatgtaga ttccattcaa aaaggtatac aaaagccaaa atctggtaca 120
caaggaaatt atgacgatga ttggaaaggg ttttatagta ccgacaataa atacgacgct 180
gcgggatact ctgtagataa tgaaaacccg ctctctggaa aagctggagg cgtggtcaaa 240
gtgacgtatc caggactgac gaaggttctc gcactaaaag tggataatgc cgaaactatt 300
aagaaagagt taggtttaag tctcactgaa ccgttgatgg agcaagtcgg aacggaagag 360
tttatcaaaa ggttcggtga tggtgcttcg cgtgtagtgc tcagccttcc cttcgctgag 420
gggagttcta gcgttgaata tattaataac tgggaacagg cgaaagcgtt aagcgtagaa 480
cttgagatta attttgaaac ccgtggaaaa cgtggccaag atgcgatgta tgagtatatg 540
gctcaagcct gtgcaggaaa tcgtgtcagg cga 573

<210> SEQ ID NO 35
<211> LENGTH: 5
<212> TYPE: PRT
<213> ORGANISM: Artificial Sequence
<220> FEATURE:
<223> OTHER INFORMATION: Linker

<400> SEQUENCE: 35

Gly Gly Gly Gly Ser
1 5

<210> SEQ ID NO 36
<211> LENGTH: 318
<212> TYPE: DNA
<213> ORGANISM: Mus musculus

<400> SEQUENCE: 36
ggccagccca agtcttcgcc atcagtcacc ctgtttccac cttcctctga agagctcgag 60
actaacaagg ccacactggt gtgtacgatc actgatttct acccaggtgt ggtgacagtg 120
gactggaagg tagatggtac ccctgtcact cagggtatgg agacaaccca gccttccaaa 180
cagagcaaca acaagtacat ggctagcagc tacctgaccc tgacagcaag agcatgggaa 240
aggcatagca gttacagctg ccaggtcact catgaaggtc acactgtgga gaagagtttg 300

```
tcccgtgctg actgttcc                                                318

<210> SEQ ID NO 37
<211> LENGTH: 315
<212> TYPE: DNA
<213> ORGANISM: Mus musculus

<400> SEQUENCE: 37

ggtcagccca agtccactcc cactctcacc gtgtttccac cttcctctga ggagctcaag   60

gaaaacaaag ccacactggt gtgtctgatt tccaactttt ccccgagtgg tgtgacagtg  120

gcctggaagg caaatggtac acctatcacc cagggtgtgg acacttcaaa tcccaccaaa  180

gagggcaaca agttcatggc cagcagcttc ctacatttga catcggacca gtggagatct  240

cacaacagtt ttacctgtca agttacacat gaaggggaca ctgtggagaa gagtctgtct  300

cctgcagaat gtctc                                                   315

<210> SEQ ID NO 38
<211> LENGTH: 313
<212> TYPE: DNA
<213> ORGANISM: Mus musculus

<400> SEQUENCE: 38

gtcagcccaa gtccactccc acactcacca tgtttccacc ttcccctgag gagctccagg   60

aaaacaaagc cacactcgtg tgtctgattt ccaatttttc cccaagtggt gtgacagtgg  120

cctggaaggc aaatggtaca cctatcaccc agggtgtgga cacttcaaat cccaccaaag  180

aggacaacaa gtacatggcc agcagcttct tacatttgac atcggaccag tggagatctc  240

acaacagttt tacctgccaa gttacacatg aaggggacac tgtggagaag agtctgtctc  300

ctgcagaatg tct                                                     313

<210> SEQ ID NO 39
<211> LENGTH: 107
<212> TYPE: PRT
<213> ORGANISM: Homo sapiens

<400> SEQUENCE: 39

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 40
<211> LENGTH: 105
<212> TYPE: PRT
<213> ORGANISM: Homo sapiens

<400> SEQUENCE: 40
```

```
Gln Pro Lys Ala Asn Pro Thr Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Gly Ser Pro Val
        35                  40                  45

Lys Ala Gly Val Glu Thr Thr Lys Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105
```

<210> SEQ ID NO 41
<211> LENGTH: 105
<212> TYPE: PRT
<213> ORGANISM: Homo sapiens

<400> SEQUENCE: 41

```
Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105
```

<210> SEQ ID NO 42
<211> LENGTH: 105
<212> TYPE: PRT
<213> ORGANISM: Homo sapiens

<400> SEQUENCE: 42

```
Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Lys Ser Tyr Ser Cys Gln Val Thr His Glu Gly Ser Thr Val Glu
                85                  90                  95

Lys Thr Val Ala Pro Thr Glu Cys Ser
            100                 105
```

<210> SEQ ID NO 43
<211> LENGTH: 106
<212> TYPE: PRT
<213> ORGANISM: Homo sapiens

<400> SEQUENCE: 43

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Lys Val Ala Trp Lys Ala Asp Gly Ser Pro
        35                  40                  45

Val Asn Thr Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Ala Glu Cys Ser
            100                 105
```

<210> SEQ ID NO 44
<211> LENGTH: 106
<212> TYPE: PRT
<213> ORGANISM: Homo sapiens

<400> SEQUENCE: 44

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
            20                  25                  30

Phe Asn Pro Gly Ala Val Thr Val Ala Trp Lys Ala Asp Gly Ser Pro
        35                  40                  45

Val Lys Val Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
                85                  90                  95

Glu Lys Thr Val Ala Pro Ala Glu Cys Ser
            100                 105
```

<210> SEQ ID NO 45
<211> LENGTH: 98
<212> TYPE: PRT
<213> ORGANISM: Homo sapiens

<400> SEQUENCE: 45

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val


<210> SEQ ID NO 46
<211> LENGTH: 113
<212> TYPE: PRT
<213> ORGANISM: Homo sapiens

<400> SEQUENCE: 46

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys


<210> SEQ ID NO 47
<211> LENGTH: 107
<212> TYPE: PRT
<213> ORGANISM: Homo sapiens

<400> SEQUENCE: 47

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105


<210> SEQ ID NO 48
<211> LENGTH: 2055
<212> TYPE: DNA
<213> ORGANISM: Artificial Sequence
<220> FEATURE:
<223> OTHER INFORMATION: Construct

<400> SEQUENCE: 48

atggagtttg ggctgagctg ggttttcctt gttgctatta taaaaggtgt ccagtgtcag     60
```

```
gtgcagctgg tggagtctgg gggaggcttg gtcaagcctg gagggtccct gagactctcc    120
tgtgcagcct ctggattcac cttcagtgac cactacatga gctggatccg ccaggctcca    180
gggaaggggc tggagtgggt ttcatacatt agtagtagtg gtagtatcat atactacgca    240
gactctgtga agggccgatt caccatctcc agggacaacg ccaagaactc actgtatctg    300
caaatgaaca gcctgagagc cgaggacacg gccgtgtatt actgtgcgag aggcgtgccg    360
gcgaccgata gctggggcca gggaaccctg gtcaccgtct cctcaggcca gcccaagtct    420
tcgccatcag tcaccctgtt tccaccttcc tctgaagagc tcgagactaa caaggccaca    480
ctggtgtgta cgatcactga tttctaccca ggtgtggtga cagtggactg gaaggtagat    540
ggtacccctg tcactcaggg tatggagaca acccagcctt ccaaacagag caacaacaag    600
tacatggcta gcagctacct gaccctgaca gcaagagcat gggaaaggca tagcagttac    660
agctgccagg tcactcatga aggtcacact gtggagaaga gtttgtcccg tgctgactgt    720
tccggtggtg gaggatccgg tggaggggga tcaggaggag gcggtagtgg gggaggtggc    780
agtggcggtg gggggatctgg aggaggtggg tctggtggcg gcgggtcagg cgggggcggg    840
tcaggagggg ggggttctgg aggtggaggg agcgctaaaa cgacaccccc atctgtctat    900
ccactggccc ctggatctgc tgcccaaact aactccatgg tgaccctggg atgcctggtc    960
aagggctatt tccctgagcc agtgacagtg acctggaact ctggatccct gtccagcggt   1020
gtgcacacct tcccagctgt cctgcagtct gacctctaca ctctgagcag ctcagtgact   1080
gtcccctcca gcacctggcc cagccagacc gtcacctgca acgttgccca cccggccagc   1140
agcaccaagg tggacaagaa aattgtgccc agggattgtg gttgtaagcc ttgcatatgt   1200
acagtcccag aagtatcatc tgtcttcatc ttccccccaa agcccaagga tgtgctcacc   1260
attactctga ctcctaaggt cacgtgtgtt gtggtagaca tcagcaagga tgatcccgag   1320
gtccagttca gctggtttgt agatgatgtg gaggtgcaca cagctcagac gaaaccccgg   1380
gaggagcaga tcaacagcac tttccgttca gtcagtgaac ttcccatcat gcaccaggac   1440
tggctcaatg gcaaggagtt caaatgcagg gtcaacagtg cagctttccc tgcccccatc   1500
gagaaaacca tctccaaaac caaaggcaga ccgaaggctc cacaggtgta caccattcca   1560
cctcccaagg agcagatggc caaggataaa gtcagtctga cctgcatgat aacaaacttc   1620
ttccctgaag acattactgt ggagtggcag tggaatgggc agccagcgga gaactacaag   1680
aacactcagc ccatcatgga cacagatggc tcttacttcg tctacagcaa gctcaatgtg   1740
cagaagagca actgggaggc aggaaatact ttcacctgct ctgtgttaca tgagggcctg   1800
cacaaccacc atactgagaa gagcctctcc cactctcctg ggctgcaact ggacgagacc   1860
tgtgctgagg cccaggacgg ggagctggac gggctctgga cgaccatcac catcttcatc   1920
agcctcttcc tgctcagtgt gtgctacagc gctgctgtca cactcttcaa ggtaaagtgg   1980
atcttctcct cggtggtgga gctgaagcag acactggttc ctgaatacaa gaacatgatt   2040
gggcaagcac cctag                                                    2055
```

<210> SEQ ID NO 49
<211> LENGTH: 684
<212> TYPE: PRT
<213> ORGANISM: Artificial Sequence
<220> FEATURE:
<223> OTHER INFORMATION: Construct

<400> SEQUENCE: 49

-continued

```
Met Glu Phe Gly Leu Ser Trp Val Phe Leu Val Ala Ile Ile Lys Gly
1               5                   10                  15

Val Gln Cys Gln Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Asp His Tyr Met Ser Trp Ile Arg Gln Ala Pro Gly Lys Gly Leu
    50                  55                  60

Glu Trp Val Ser Tyr Ile Ser Ser Ser Gly Ser Ile Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Gly Val Pro Ala Thr Asp Ser Trp Gly Gln Gly
        115                 120                 125

Thr Leu Val Thr Val Ser Ser Gly Gln Pro Lys Ser Ser Pro Ser Val
    130                 135                 140

Thr Leu Phe Pro Pro Ser Ser Glu Glu Leu Glu Thr Asn Lys Ala Thr
145                 150                 155                 160

Leu Val Cys Thr Ile Thr Asp Phe Tyr Pro Gly Val Val Thr Val Asp
                165                 170                 175

Trp Lys Val Asp Gly Thr Pro Val Thr Gln Gly Met Glu Thr Thr Gln
            180                 185                 190

Pro Ser Lys Gln Ser Asn Asn Lys Tyr Met Ala Ser Ser Tyr Leu Thr
        195                 200                 205

Leu Thr Ala Arg Ala Trp Glu Arg His Ser Ser Tyr Ser Cys Gln Val
    210                 215                 220

Thr His Glu Gly His Thr Val Glu Lys Ser Leu Ser Arg Ala Asp Cys
225                 230                 235                 240

Ser Gly Gly Gly Gly Ser Gly Gly Gly Gly Ser Gly Gly Gly Gly Ser
                245                 250                 255

Gly Gly Gly Gly Ser Gly Gly Gly Gly Ser Gly Gly Gly Gly Ser Gly
            260                 265                 270

Gly Gly Gly Ser Gly Gly Gly Gly Ser Gly Gly Gly Gly Ser Gly Gly
        275                 280                 285

Gly Gly Ser Ala Lys Thr Thr Pro Pro Ser Val Tyr Pro Leu Ala Pro
    290                 295                 300

Gly Ser Ala Ala Gln Thr Asn Ser Met Val Thr Leu Gly Cys Leu Val
305                 310                 315                 320

Lys Gly Tyr Phe Pro Glu Pro Val Thr Val Thr Trp Asn Ser Gly Ser
                325                 330                 335

Leu Ser Ser Gly Val His Thr Phe Pro Ala Val Leu Gln Ser Asp Leu
            340                 345                 350

Tyr Thr Leu Ser Ser Ser Val Thr Val Pro Ser Ser Thr Trp Pro Ser
        355                 360                 365

Gln Thr Val Thr Cys Asn Val Ala His Pro Ala Ser Ser Thr Lys Val
    370                 375                 380

Asp Lys Lys Ile Val Pro Arg Asp Cys Gly Cys Lys Pro Cys Ile Cys
385                 390                 395                 400

Thr Val Pro Glu Val Ser Ser Val Phe Ile Phe Pro Pro Lys Pro Lys
                405                 410                 415

Asp Val Leu Thr Ile Thr Leu Thr Pro Lys Val Thr Cys Val Val Val
```

-continued

```
            420                 425                 430

Asp Ile Ser Lys Asp Asp Pro Glu Val Gln Phe Ser Trp Phe Val Asp
        435                 440                 445

Asp Val Glu Val His Thr Ala Gln Thr Lys Pro Arg Glu Glu Gln Ile
    450                 455                 460

Asn Ser Thr Phe Arg Ser Val Ser Glu Leu Pro Ile Met His Gln Asp
465                 470                 475                 480

Trp Leu Asn Gly Lys Glu Phe Lys Cys Arg Val Asn Ser Ala Ala Phe
                485                 490                 495

Pro Ala Pro Ile Glu Lys Thr Ile Ser Lys Thr Lys Gly Arg Pro Lys
            500                 505                 510

Ala Pro Gln Val Tyr Thr Ile Pro Pro Pro Lys Glu Gln Met Ala Lys
        515                 520                 525

Asp Lys Val Ser Leu Thr Cys Met Ile Thr Asn Phe Phe Pro Glu Asp
    530                 535                 540

Ile Thr Val Glu Trp Gln Trp Asn Gly Gln Pro Ala Glu Asn Tyr Lys
545                 550                 555                 560

Asn Thr Gln Pro Ile Met Asp Thr Asp Gly Ser Tyr Phe Val Tyr Ser
                565                 570                 575

Lys Leu Asn Val Gln Lys Ser Asn Trp Glu Ala Gly Asn Thr Phe Thr
            580                 585                 590

Cys Ser Val Leu His Glu Gly Leu His Asn His His Thr Glu Lys Ser
        595                 600                 605

Leu Ser His Ser Pro Gly Leu Gln Leu Asp Glu Thr Cys Ala Glu Ala
    610                 615                 620

Gln Asp Gly Glu Leu Asp Gly Leu Trp Thr Thr Ile Thr Ile Phe Ile
625                 630                 635                 640

Ser Leu Phe Leu Leu Ser Val Cys Tyr Ser Ala Ala Val Thr Leu Phe
                645                 650                 655

Lys Val Lys Trp Ile Phe Ser Ser Val Val Glu Leu Lys Gln Thr Leu
            660                 665                 670

Val Pro Glu Tyr Lys Asn Met Ile Gly Gln Ala Pro
        675                 680
```

SINGLE CHAIN VH AND HEAVY CHAIN ANTIBODIES

SEQUENCE LISTING

The instant application contains a Sequence Listing which has been submitted electronically in ASCII format and is hereby incorporated by reference in its entirety. The ASCII copy, created on Jun. 8, 2022, is named 0202-TR01US2_SL and is 47,799 bytes in size.

FIELD OF THE INVENTION

The invention relates to single chain VH antibody (scVHAb) constructs, heavy chain only antibody comprising such constructs, and methods of producing the same in vitro and in vivo.

BACKGROUND OF THE INVENTION

Antibodies have emerged as important biological pharmaceuticals because they (i) exhibit exquisite binding properties that can target antigens of diverse molecular forms, (ii) are physiological molecules with desirable pharmacokinetics that make them well tolerated in treated humans and animals, and (iii) are associated with powerful immunological properties that naturally ward off infectious agents. Furthermore, established technologies exist for the rapid isolation of antibodies from laboratory animals, which can readily mount a specific antibody response against virtually any foreign substance not present natively in the body.

In their most elemental form, antibodies are composed of two identical heavy (H) chains that are each paired with an identical light (L) chain. The N-termini of both H and L chains consist of a variable domain (VH and VL, respectively) that together provide the paired H-L chains with a unique antigen-binding specificity. The exons that encode the antibody VH and VL domains do not exist in the germ-line DNA. Instead, each VH exon is generated by the recombination of randomly selected V, D, and J gene segments present in the H chain locus (Igh); likewise, individual VL exons are produced by the chromosomal rearrangements of randomly selected V and J gene segments in a light chain locus (Igl) (see schematic of the mouse Igh locus, Igl kappa locus (Igk or Igκ) and Ig lambda locus (Igl or Igλ) in FIG. 1) (Tonegawa, Nature, 302:575, 1983; Bassing, et al., Cell, 109 Suppl:S45, 2002). The mouse genome contains two alleles that can express the H chain (one allele from each parent), two alleles that can express the kappa (κ) L chain, and two alleles that can express the lambda (λ) L chain. There are multiple V, D, and J gene segments at the H chain locus as well as multiple V and J genes at both L chain loci. Downstream of the J genes at each immunoglobulin (Ig) locus exist one or more exons that encode the constant region (C) of the antibody. In the heavy chain locus, exons for the expression of different antibody classes (isotypes) also exist. In mice, the encoded isotypes are IgM, IgD, IgG1, IgG2a/c, IgG2b, IgG3, IgE, and IgA; in humans they are IgM, IgD, IgG1, IgG2, IgG3, IgG4, IgE, IgA1, and IgA2.

During B cell development, gene rearrangements occur first on one of the two homologous chromosomes that contain the H chain V, D, and J gene segments. In pre-B cells, the resultant VH exon is then spliced at the RNA level to the exons that encode the constant region of the μH chain. Most of the pH chain synthesized by pre-B cells is retained in the endoplasmic reticulum (ER) and eventually degraded due to the non-covalent interaction between the μH chain partially unfolded CH1 domain and the resident ER chaperone BiP (Haas and Wabl, Nature, 306:387-9, 1983; Bole, et al., J Cell Biol. 102:1558, 1986). However, a small fraction of the μ chains associates with the surrogate light chain complex, composed of invariant λ5 and VpreB proteins, displacing BiP and allowing the μH chain/λ5/VpreB complex, together with Iga/P signaling molecules, to exit the ER as the preB Cell Receptor (preBCR) and traffic through the secretory pathway to the plasma membrane (Übelhart, et al., Curr. Top. Microbiol. Immunol. 393:3, 2016).

Subsequently, VJ rearrangements occur on one L chain allele at a time until a functional L chain is produced, after which the L chain polypeptides can completely displace BiP and associate with the μH chains to form a fully functional B cell receptor for antigen (BCR).

The ER quality control mechanisms that prevent cell surface expression or secretion of incompletely assembled Ig molecules are quite stringent, thus molecules such as HL, HHL, or HH are normally retained in the ER and degraded if not rescued by assembly into complete H2L2 structures. (The system is mainly focused on retention of Ig H chains; thus, free L chains can often be secreted.) However, it has been known for decades that free monoclonal H chains can be secreted in a rare B cell proliferative disorder called heavy chain disease (HCD) (Franklin, et al., Am. J. Med., 37:332, 1964). The H chains in HCD are truncated, and subsequent structural studies showed that CH1 domains are almost always deleted (Corcos, et al., Blood, 117:6991, 2011). Mechanistically, CH1 deletion frees the H chain from its restraining interaction with BiP, thus allowing its secretion, and also prevents disulfide bond-mediated covalent association with L chains, thus the HCD proteins are HH dimers. Heavy chain only Abs (HCAbs) can also be found in non-disease contexts. i) Approximately 75% of serum IgG in normal camels consists of HCAbs, which lack a CH1 domain and also have structurally altered VH domains that prevent effective association with VL domains (de los Rios, et al., Cur. Opin. Struct. Biol., 33:27, 2015). ii) Mice in which both κ and λ L chain gene loci are inactivated still produce serum IgG, but production of this antibody requires errors in class switch recombination (CSR) that lead to deletion of the CH1 domain-encoding exon in the B cell DNA (Zou, et al., J. Exp. Med., 204:3271, 2007).

HCAbs are attractive as therapeutics since they are highly stable and smaller than conventional immunoglobulins. The VH antigen-binding portion of the molecule, unencumbered by the VL antigen binding portion, can recognize epitopes within pockets of protein structure, which include enzyme active sites and epitopes on viruses and G-coupled protein receptors that are otherwise inaccessible to conventional Abs. Camel-based HCAbs derived, e.g., from mice in which the endogenous VH genes have been replaced by camel VH genes and the CH1-encoding exons have been deleted, are a potential source of such antibodies. However, they have the disadvantage that the camel VH domains are immunogenic in humans and other animals where they might be used as therapeutics. Mice exist in which the endogenous VH genes have been replaced by their human counterparts and, in combination with inactivation of the κ and λ L chain loci, could be a source of HCAbs. However, production of such antibodies relies on relatively infrequent errors in CSR during an immune response and is thus not efficient.

WO2014/141192A2 discloses generation of heavy-chain only antibodies and transgenic non-human animals producing the same. Such antibodies lack the CH1 domain.

U.S. Pat. No. 8,754,287B2 discloses mice producing heavy-chain antibodies that lack the CH1 domain, and transgenic mice comprising a germline modification to delete the nucleic acid encoding a CH1 domain.

Expression of heavy-chain only antibodies with no associated light chains in $VJC_L$ knockout chicken is described by Schusser et al. (Eur. J. Immunol., 46:2137, 2016).

Klein et al. (Biochemistry, 18:1473, 1979) describe the interaction of isolated variable and constant domains of light chain with the Fd' fragment of immunoglobulin G.

There is a need for efficient and cost-effective methods to produce HCAbs antibodies for diagnostic and therapeutic use. More particularly, there is a need for small, rapidly breeding, animals capable of producing antigen-specific HCAbs. Such animals are useful for generating hybridomas capable of large-scale production of H chain-only monoclonal antibodies.

In accordance with the foregoing object, transgenic non-human animals are provided which are capable of producing HCAbs.

SUMMARY OF THE INVENTION

This summary is provided to introduce a selection of concepts in a simplified form that are further described below in the detailed description. This summary is not intended to identify key or essential features of the claimed subject matter, nor is it intended to be used to limit the scope of the claimed subject matter. Other features, details, utilities, and advantages of the claimed subject matter will be apparent from the following written detailed description, including those aspects illustrated in the accompanying drawings and defined in the appended claims.

It is the objective of the present invention to provide antibody constructs that can be easily produced, either in a transgenic animal or in an in vitro cell culture.

The object is solved by the subject of the present claims and as further described herein.

According to the invention there is provided a single chain VH antibody (scVHAb) comprising an antigen-binding part consisting of a VH domain and the immunoglobulin constant domains CL and CH1, in the order from N-terminus to C-terminus: VH-L1-CL-L2-CH1, wherein L1 and L2 are each, independently, peptidic linkers; and wherein CL is paired with CH1 through beta-sheet contact thereby obtaining a CL/CH1 dimer.

Specifically, the CL is either Cκ or Cλ, preferably wherein the Cλ is selected from the group consisting of Cλ1, Cλ2 and Cλ3, in particular comprising human sequences, such as depicted in FIG. 16. According to a further specific embodiment, the Cλ is selected from the group consisting of Cλ6 and Cλ7, in particular comprising human sequences, such as depicted in FIG. 16.

When producing antibodies in the mouse, typically the constant regions of H and L chains are of mouse origin (such as comprising CH1, and any one of Cλ1, Cλ2 or Cλ3 sequences) to better interact with the mouse immune system. After isolation of the respective mouse antibodies, the C regions can easily be humanized e.g., to comprise human CH1, and/or any one of human Cλ1, Cλ2, Cλ3, Cλ6 or Cλ7 sequences).

Specifically, the CL/CH1 dimer is formed by association of the antibody domains such as to form a pair of domains.

Specifically, the association of the CL domain to the CH1 domain is through covalent linkage, such as by linking the C-terminus of the CL domain to the N-terminus of the CH1 domain through C-N linkage, employing the linker L2. Specifically, the conformation of the CL/CH1 dimer is additionally stabilized through interaction of the side chains of amino acids e.g., through a connecting interface between the beta-strands of the beta sheets, and optionally linked to each other by one or more disulfide bonds.

Specifically, the CL/CH1 dimer comprises at least one interdomain disulfide bond. Specifically, the at least one interdomain disulfide bond is formed by reduction of the most C-terminal cysteines of each of the CL and CH1 domains to enable formation of the disulfide bond.

Specifically, the C-terminus of the VH domain is covalently linked to the N-terminus of the CL domain through C-N linkage, optionally employing the linker L1 to provide added flexibility to this region.

Specifically, the pair of CL/CH1 domains is further stabilized by at least one interdomain disulfide bond, preferably a disulfide bridge connecting Cys107 in Cκ (UniProtKB—P01837), or Cys105 in Cλ1 (UniProtKB—A0A0G2JE99), or Cys103 in Cλ2 (UniProtKB—P01844), or Cys103 in Cλ3 (UniProtKB—P01845), to Cys102 in the associated CH1 (UniProtKB—P01868). Any such interdomain disulfide bridge stabilizing the pair of CL/CH1 in the scVHAb is herein understood as an interdomain, intrachain disulfide bridge. Additional disulfide bridges may be engineered by introducing new Cys residues or any other thiol forming amino acid or amino acid analogue into positions thereby forming additional S-S bridge(s) upon an oxidation reaction.

The scVHAb is specifically characterized by an arrangement of VH, CL and CH1 antibody domains arranged similar to an Fab fragment, except that the VH is linked to the CL domain instead of the CH1 domain, and the CH1 and CL domains are additionally connected by a single-chain linker. Thereby, the CL domain is part of an antibody heavy chain. The scVHAb is specifically characterized by the lack of any light chain, in particular without a VL domain.

The structure of an exemplary scVHAb is illustrated in FIG. 2A.

Linkers may comprise: an acidic linker, a basic linker, and a structural motif, or combinations thereof.

According to a specific aspect, any one of or both of L1 and L2 are artificial peptides, preferably glycine and/or serine rich linkers.

According to a further specific aspect, any one of or both of L1 and L2 comprise or consist of a part of a natural antibody sequence, in particular of an amino- or carboxy-terminal sequence of an antibody domain, or a hinge region.

Specifically, L1 is a peptide linker with an amino acid sequence of 3-40 amino acids length, preferably consisting of a) a sequence of glycine and/or serine in any combination; or b) a VH framework sequence.

According to a specific embodiment, the scVHAb does not comprise a linker L1. Such scVHAb comprises the VH domain that is directly linked or covalently attached to the CL domain (i.e., VH-CL-L2-CH1).

Specifically, L1 comprises a plurality of glycine and serine residues or consists of at least any of 3, 4, 5, 6, 7, 8, 9, 10, up to 40 consecutive amino acids, or a peptide of the same length comprising alternative amino acids.

Specifically, L2 is a peptide linker that is used as a tether to connect the pair of CL/CH1 domains. Exemplary L2 linkers consist of an amino acid sequence of 20 to 250, preferably 40 to 225, or 60 to 225 amino acids length, preferably consisting of a sequence of glycine and/or serine and/or arginine in any combination. An exemplary L2 linker is characterized by a repeat of a sequence, such as (GGAGGAGGGGGGTCC [SEQ ID NO:11])$_n$, wherein n=4-16.

In certain cases, L2 is an amino acid sequence of 15-90, specifically 20-80, more specifically 25-50 or 25-40 amino acids length, preferably consisting of a sequence of glycine and/or serine in any combination. Specifically, L2 comprises a plurality of glycine and serine residues or consists of at least any of 20, 25, 26, 27, 28, 29, 30, 31, 32, 33, 34, 35, 40, up to 80 consecutive amino acids, or a peptide of the same length comprising alternative amino acids.

Specifically, a peptide linker described herein comprises or consists of a serine and glycine rich amino acid sequence, preferably wherein each of the amino acids is a serine or glycine, more preferably wherein the peptide linker consists of repeats of serine and glycine residues, e.g., (GlyGlyGlyGlySer [SEQ ID NO:35])$_n$, wherein n=2-16. Typically, 6-10 repeats are used to stabilize the structure of the CL/CH1 domains paired in such a way as to support a contact surface in the beta sheet regions of the domains.

For example, any of the following sequences are suitably used as the peptide linker L1: (GlyGlyGlyGlySer [SEQ ID NO:35])$_n$, wherein n=1-8.

For example, any of the following sequences are suitably used as the peptide linker L2: (GlyGlyGlyGlySer [SEQ ID NO:35])$_n$, wherein n=4-16.

Specifically, the VH comprises an affinity matured antigen-binding site or a naïve conformation of VH-CDR sequences.

The antigen-binding part specifically comprises or consists of the three CDR loops of the VH domain, i.e., VH-CDR1, VH-CDR2, and VH-CDR3. The antigen-binding part can be affinity matured by variation of one or more of the CDR loops thereby optimizing or increasing affinity of binding a target antigen. Such variation can be obtained by one or more point mutations, e.g., 1, 2, 3 or more point mutations in any or each of the CDR sequences to obtain the affinity matured antigen binding site, e.g., by in vivo processes, or by in vitro mutagenesis techniques.

Antibodies produced by a transgenic non-human animal, are commonly understood as natural or native antibodies. Such natural antibodies can derive from the naïve repertoire or undergo affinity maturation in vivo resulting in high affinity antibodies that bind a specific target antigen, e.g., with a $K_D$ of less than $10^{-7}$ M, e.g., between $10^{-7}$ and $10^{-10}$ M.

Affinity matured antibodies produced by in vitro mutagenesis methods, such as employing random mutagenesis and/or library techniques, can result in even higher affinities, e.g., with a $K_D$ of less than $10^{-8}$ M, e.g., less than $10^{-11}$ M.

Natural antibodies advantageously are characterized by a native conformation of VH-CDR sequences. Such native conformation is characterized by a naturally-occurring primary structure of the antigen-binding site, and/or the naturally-occurring primary structure of the full-length VH domain.

The native conformation of a VH domain can be produced in vivo, e.g., upon mutating CDR sequences of a parent VH domain, or by producing variants of a parent VH domain, using artificial antibody display systems and respective libraries containing artificial antibody sequences, which can be selected to produce suitable antibodies.

According to a specific aspect, the C-terminus of the antigen-binding part of a scVHAb is fused to further immunoglobulin constant domains, with or without a hinge region.

Specifically, the further immunoglobulin domains comprise, in the order from N-terminus to C-terminus, at least CH2-CH3.

Specifically, the single chain construct comprises the extended scVHAb consisting of VH-L1-CL-L2-CH1-hinge-CH2-CH3, in the order from N-terminus to C-terminus.

The invention further provides for a heavy chain antibody (HCAb) comprising two extended scVHAbs, wherein the CH2-CH3 domains of a first extended scVHAb are paired with the CH2-CH3 domains of a second extended scVHAb, thereby obtaining an Fc region.

The Fc region described herein specifically comprises the constant region of an antibody excluding the first constant region immunoglobulin domain. Thus "Fc region" refers to the last two constant region immunoglobulin domains of IgA, IgD, and IgG, and the flexible hinge N-terminal to these domains, and the last three constant region immunoglobulin domains of IgE and IgM. For IgG, Fc comprises immunoglobulin domains CH2 and CH3 (Cγ2 and Cγ3) and the hinge between CH1 (Cγ1) and CH2 (Cγ2). The Fc region may also comprise a CH2 or CH3 domain in the form of an artificial variant of a respective naturally occurring antibody domain, e.g., with at least 90% sequence identity to said naturally occurring antibody domain.

In particular, the Fc region described herein comprises or consists of a dimer of CH2 and CH3 domains which domains are part of an antibody heavy chain (HC), wherein the CH2 domain of a first HC is paired with the CH2 of a second HC, and the CH3 domain of the first HC is paired with the CH3 of the second HC. Such dimer may be a homodimer, i.e., composed of two CH2-CH3 domain chains of the same amino acid sequence, or a heterodimer, i.e., composed of two CH2-CH3 domain chains, wherein each has a different amino acid sequence, e.g., with different CH3 amino acid sequences for stabilizing the Fc.

Specifically, the hinge region is originating from an antibody heavy chain hinge region linking the C-terminus of a CH1 domain to the N-terminus of a CH2 domain. Alternatively, any other natural or artificial linker of about the same length can be used. Suitable hinge regions are native IgG or IgA heavy chain hinge regions (SEQ ID NO:22-33), or functional variants thereof of the same length +/−1 or 2 amino acids, which optionally contain one or more, up to 5 or fewer point mutations.

For example, a hinge region originating from mouse antibodies may be used e.g., IgG1 (SEQ ID NO:28), IgG2a (SEQ ID NO:29), IgG2b (SEQ ID NO:30), IgG2c (SEQ ID NO:31), IgG3 (SEQ ID NO:32), or IgA (SEQ ID NO:33).

Alternatively, a human hinge region is suitably used, e.g., IgG1 (SEQ ID NO:22), IgG2 (SEQ ID NO:23), IgG3 (SEQ ID NO:24), IgG4 (SEQ ID NO:25), IgA1 (SEQ ID NO:26), or IgA2 (SEQ ID NO:27).

The hinge region typically comprises one or more cysteine residues to produce disulfide bridges in the HCAb. Specifically, if a mouse heavy chain hinge region of IgG1 is used, and the HCAb comprises the interchain disulfide bridges between the two hinge regions at Cys104, Cys107 and Cys109 (UniProtKB—P01868).

Specifically, the first and second extended scVHAbs are single chain constructs consisting of the following antibody domains and linking sequences: VH-L1-CL-L2-CH1-hinge-CH2-CH3, in the order from N-terminus to C-terminus.

The structure of an exemplary HCAb is illustrated in FIG. 2B.

The first and second extended scVHAbs in the HCAb may have the identical or a different amino acid sequence. For example, the first extended scVHAb comprises a first VH, and the second extended scVHAb comprises a second VH. The first and second VHs may comprise the same or different antigen-binding sites, e.g., specifically recognizing two different target antigens. Therefore, the HCAb can be monospecific and bivalent, or bispecific and monovalent.

When producing scVHAb or HCAb, selected domains and/or hinge regions are of human or non-human animal origin. For example, in a transgenic mouse, scVHAb or HCAb is preferably produced using one or more of the following: VH-CL-L2-CH1 for the scVHAb or VH-CL-L2-CH1-hinge-CH2-CH3 for the HCAb.

The VH exon in these cases is formed during VDJ rearrangement at the heavy chain locus in pre-B cells and will differ in individual B cells. For example, nucleotide sequences of the other elements are as follows: CL [Cκ (SEQ ID NO:10), Cλ1 (SEQ ID NO:36), Cλ2 (SEQ ID NO:37), or Cλ3 (SEQ ID NO:38)], L2 (4-16 repeats of the sequence identified as SEQ ID NO:11), CH1 (SEQ ID NO:12), hinge (SEQ ID NO:14), CH2 (SEQ ID NO:15), and CH3 (SEQ ID NO:16).

The nucleic acid sequences encoding the CL, CH1, CH2, or CH3 antibody domains are each of mouse origin. It is well understood that antibodies described herein can be prepared employing one or more of the respective sequences of other species, including e.g., of non-mouse animals, or of human origin, or any combination thereof, for example, the human nucleic acid sequences encoding the respective human antibody domains e.g., antibody domains comprising amino acid sequences as follows: CL [such as Cκ comprising SEQ ID NO:39, Cλ1 comprising SEQ ID NO:40, Cλ2 comprising SEQ ID NO:41, Cλ3 comprising SEQ ID NO:42, Cλ6 comprising SEQ ID NO:43, or Cλ7 comprising SEQ ID NO:44], IGHG1 CH1 comprising SEQ ID NO:45, IGHG1 CH2 comprising SEQ ID NO:46, and IGHG1 CH3 comprising SEQ ID NO:47.

It is well understood that any of the sequences of human antibody domains are exemplary only. Alternatively, sequences of human antibody domains of respective different alleles can be used.

As an alternative to the nucleotide sequences of animal or human origin encoding antibody domains, or the animal or human amino acid sequences, modified (artificial) nucleotide sequences and respective amino acid sequences may be used e.g., a respective sequence comprising at least 80% or at least 90% sequence identity, provided the respective antibody domain is functional to be paired and linked within the respective antibody structure as described herein.

According to a specific aspect, the scVHAb described herein or the HCAb described herein is provided in the soluble form, e.g., water-soluble form at concentrations suitably used in a pharmaceutical preparation. Specifically provided herein is a soluble preparation comprising the scVHAb described herein or the HCAb described herein, in the isolated form, such as isolated from serum or a blood fraction of an animal producing the same, or isolated from a cell culture fraction.

According to a specific aspect, the invention provides for the scVHAb described herein or the HCAb described herein, for medical use. Medical use encompasses treatment of human beings or veterinary use.

Accordingly, the invention provides for a method of treating a subject, e.g., a human being or a non-human mammal, for prophylaxis or therapy of a disease, which comprises administering to said subject an effective amount of said scVHAb or HCAb.

According to a specific aspect, the invention provides for a nucleic acid molecule encoding the scVHAb described herein.

According to another specific aspect, the invention provides for nucleic acid molecules encoding the HCAb described herein.

According to a specific aspect, the invention provides for a repertoire of antibodies comprising the scVHAb described herein or the HCAb described herein, which repertoire comprises a diversity of antibodies, each specifically recognizing the same target antigen. Such repertoire is understood as an antibody library of the same antibody type or structure, wherein antibodies differ in their antigen-binding sites, e.g., to produce antibody variants of a parent antibody recognizing the same epitope, such as affinity matured or otherwise optimized antibody variants; or antibodies that specifically recognize a target antigen, but different epitopes of such target antigen.

Such repertoire can be suitably screened and individual library members can be selected according to desired structural or functional properties, to produce an antibody product.

According to a specific aspect, the invention provides for a repertoire of antibodies comprising the scVHAb described herein or the HCAb described herein, which repertoire comprises a diversity of antibodies, recognizing different target antigens. Such a repertoire is obtained by immunization with complex, multicomponent antigens such as viruses or bacteria which have many different target antigens, each of which has multiple epitopes.

According to a specific embodiment, the repertoire is understood as a naïve library of antibodies, also termed the pre-immune repertoire, which is expressed by mature but antigen-inexperienced B cells that have recently exited from the bone marrow, their site of generation.

The repertoire of antibodies described herein is specifically characterized by a diversity encompassing at least $10^2$ antibodies, preferably any of at least $10^5$, $\mathbf{10^6}$, or $10^7$, each characterized by a different antigen-binding site.

According to a specific aspect, the repertoire described herein is provided, wherein a) genes encoding said antibodies are derived from B cells of non-immune or immunized mice, or
b) the antibodies are secreted by mammalian plasmacytes, preferably of rodent origin, in particular of mouse origin.

Specifically, the repertoire is obtainable by cloning the genes encoding it from B cells or by secreting the antibodies by a variety of mammalian plasmacytes. Specifically, the antibodies secreted by mammalian plasmacytes are characterized by a glycosylation pattern that is characteristic of the species of origin of the mammalian plasmacytes. Most physiological antibody isotypes are secreted as dimers of H2L2 but IgA can be secreted as higher order dimers or trimers $(H2L2)_2$ and $(H2L2)_3$ and IgM can be secreted as a pentamer $(H2L2)_5$ or hexamer $(H2L2)_6$. Notably, however, the HCAbs described herein do not contain L chains.

Therefore, the invention further provides for a method of producing the antibodies described herein, and specifically the repertoire of antibodies described herein by engineering mammalian plasmacytes expressing and secreting such antibodies.

Specifically, the mammalian plasmacytes are of non-human animal origin, e.g., of mammalian, vertebrate origin, in particular, a rodent such as mouse, or rat; or rabbit, or of avian origin, such as chicken. Specifically, the mammalian plasmacytes originate from a rodent, preferably mouse.

According to a specific aspect, the invention provides for an immunoglobulin heavy chain locus comprising a) a variable heavy chain region comprising one or more of each of the VH, DH and JH gene segments, b) a constant heavy chain region comprising constant exons encoding the CL and CH1 domains, and c) linking regions, which regions are engineered to express the scVHAb described herein or the HCAb described herein.

Specifically, the regions are positioned within said locus, such that the exon encoding the L1-CL part and L2 is inserted 5' of the exon encoding the CH1 domain.

Specifically, the constant heavy chain region further comprises exons encoding the CH2 and CH3 domains.

Specifically, the locus is a recombinant locus, which is originating from an animal, yet comprising at least one exogenous element, e.g., one or more exogenous heavy chain regions, not natively associated with the regulatory elements of the locus.

Specifically, an expression vector is used, which upon transfection of a host cell recombines with the host cell genome and, following productive VDJ rearrangement, the encoded antibody is expressed and inserted into the plasma membrane and/or secreted by the host cell. Specifically, the vector comprises one or more exogenous or heterologous regulatory elements, such as a promoter operably linked to the antibody coding sequence, which regulatory elements are not natively associated with said antibody coding sequence.

According to a specific aspect, the invention provides for a recombinant host cell comprising the locus described herein.

According to a specific aspect, the invention provides for a host cell transfected with the locus described herein, or the vector described herein.

Specifically, the host cell comprises a non-functional endogenous kappa light chain locus, and a non-functional endogenous lambda light chain locus. The light chain loci are non-functional loci, e.g., modified for loss-of-function or completely deleted.

According to a specific aspect, the invention provides for a transgenic non-human animal comprising the locus described herein. Specifically, the transgenic non-human animal is a mammalian, such as a vertebrate, in particular, a rodent such as mouse, or rat; or rabbit, or a bird, such as chicken.

Preferably, the transgenic non-human animal is a rodent, preferably a mouse.

Specifically, the transgenic non-human animal is avian, and the animal is produced using primordial germ cells. Thus, the methods described herein may further comprise: isolating a primordial germ cell that comprises the introduced antibody coding regions and using said germ cell to generate a transgenic non-human animal that contains the replaced immunoglobulin locus.

Specifically, the transgenic non-human animal described herein comprises loss-of-function mutations (including e.g., silencing mutations or those which inactivate a certain locus or gene) within, or deletion of, any of the endogenous light chain loci, kappa or lambda, or both.

Specifically, the transgenic non-human animal carries modified immunoglobulin alleles or other transgenes in their genomes.

In a specific embodiment, the transgenic animals of the invention further comprise human immunoglobulin regions. For example, numerous methods have been developed for replacing endogenous mouse immunoglobulin regions with human immunoglobulin sequences to create partially- or fully-human antibodies for drug discovery purposes. Examples of such mice include those described in, e.g., U.S. Pat. Nos. 7,145,056; 7,064,244; 7,041,871; 6,673,986; 6,596,541; 6,570,061; 6,162,963; 6,130,364; 6,091,001; 6,023,010; 5,593,598; 5,877,397; 5,874,299; 5,814,318; 5,789,650; 5,661,016; 5,612,205; and 5,591,669.

In the particularly favored aspects, the transgenic animals of the invention comprise chimeric immunoglobulin segments as described in US Pub. No. 2013/0219535 by Wabl and Killeen. Such transgenic animals have a genome comprising an introduced partially human immunoglobulin region, where the introduced region comprising human variable region coding sequences and non-coding regulatory sequences based on the endogenous genome of the non-human vertebrate. Preferably, the transgenic cells and animals of the invention have genomes in which part or all of the endogenous immunoglobulin region is removed.

In another favored aspect, the genomic contents of animals are modified so that their B cells are capable of expressing more than one functional VH domain per cell, i.e., the cells produce bispecific antibodies, as described in WO2017035252A1.

According to a specific aspect, the invention provides for a method for generating a transgenic non-human animal comprising:

a) providing a non-human animal cell;

b) providing one or more vectors comprising exons encoding the scVHAb or the HCAb as described herein;

c) introducing said one or more vectors into said non-human animal cell;

d) incorporating said exons into the genome of said non-human animal cell, and selecting a transgenic cell wherein said exons have been integrated into the cellular genome of said non-human animal cell at a target site that is in the endogenous immunoglobulin heavy chain gene locus, 5' of the first CH exon in said endogenous immunoglobulin heavy chain gene locus; and e) utilizing said transgenic cell to create a transgenic non-human animal comprising said transgenic cell.

Specifically, the transgenic non-human animal expresses the scVHAb or the HCAb as described herein. Specifically, the transgenic non-human animal expresses only heavy-chain antibodies, and/or does not express any antibody constructs which include a VL domain.

Specifically, a marker is used to indicate the successful integration of said exons into the cellular genome. Specifically, the marker is a selectable marker, which is capable of expression in a host that allows for ease of selection of those hosts containing an introduced nucleic acid or vector.

Examples of selectable markers include, e.g., proteins that confer resistance to antimicrobial agents (e.g., puromycin, hygromycin, bleomycin, or chloramphenicol), proteins that confer a metabolic advantage, such as a nutritional advantage on the host cell, as well as proteins that confer a functional or phenotypic advantage (e.g., cell division) on a cell.

Specifically, the vector is introduced such that the coding nucleic acid sequence is inserted into the cell, by means capable of incorporation of a nucleic acid sequence into a eukaryotic cell wherein the nucleic acid sequence may be present in the cell transiently or may be incorporated into or stably integrated within the genome (in particular the chromosome) of the cell.

Specifically, said exons are integrated into the cellular genome of said non-human animal cell at a target site, by any methods of targeted recombination, e.g., by homologous recombination or by site-specific recombination techniques. Specifically, the CRISPR/Cas9 genome editing system may be used for targeted recombination (He, et al., Nuc. Acids Res., 44:e85, 2016).

Specifically, said non-human animal cell is an embryonic stem (ES) cell of a said non-human animal. In one aspect, the host cell utilized for replacement of the endogenous immunoglobulin genes is an ES cell, which is then utilized to create a transgenic mammal. Thus, specific methods described herein may further comprise: isolating an ES cell that comprises the introduced antibody coding regions and using said ES cell to generate a transgenic animal that contains the engineered or replaced immunoglobulin locus.

According to a specific embodiment, a method for generating a transgenic non-human animal is provided, comprising:

- a) providing a non-human animal cell and integrating a recombinase mediated cassette exchange (RMCE) target site flanked by recognition sequences for site-specific recombinases at a location 5' of the first CH exon of the endogenous immunoglobulin heavy chain gene locus;
- b) providing one or more vectors comprising exons encoding the scVHAb or the HCAb described herein, which exons are flanked by further recognition sites for a site-specific recombinase, and one or more markers to select for targeted integration of the vector into a cellular genome, wherein the further recognition sites are capable of recombining with said RMCE target site;
- c) introducing said one or more vectors and a site-specific recombinase recognizing said RCME target site and further recognition sites, into said non-human animal cell;
- d) incorporating said exons into the genome of said non-human animal cell, and selecting a transgenic cell wherein said exons have been integrated into the cellular genome of said non-human animal cell at said RMCE target site; and
- e) utilizing said transgenic cell to create a transgenic non-human animal comprising said transgenic cell.

Specifically, any of said recognition sites for a site-specific recombinase is a recombinase recognition site (e.g., Cre/lox, Flp-FRT, etc.), where the recombinase is capable of excising a DNA sequence between two of its recognition sites.

According to another specific embodiment, a method for generating a transgenic non-human animal is provided, comprising

- a) providing a non-human animal cell comprising a target site 5' of the first CH exon of the endogenous immunoglobulin heavy chain gene locus;
- b) providing one or more vectors comprising exons encoding the scVHAb or the HCAb described herein, which exons are flanked by DNA sequences homologous to said target site, and one or more markers to select for targeted homologous recombination of the vector into a cellular genome;
- c) introducing said one or more vectors into said non-human animal cell;
- d) incorporating said exons into the genome of said non-human animal cell, and selecting a transgenic cell wherein said exons have been integrated into the cellular genome of said non-human animal cell at said target site; and
- e) utilizing said transgenic cell to create a transgenic non-human animal comprising said transgenic cell.

Specifically, a homology targeting vector or "targeting vector" may be used, which is a vector comprising a nucleic acid encoding a targeting sequence, a site-specific recombination site, and optionally a selectable marker gene, which is used to modify an endogenous immunoglobulin region using homology-mediated recombination in a host cell. For example, a homology targeting vector can be used in the present invention to introduce a site-specific recombination site into particular region of a host cell genome.

According to a specific aspect, the invention provides for a method for producing an antibody, comprising:

- a) expressing a heterologous immunoglobulin heavy chain locus in a non-human animal, which locus comprises
  - i) a variable heavy chain region comprising one or more of each of the VH, DH and JH gene segments,
  - ii) a constant heavy chain region comprising constant exons encoding the CL and CH1 domains, and
  - iii) linking regions, which regions are engineered and positioned to express the scVHAb or the HCAb described herein, wherein the non-human animal does not express the endogenous kappa and/or lambda locus; and
- b) producing an antibody which is said scVHAb and said HCAb, respectively, or which comprises at least the VH domain of said scVHAb or said HCAb, respectively.

Specifically, the non-human animal comprises the locus of the invention and further described herein.

Specifically, the non-human animal is treated to incorporate the locus by suitable gene targeting techniques, e.g., directed homologous recombination, employing site-specific recombinase techniques, or CRISPR/Cas9 techniques.

Specifically, the non-human animal is the transgenic non-human animal of the invention and further described herein.

Specifically, the non-human animal does not express the endogenous kappa and/or lambda locus, because said endogenous kappa and/or lambda locus is deleted or silenced, or otherwise mutated for loss-of-function.

According to a specific embodiment, the method further comprises the step of immunizing the non-human animal with an antigen such that an immune response is elicited against that antigen resulting in the generation of affinity-matured specific monoclonal or polyclonal antibodies.

An antigen can be administered to the non-human animal in any convenient manner, with or without an adjuvant, and can be administered in accordance with a predetermined schedule.

After immunization, serum or milk from immunized animals can be fractionated for the purification of pharmaceutical grade polyclonal antibodies specific for the antigen. In the case of transgenic birds, antibodies can also be made by fractionating egg yolks. A concentrated, purified immunoglobulin fraction may be obtained by chromatography (affinity, ionic exchange, gel filtration, etc.), selective precipitation with salts such as ammonium sulfate, organic solvents such as ethanol, or polymers such as polyethylene glycol.

For making a monoclonal antibody, antibody-producing cells, e.g., spleen and/or lymph node cells, may be isolated from the immunized transgenic animal and used either in cell fusion with transformed cell lines for the production of hybridomas, or cDNAs encoding antibodies are cloned by standard molecular biology techniques and expressed in transfected cells. The procedures for making monoclonal antibodies are well established in the art.

Specifically, the method further comprises the steps of preparing hybridomas and the producing and screening antibody producing cells, in particular those that specifically recognize a target antigen.

Specifically, the method further comprises the step of isolating nucleic acid sequences from the immunized non-human animal for the production of specific antibodies, or fragments thereof, in particular antigen-binding fragments, in a cell culture. Such antibodies or antigen-binding fragments thereof are herein understood as hyperimmune antibodies.

According to a specific embodiment, the antibodies described herein are produced in a cell culture employing suitable production host cell lines. Specifically, the production employs bacterial, yeast, plant, insect, or mammalian cell culture. Specifically, the host cells are used upon recombination with the respective nucleic acid molecules encoding the antibodies described herein. In particular, any of the mammalian host cells are advantageously used: BHK, CHO, HeLa, HEK293, MDCK, NIH3T3, NSO, PER.C6, SP2/0 or VERO cells.

According to a specific aspect, the invention provides for the use of the transgenic non-human animal described herein for producing a scVHAb or HCAb antibody, or fragments thereof including the VH domain, and optionally for further producing an antibody comprising said VH domain.

According to a specific aspect, the invention provides for the use of the transgenic non-human animal described herein for producing a library, in particular a naïve library of scVHAb or HCAb antibodies, or fragments thereof including the VH domain, or a library of nucleic acid sequences encoding or expressing said naïve library.

Transgenic cells described herein may be used to produce expression libraries for identification of antibodies of interest, e.g., by cloning the genes encoding the antibodies from B cells, or by selecting plasma cells with defined specificity in engineered mice that express antibodies on the plasma cell membrane, e.g., as described in US20170226162A1. The present invention thus also includes antibody libraries produced using the cell technologies for identification of antigen-specific antibodies expressed by plasma cells.

Upon producing the scVHAb or the HCAb described herein, the VH domain or its antigen-binding site can be characterized by suitable techniques to engineer an antibody of any type, e.g., full-length antibodies or antigen-binding fragments thereof, or even single VH domain antibodies and antibody constructs comprising such single VH domain antibodies. For example, the amino acid sequence or the coding nucleotide sequence of the VH domain or its antigen-binding site can be determined and recombined with further sequences of an antibody construct, or other binding molecules incorporating such VH domain or its antigen-binding site.

Some exemplary embodiments provide transgenic animals of the invention, which are further comprising human immunoglobulin regions. For example, numerous methods have been developed for replacing endogenous mouse immunoglobulin regions with human immunoglobulin sequences to create partially- or fully-human antibodies for drug discovery purposes. Examples of such mice include those described in, for example, U.S. Pat. Nos. 7,145,056; 7,064,244; 7,041,871; 6,673,986; 6,596,541; 6,570,061; 6,162,963; 6,130,364; 6,091,001; 6,023,010; 5,593,598; 5,877,397; 5,874,299; 5,814,318; 5,789,650; 5,661,016; 5,612,205; and 5,591,669.

Some further exemplary embodiments provide transgenic animals of the invention, which are further comprising chimeric immunoglobulin segments as described in US Pub. No. 2013/0219535 by Wabl and Killeen. Such transgenic animals have a genome comprising an introduced partially human immunoglobulin region, where the introduced region comprising human variable region coding sequences and non-coding variable sequences based on the endogenous genome of the non-human vertebrate. Preferably, the transgenic cells and animals of the invention have genomes in which part or all of the endogenous immunoglobulin region is removed.

Some further exemplary embodiments provide transgenic animals of the invention, which are further comprising changes to the immunoglobulin heavy chain gene allow for production of bispecific antibodies e.g., as described in WO2017035252A1, US 20170058052 A1.

Other embodiments provide primary B cells, immortalized B cells, or hybridomas derived from the genetically modified animal.

Other embodiments include a part or whole immunoglobulin protein transcribed from the immunoglobulin heavy chain genes from the engineered portion of the genetically modified animal; and part or whole engineered immunoglobulin proteins derived from the cells of the genetically modified animal.

These and other aspects, objects and features of the invention are described in more detail below.

FIGURES

Figure 1:
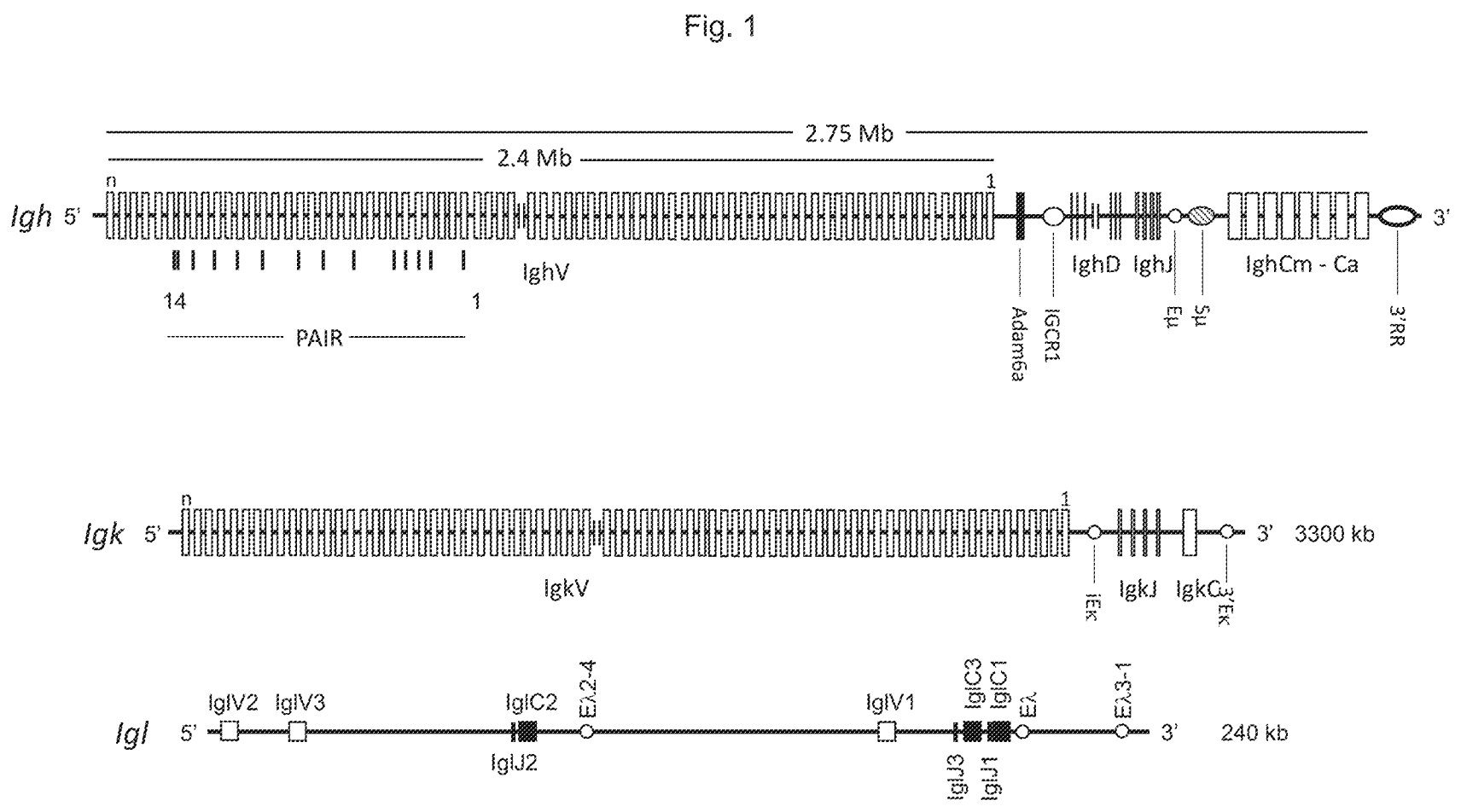

FIG. 1: Depicts the mouse Igh locus (top) [including V (IghV), D (IghD), J (IghJ), and C (IghC) gene segments; there are multiple IghC exons to encode the different Ig H chain isotypes], the Igκ locus (Igk, middle) [including V (IgkV), J (IgkJ), and C (IgkC) gene segments] and the Igλ locus (bottom) [including V (IglV), J (IglJ), and C (IglC) gene segments]. Also shown are (1) PAIR elements, which are cis-regulatory sequences critical for Igh looping to ensure utilization of distal VH gene segments in VDJ rearrangements, (2) the Adam6a male fertility-enabling gene, (3) Intergenic Control Region 1 (IGCR1), which contains sites that regulate ordered, lineage-specific rearrangement of the Igh locus, (4) Eμ, iEκ and Eλ2-4, the heavy, κ and λ light chain intronic enhancers, (5) 3'Eκ, Eλ and Eλ3-1, the κ and λ light chain 3' enhancers, (6) Sμ, the μ switch region, and (7) the 3' regulatory region (3'RR), a cis-acting element that controls isotype switching.

FIG. 2A: The transmembrane (TM) and secreted forms of the scVHAb. The TM form is expressed by B cells as an antigen receptor (BCR). The mature protein has the structure VH-L1 (optional)-CL-L2-CH1-TM; VH, heavy chain variable region, L1, Linker 1, CL, κ or λ light chain constant region, L2, Linker 2, CH1, heavy chain CH1 domain. The TM scVHAb is associated with Igα/β (CD79a/CD79b, not shown). The secreted form of the scVHAb is produced by plasmablasts and plasma cells and has essentially the same structure except that the 71 amino acid long TM region is replaced by a single lysine residue and the molecule is not associated with Igα/β. FIG. 2B: The TM and secreted forms of the HCAb. The TM form is expressed by B cells as a BCR. The mature protein has the structure VH-L1 (optional)-CL-L2-CH1-H-CH2-CH3-TM; H, heavy chain hinge region, CH2, heavy chain CH2 domain, CH3, heavy chain CH3 domain. The TM HCAb is also associated with Igα/β (CD79a/CD79b, not shown). The secreted form of the HCAb is produced by plasmablasts and plasma cells and has essentially the same structure except that the 71 amino acid long TM region is replaced by a single lysine residue and the molecule is not associated with Igα/β.

Figure 3:
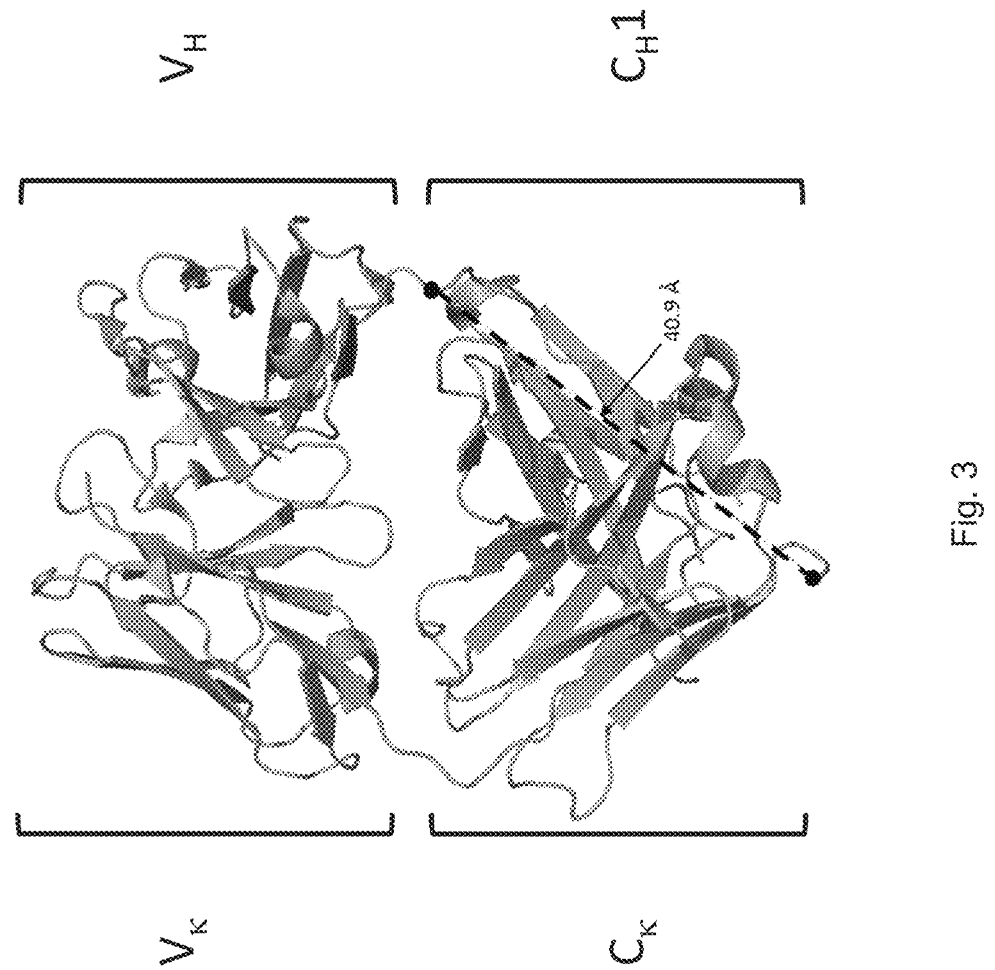

FIG. 3: Considerations in the design of Linker 2 (L2) length based on an antibody Fab crystal structure. L2 connects CL to CH1. The Fab structure and its constituent domains shown in the figure are of an IgG1κ mAb (Research Collaboratory for Structural Bioinformatics Protein Data Bank ID: 2XKN). The distance to be bridged to connect the COOH-terminus of Cκ and the $NH_2$-terminus of CH1 is 40.9 Å, indicated by the dashed line, but due to the relative position of Cκ and CH1, the linker is preferably longer in order to connect the COOH— and $NH_2$-termini. The theoretical length of a (GGGGS [SEQ ID NO:35])$_4$ linker is 76 Å, which is less than twice the coverage of the distance between the two termini (81.8 Å). Therefore, the exemplified linker length is (GGGGS [SEQ ID NO:35])$_{4-16}$.

Figure 4:
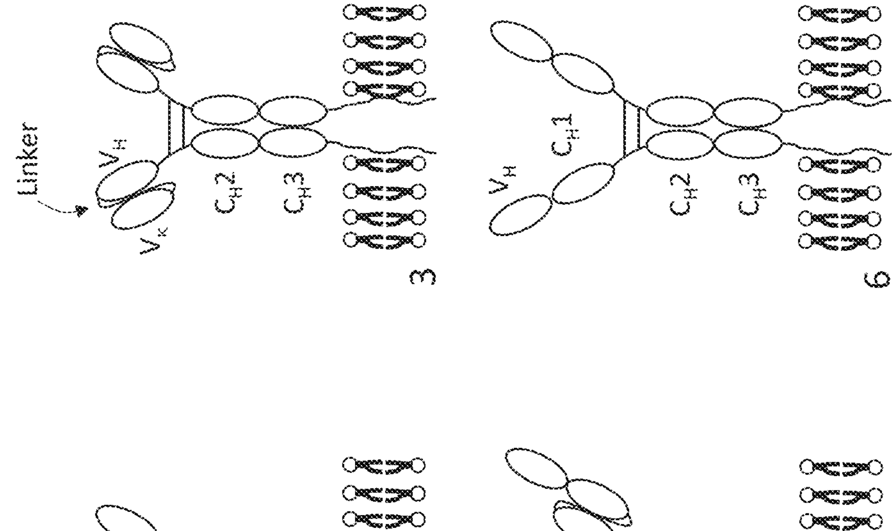
Figure 4:
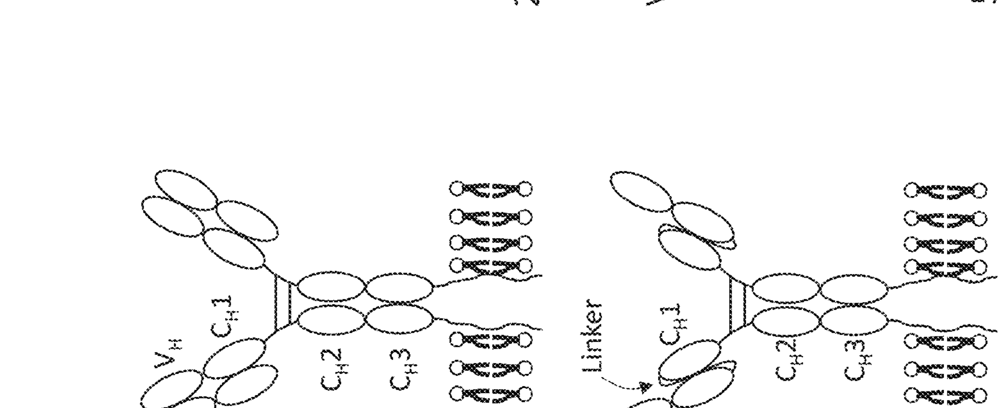

FIG. 4: Heavy chain antibody (HCAb) constructs generated to test for cell surface expression in vitro. (1) Positive control, conventional H2L2 IgG. (2 and 3) Positive controls known to be expressed on the cell surface without an LC. (2) Camel-like HCAb lacking CH1 (3) Single chain Fv (scFV) with VL directly linked to VH and lacking CH1. (4) HCAb described herein, with the protein domain structure NH—VH-Cκ-L2-CH1-CH2-CH3-TM-GOGH. (5) Same as construct 4 except that the order of CL and CH1 is reversed, VH-CH1-L2-Cκ-CH2-CH3-TM-COOH. (6) Negative control, conventional IgG without LC (H2L0). The constructs illustrated here encode a mouse HC (e.g., mouse IgG1) that contains a transmembrane region for insertion into the plasma membrane. Constructs encoding the secreted form were also generated to test for HCAb secretion. Constructs were transfected into HEK 293T cells.

Figure 5:
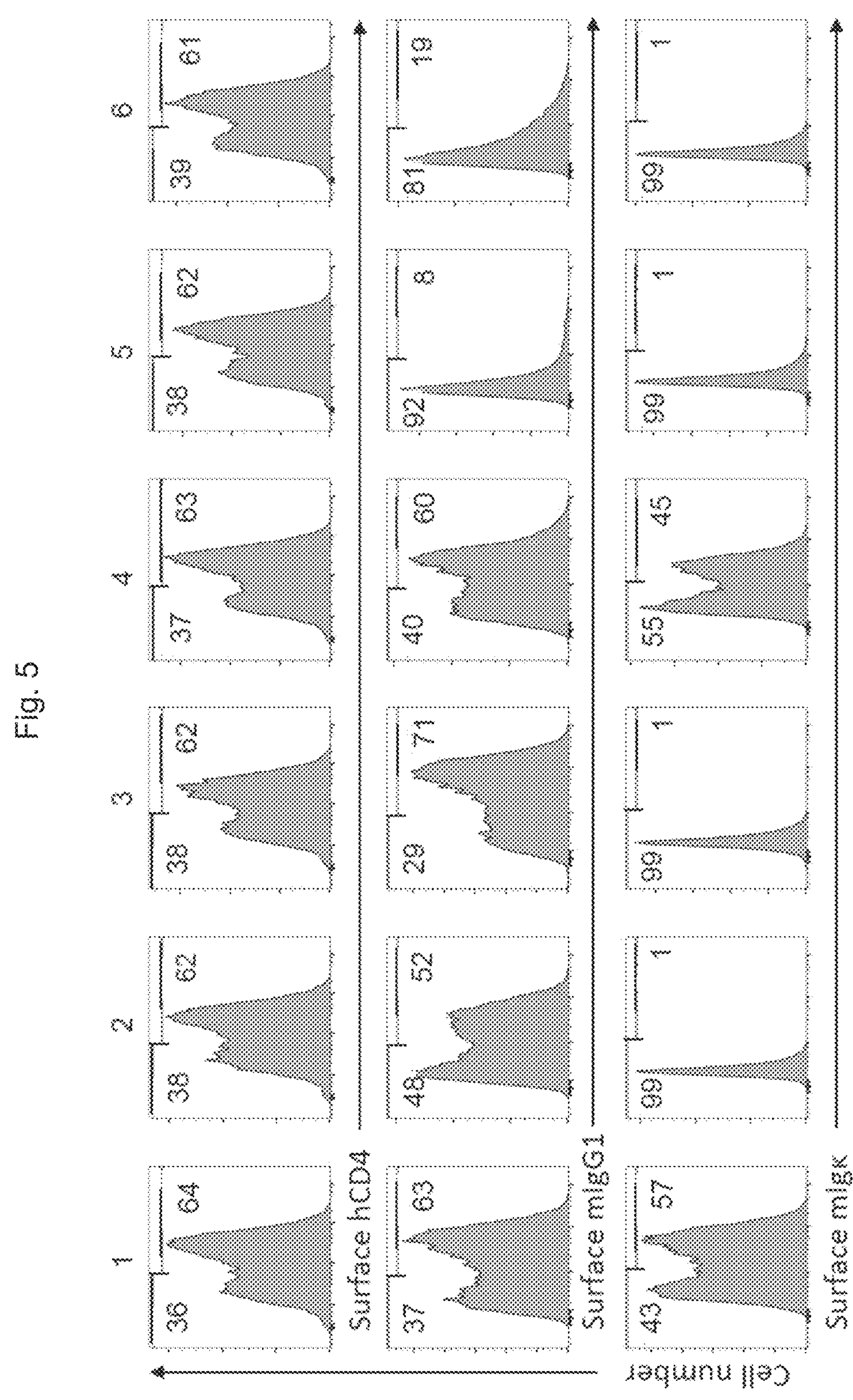

FIG. 5: Cell surface expression of the HCAb constructs depicted in FIG. 4. The constructs depicted in FIG. 4 were transiently transfected into HEK 293T cells using Lipofectamine 2000 (Invitrogen) together with a vector encoding myc-tagged human CD4 (hCD4) as a transfection control. Additionally, all HEK 293T cells were co-transfected with a construct expressing both mouse CD79a and CD79b (Igα/Igβ), which are co-receptors required for the surface expression of B cell antigen receptors, including membrane-bound forms of HCAb (Wienands and Engles, Int. Rev. Immunol., 20:679, 2001). After 20-24 hrs the cells were stained for cell surface hCD4, mouse IgG1 (mIgG1) and mouse κ light chain (mIgκ) and analyzed by flow cytometry. Numbers at the top of the figure correspond to the construct numbers in FIG. 4. Numbers at the top of each flow plot indicate the frequency of negative (left) and positive (right) cells.

Figure 6:
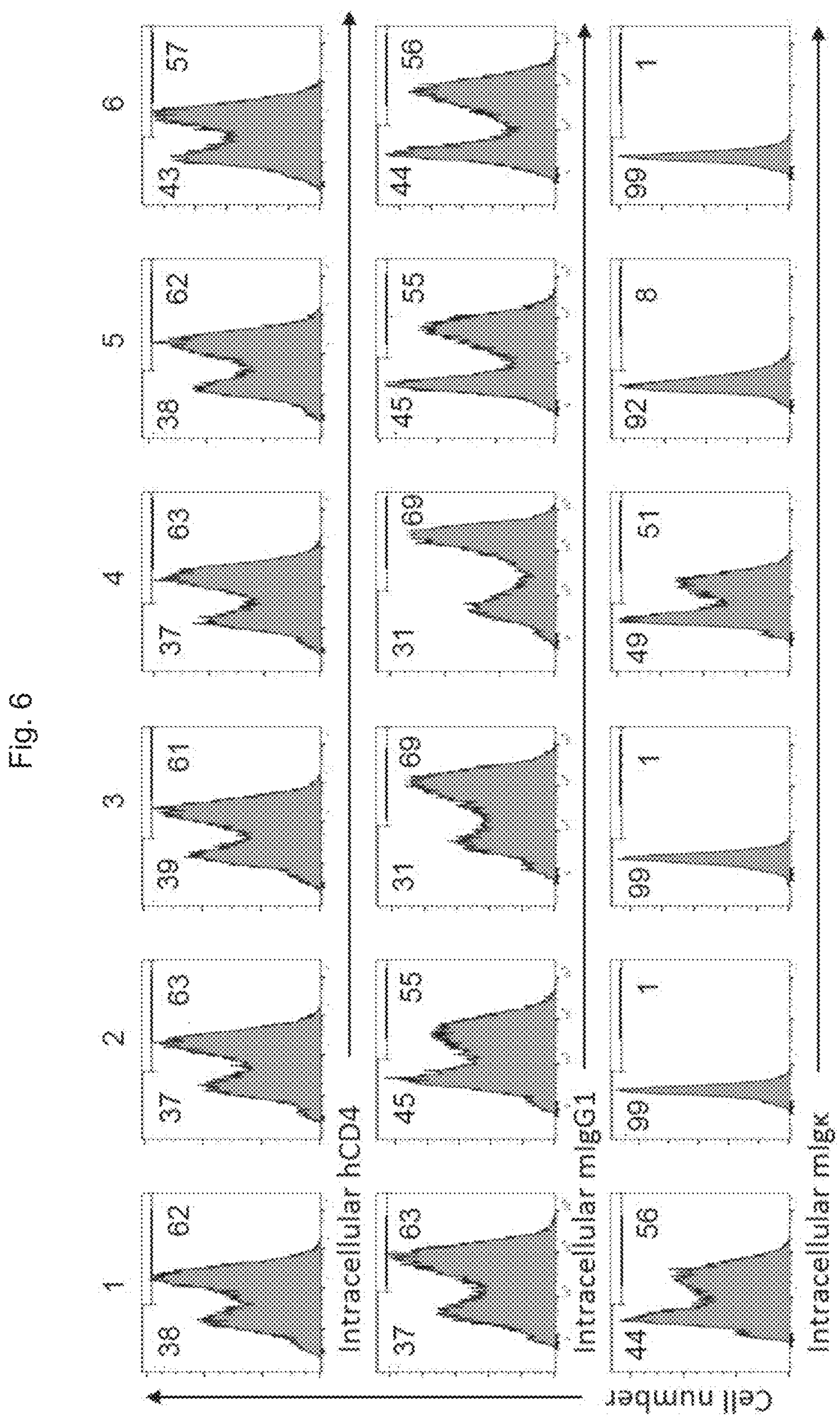

FIG. 6: Staining of transfected cells for intracellular hCD4, mIgG1 and mIgκ. A sample of cells from the transfection depicted in FIG. 5 were fixed, permeabilized and stained for intracellular expression of hCD4, mIgG1 and migκ. Flow cytometry was used to verify that all constructs were being expressed.

Figure 7B:
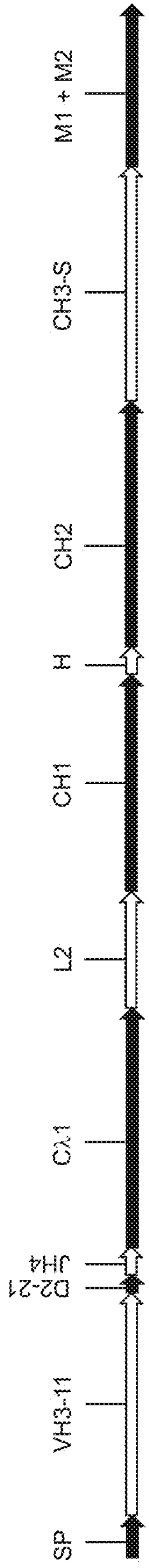

FIG. 7A: Heavy chain antibody (HCAb) constructs generated to compare Cκ, Cλ1 and Cλ2 for efficiency of cell surface expression in vitro. (1) Positive control, camel-like HCAb lacking CH1. (2) HCAb described herein, with the structure VH-Cκ-L2-CH1-CH2-CH3-TM. (3) HCAb described herein, with the structure VH-Cλ1-L2-CH1-CH2-CH3-TM. [SEQ ID NO:47, nucleotide sequence; SEQ ID NO:48, amino acid sequence](4) HCAb described herein, with the structure VH-Cλ2-L2-CH1-CH2-CH3-TM. The constructs illustrated here encode a transmembrane region for insertion into the plasma membrane. Constructs encoding the secreted form were also generated to test for HCAb secretion. FIG. 7B: Schematic of the construct 3 fusion gene, 5' to 3'. SP, signal peptide; VH3-11, D2-21, JH4 are the VH, DH and JH gene segments used for the heavy chain VDJ rearrangement; Cλ1, light chain constant region; L2, linker 2; CH1, exon encoding the CH1 domain of IgG1; H, IgG1 hinge region exon; CH2, exon encoding the CH2 domain of IgG1; CH3-S, exon encoding the CH3 domain of IgG1 and the secretory tail; M1+M2, exons encoding the IgG1 transmembrane region.

Figure 8:
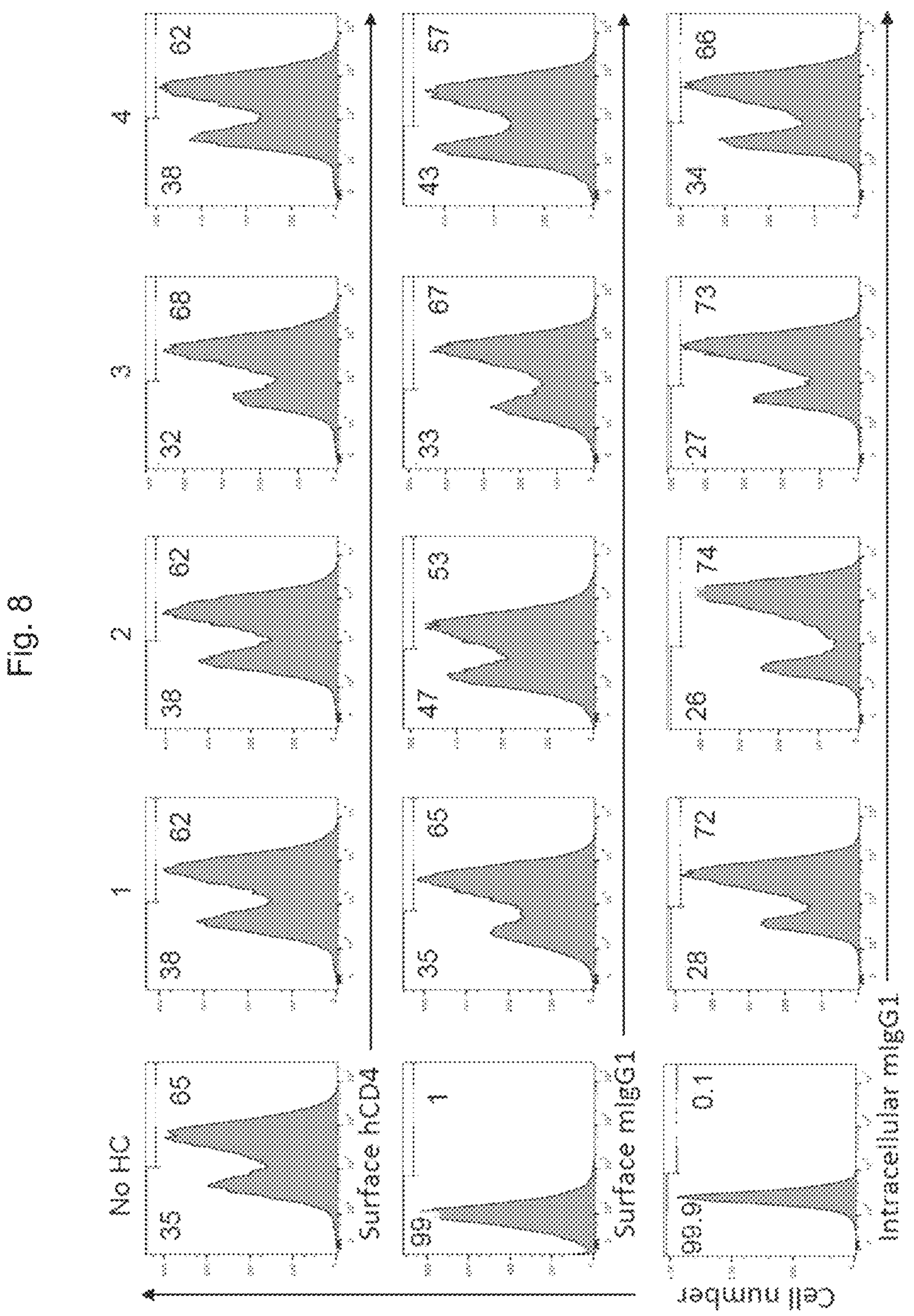

FIG. 8: Cell surface expression of the HCAb constructs depicted in FIG. 7A. The constructs depicted in FIG. 7A were transiently transfected into HEK 293T cells using Lipofectamine 2000 (Invitrogen) together with a vector encoding myc-tagged human CD4 (hCD4) as a transfection control. Additionally, all HEK 293T cells were co-transfected with a construct expressing both mouse CD79a and CD79b (Igα/Igβ), which are co-receptors required for the surface expression of antigen receptors including membrane-bound forms of HCAb (Wienands and Engles, Int. Rev. Immunol., 20:679, 2001). After 20-24 hrs the cells were stained for cell surface hCD4 (top row) or mouse mIgG1 (middle row) or fixed and permeabilized and stained for intracellular mouse mIgG1 (bottom row) and analyzed by flow cytometry. Left (No HC) column, cells transfected with only the hCD4 construct. Columns 1-4, cells transfected with hCD4 plus the constructs as numbered in FIG. 7A. Numbers at the top of each flow plot indicate the frequency of negative (left) and positive (right) cells.

Figure 9:
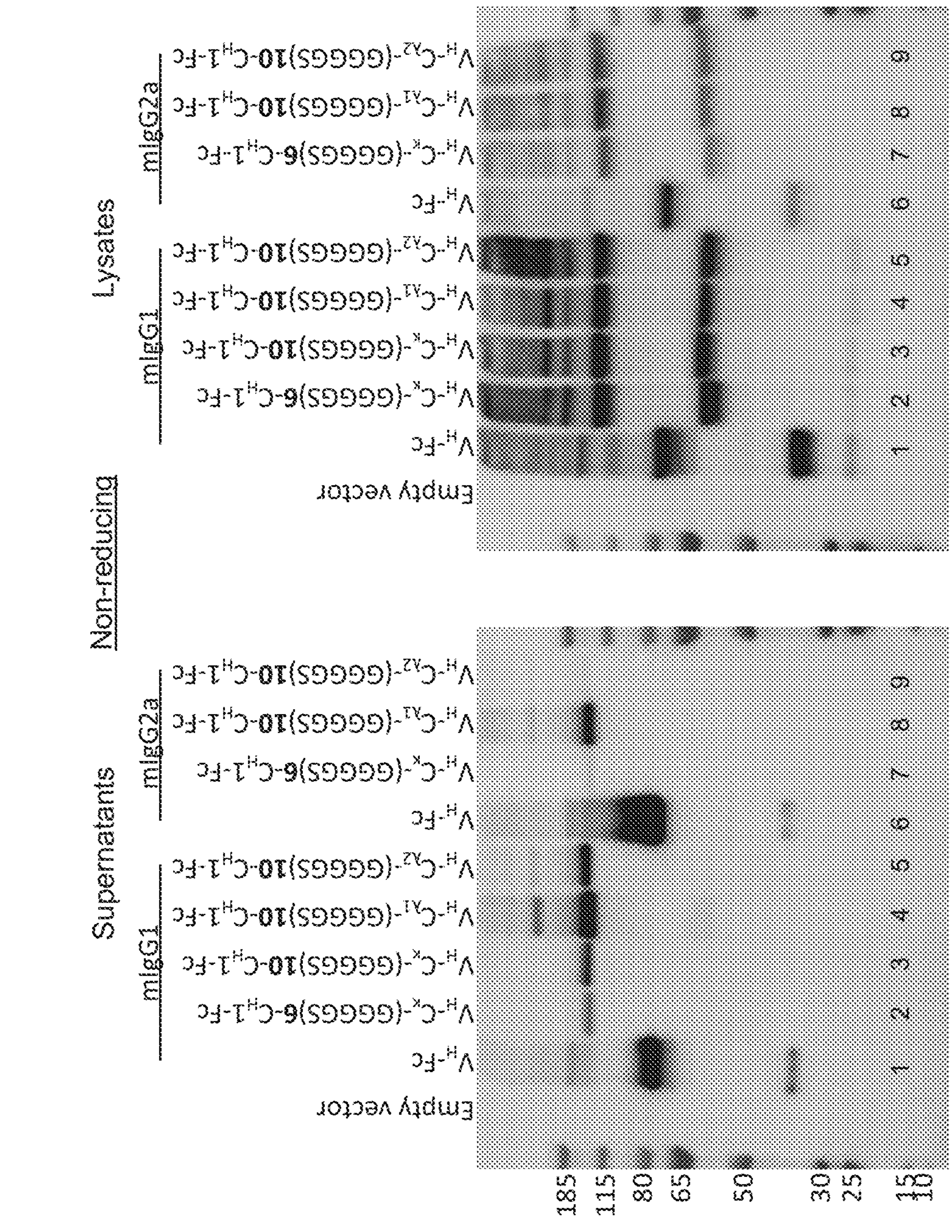

FIG. 9: Western blot analysis of secretion and intracellular expression of the various HCAb constructs. Cells transfected with the indicated constructs were cultured for 40-48 hrs, then centrifuged. Supernatants were collected to detect HCAb secretion (left) and the cell pellets were lysed in NP-40 to detect intracellular expression (right) of the HCAb. Samples were subjected to SDS-polyacrylamide gel electrophoresis (SDS-PAGE) under non-reducing conditions, blotted to PVDF membranes and then probed with HRP-labeled anti-mouse IgG Fc antibodies. mIgG1, the CH1 and/or Fc regions of the vector encode mIgG1. mIgG2a, the CH1 and/or Fc regions of the vector encode mIgG2a. The constructs also differ by L2 length (6 or 10) and CL (Cc, Cλ1, or Cλ2) as indicated on the figure. Empty vector, expression vector with no insert. Lane 1, VH-Fc, camel-like HCAb. Molecular weight markers (kDa0 are visible on the left and right sides of the gels.

FIG. 9 refers to repeats of the sequence GGGGS (SEQ ID NO:35).

Figure 10:
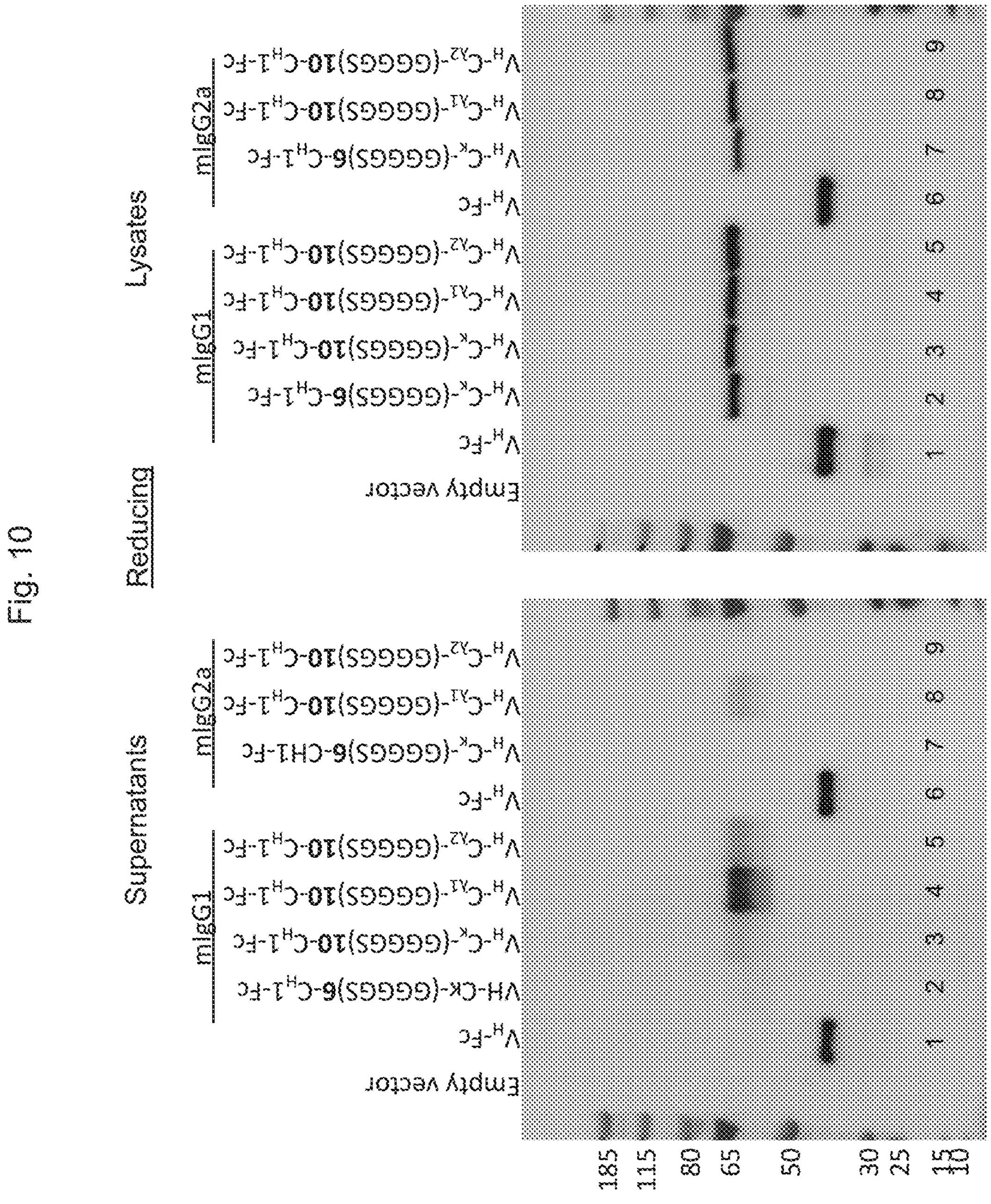

FIG. 10: Western blot analysis of secretion and intracellular expression of the various HCAb constructs. Identical to FIG. 9 except that the gels were run under reducing conditions. FIG. 10 refers to repeats of the sequence GGGGS (SEQ ID NO:35).

Figure 11:
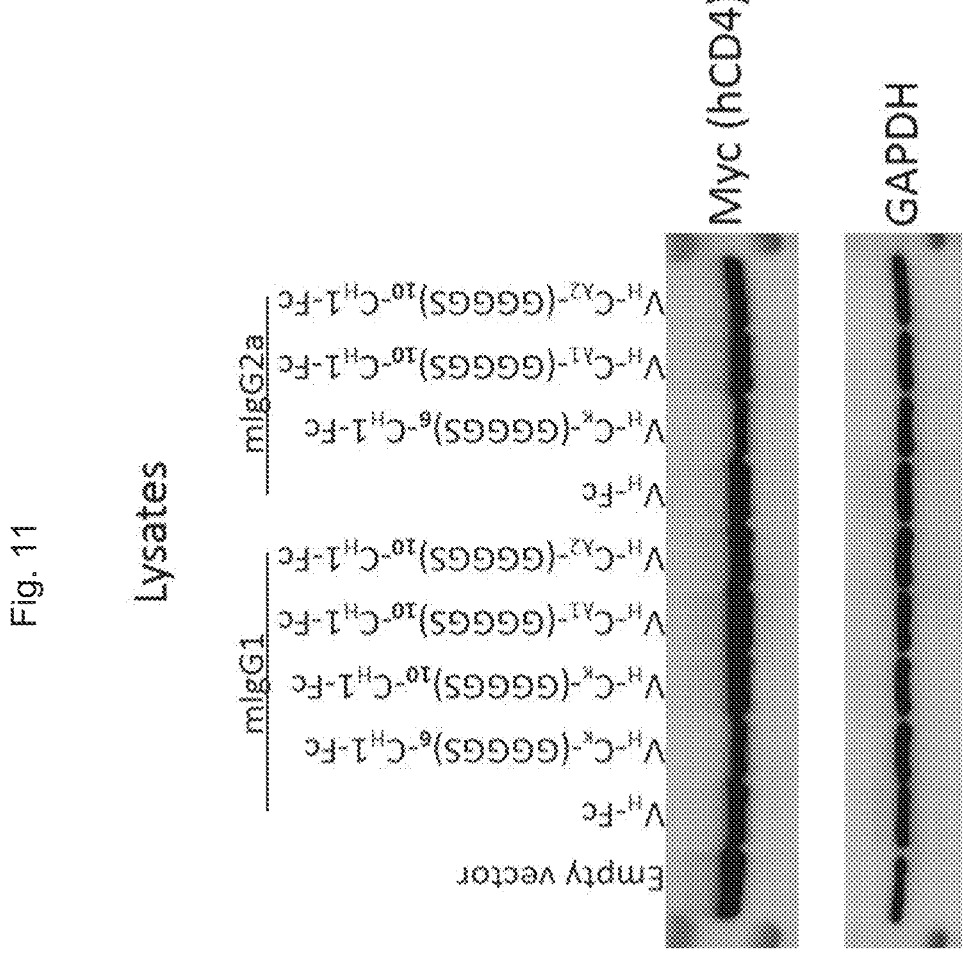

FIG. 11: Transfection and loading controls for the blots shown in FIG. 9 and FIG. 10. Blots were stripped and re-probed with anti-myc or anti-GAPDH mAbs. The hCD4 construct includes a myc-tag to serve as a transfection control. GAPDH is a housekeeping gene used as a loading control. FIG. 11 refers to repeats of the sequence GGGGS (SEQ ID NO:35).

Figure 12:
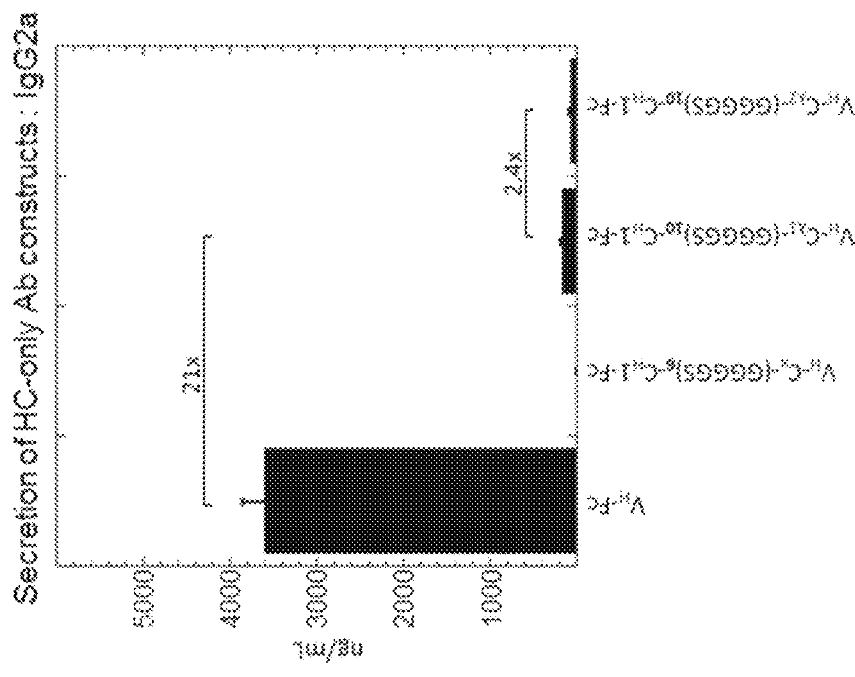
Figure 12:
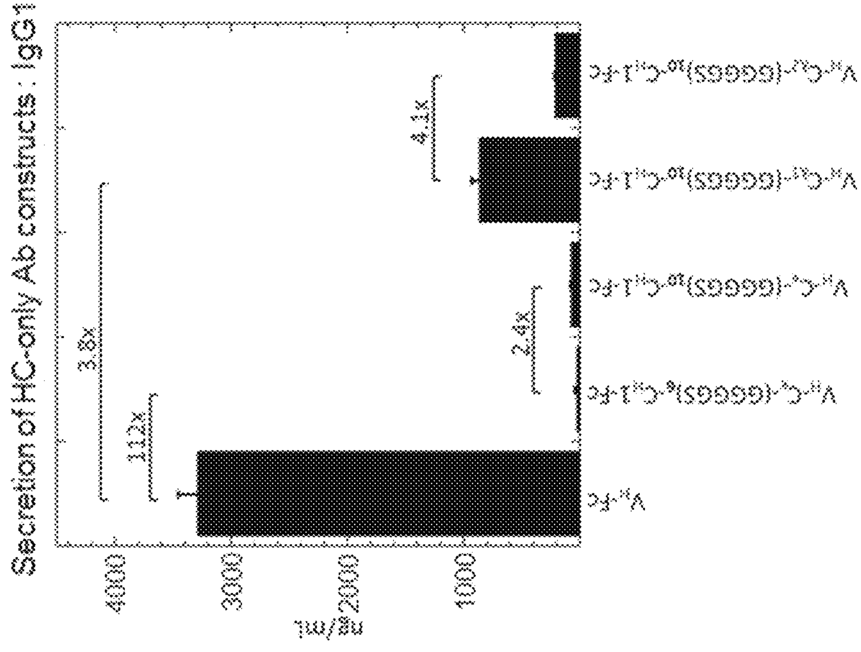

FIG. 12: Quantitation of HCAb secretion by ELISA. The amount of secreted IgG1 (left) and IgG2a (right) HCAb in supernatants from transfectants depicted in FIG. 9 was determined by ELISA. FIG. 12 refers to repeats of the sequence GGGGS (SEQ ID NO:35).

Figure 13:
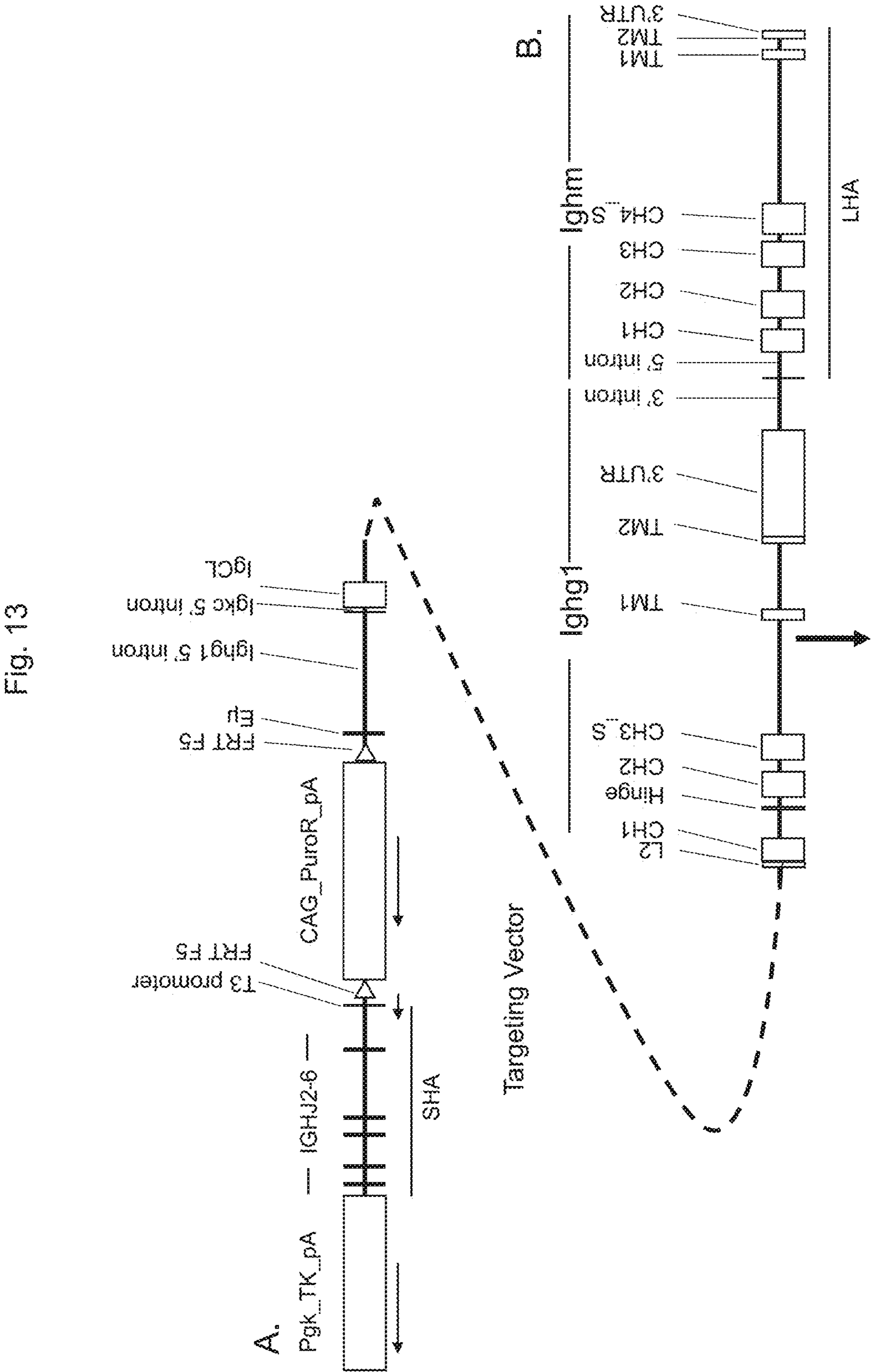
Figure 13:
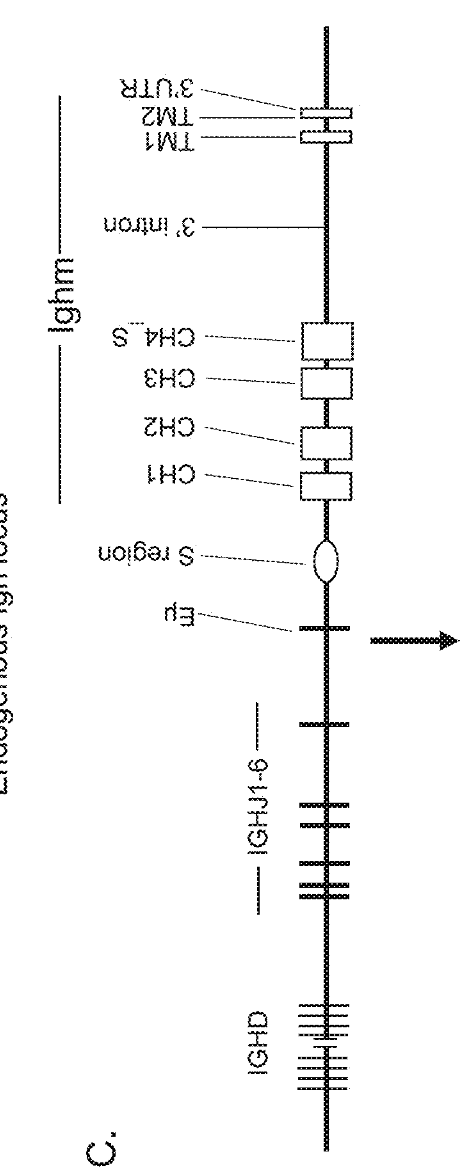
Figure 13:
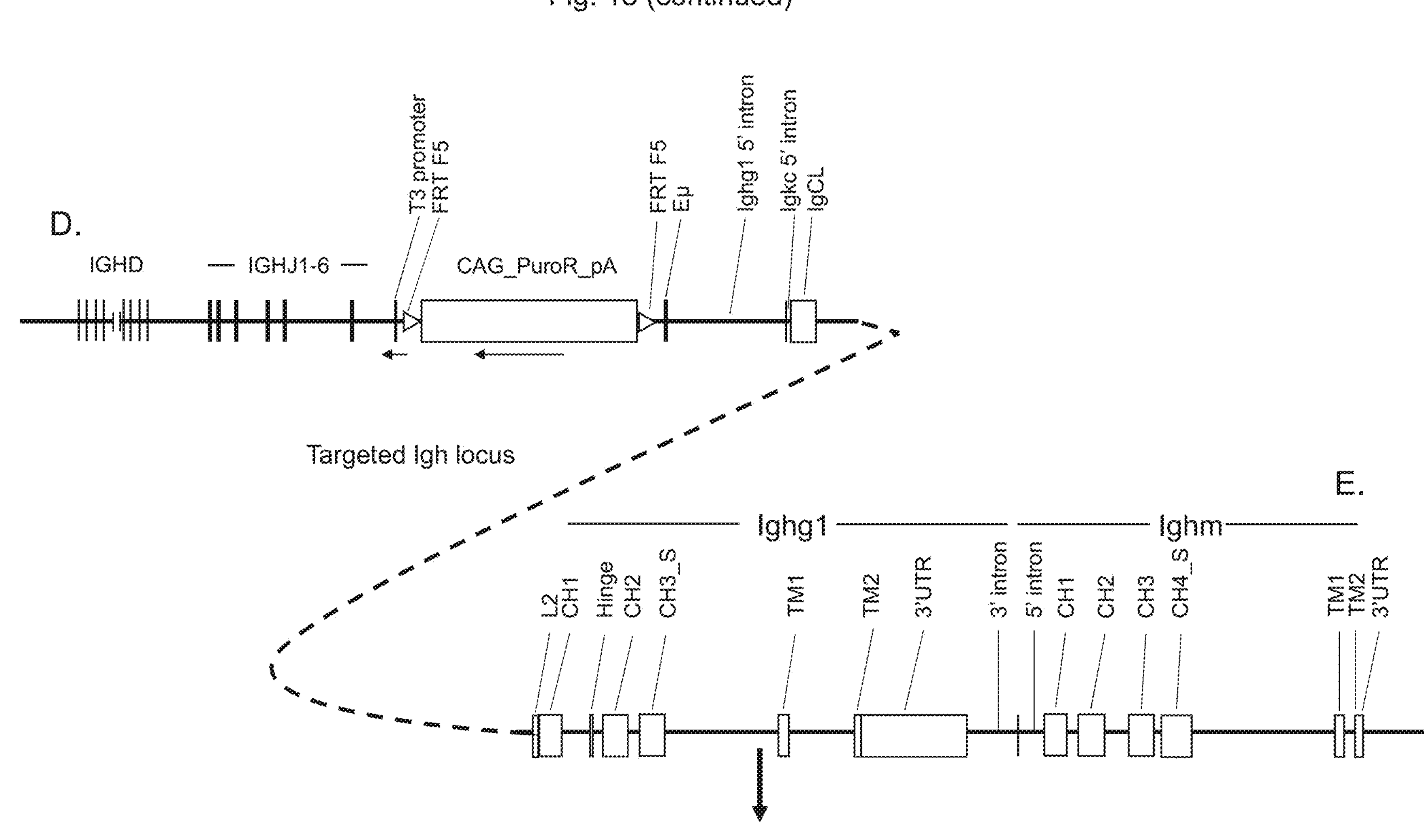
Figure 13:
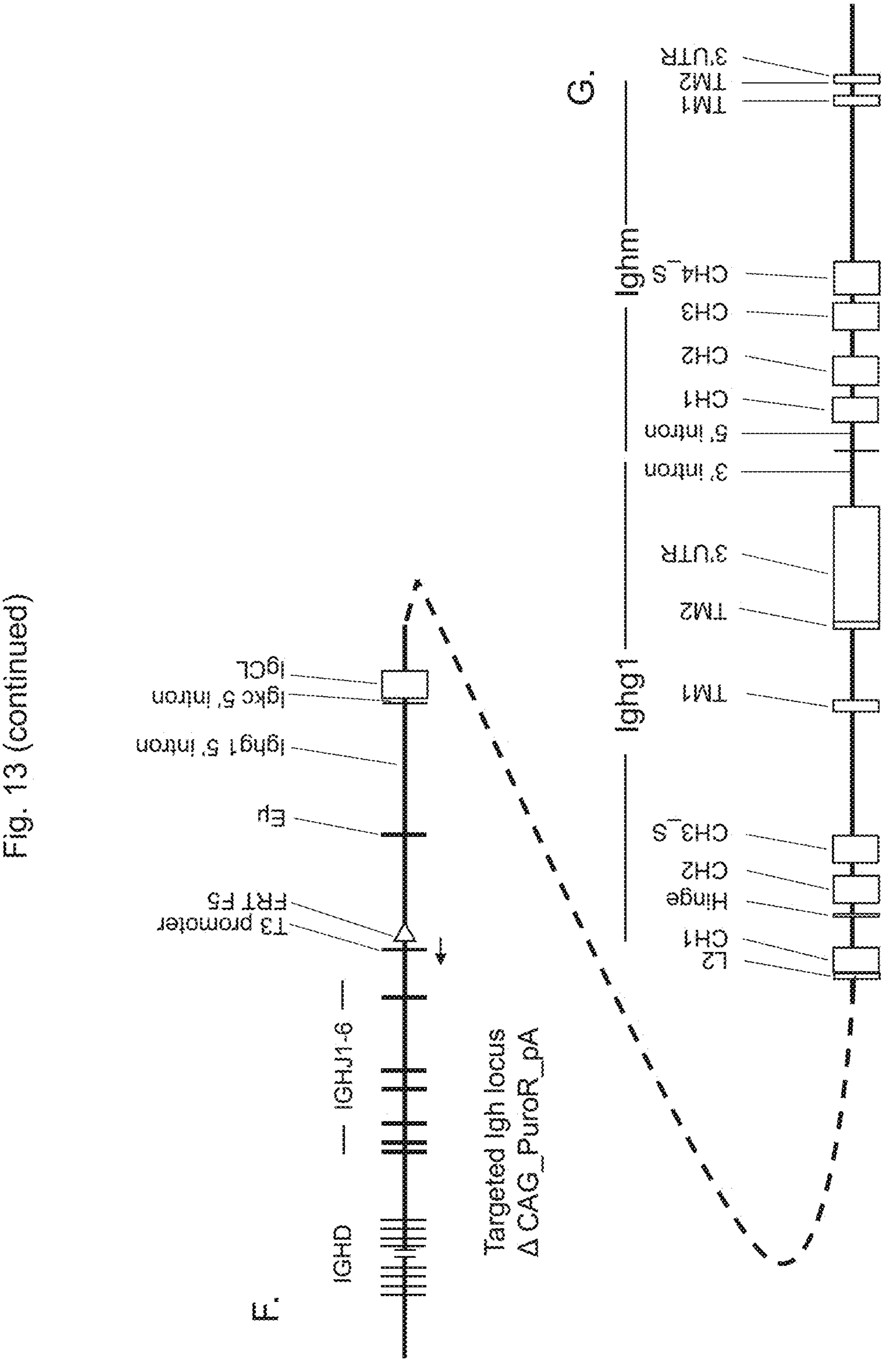

FIG. 13: Strategy for introduction of a mouse CL-L2-CH1-H-CH2-CH3_S-TM gene cassette into an endogenous mouse Igh locus upstream of Ighm by homologous recombination for the production of HCAbs. In this figure and FIGS. 14A, 14B, 14C, and FIG. 15, the "endogenous mouse Igh locus" is in ES cells containing a partially human Igh locus described in US Pub. No. 20130219535A1 by Wabl and Killeen. FIGS. 13A and 13B: The structure of the targeting vector. The segments labeled A. and B. and connected by the dashed line in the figure are contiguous in the targeting vector. FIG. 13C: The region of the endogenous mouse Igh locus to be targeted. FIGS. 13D and 13E: The resulting targeted mouse Igh locus. The segments labeled D. and E. and connected by the dashed line in the figure are contiguous in vivo. FIGS. 13F and G: The final targeted locus after removal of the selectable marker by Flp recombinase. The segments labeled F. and G. and connected by the dashed line in the figure are contiguous in vivo. IgCL in this and subsequent figures indicates a light chain constant region either Cκ or Cλ (Cλ1, Cλ2 or Cλ3 in the case of the mouse).

FIGS. 14A, 14B, 14C, and FIG. 15: Strategy for introduction of a mouse CL-L2-CH1-H-CH2-CH3_S-TM gene cassette into an endogenous mouse Igh locus upstream of Ighm by recombinase-mediated cassette exchange (RMCE) for the production of HCAbs.

Figure 14A:
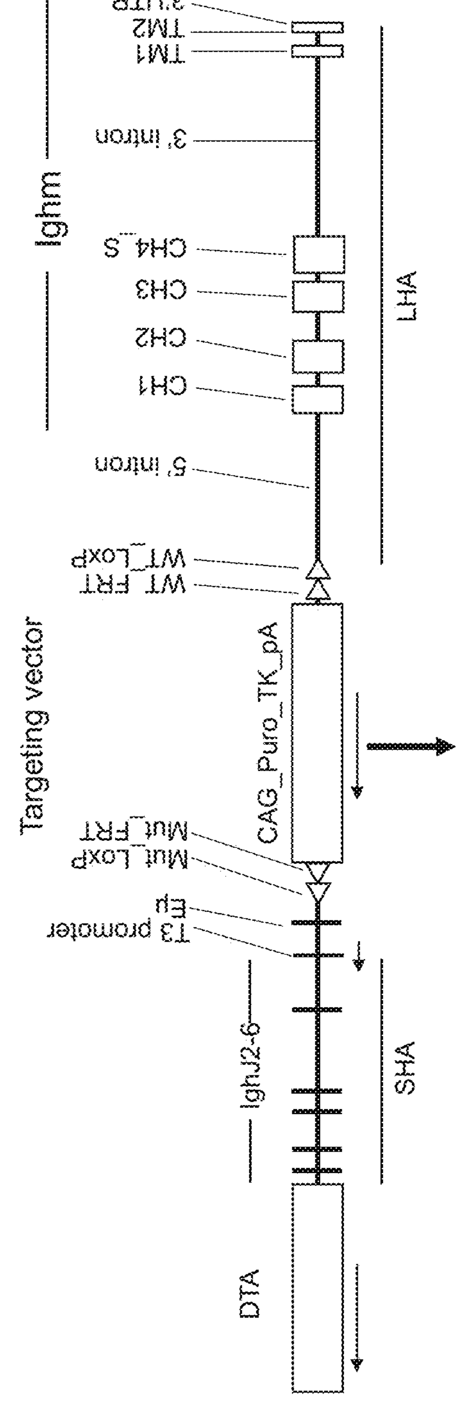
Figure 14B:
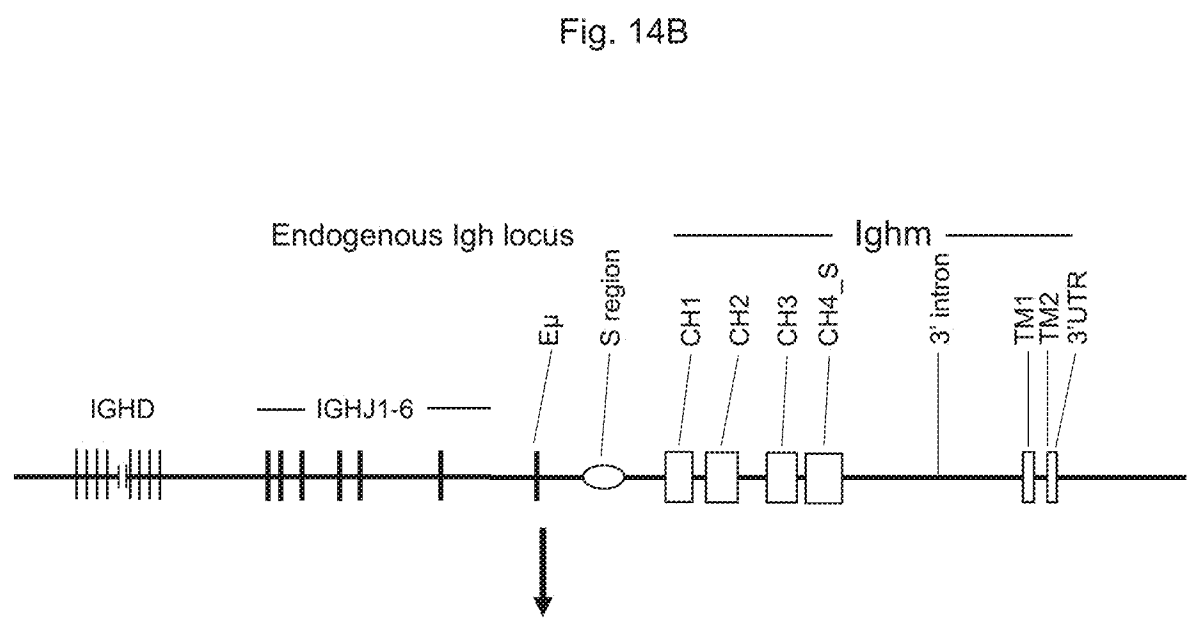

FIGS. 14A, 14B and 14C: Step 1, generation or the RMCE acceptor allele. FIG. 14A: The structure of the RMCE targeting vector. FIG. 14B: The region of the endogenous mouse Igh locus to be targeted. FIG. 14C: The resulting targeted mouse Igh locus.

Figure 15:
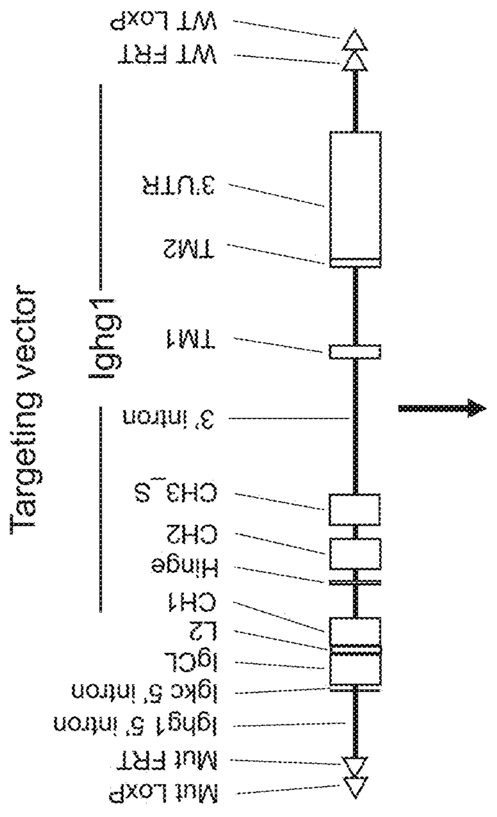
Figure 15:
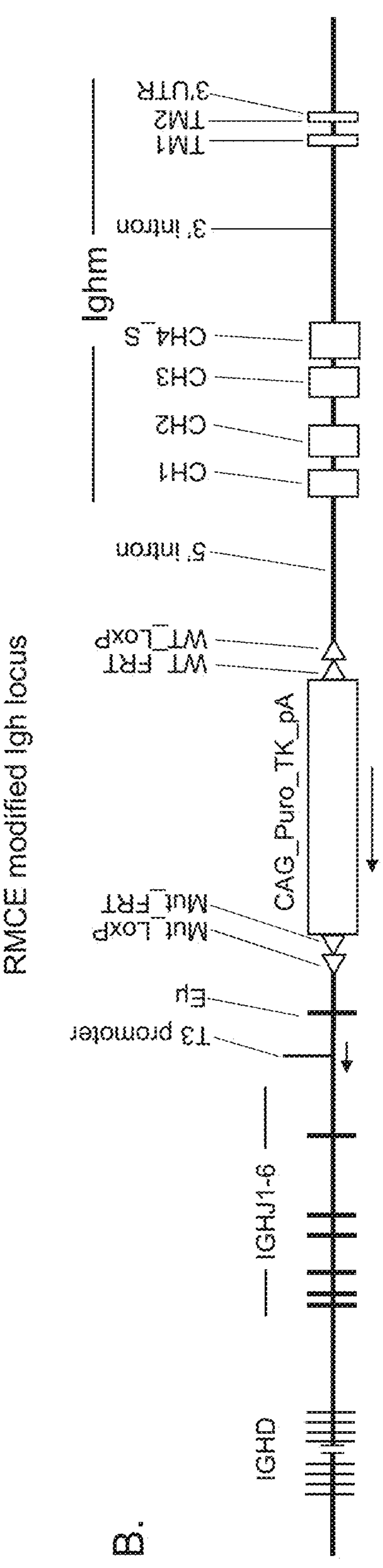

FIG. 15: Step 2, targeting the RMCE-modified acceptor allele with the CL-L2-CH1-H-CH2-CH3_S-TMvector. FIG. 15A: The structure of the RMCE targeting vector. FIG. 15B: The RMCE-modified Igh locus. FIGS. 15C and 15D: The resulting targeted Igh locus. The segments labeled C. and D. and connected by the dashed line in the figure are contiguous in vivo.

FIG. 16: sequences referred to herein.

DETAILED DESCRIPTION OF THE INVENTION

Unless indicated or defined otherwise, all terms used herein have their usual meaning in the art, which will be clear to the skilled person. Reference is for example made to the standard handbooks, such as Sambrook et al, "Molecular Cloning: A Laboratory Manual" (2nd Ed.), Vols. 1-3, Cold Spring Harbor Laboratory Press (1989); Lewin, "Genes IV", Oxford University Press, New York, (1990), and Janeway et al, "Immunobiology" (5th Ed., or more recent editions), Garland Science, New York, 2001.

The position of an amino acid residue in an antibody as referred to herein is understood as a position corresponding to the IMGT numbering. (IMGT®, the international ImMunoGeneTics information system®). The IMGT numbering refers to the numbering of a naturally occurring antibody. An explanation of the IMGT database and numbering scheme can be found in Giudicelli et al., Nuc. Acids Res., 34:D781, 2006.

The antibody constructs herein referred to as scVHAb and HCAb are artificial constructs which are not naturally-occurring. It is well understood that the materials, methods and uses of the invention, e.g., specifically referring to isolated nucleic acid sequences, amino acid sequences, expression constructs, transformed host cells, transgenic animals and recombinant antibodies, are "man-made" or synthetic, and are therefore not considered as a result of the "laws of nature".

The term "antibody" as used herein shall refer to polypeptides or proteins that consist of or comprise antibody domains in various combinations or constructions, which are understood as constant and/or variable domains of the heavy and/or light chains of immunoglobulins, with or without linker sequences. Polypeptides are understood as antibody domains, if comprising a beta-barrel structure consisting of at least two beta-strands of an antibody domain structure connected by a loop sequence. Antibody domains may be of native structure or modified by mutagenesis or derivatization, e.g., to modify the antigen binding properties or any other property, such as stability or functional properties, such as binding to the Fc receptors, Fcμ, Fcα/μ, Fcα, Fcε, and/or Fcγ receptors (e.g., FcRn, FcγRI, FcγRIIB, FcγRIII, or FcγRIV in the mouse) or to the polymeric Ig receptor (pIgR).

Herein, the term "antibody" and "immunoglobulin" are used interchangeably.

The term "antibody" as used herein shall particularly refer to antibody constructs comprising VH as a single variable antibody domain, in combination with constant antibody domains with one or more linking sequence(s) or hinge region(s), such as heavy-chain antibodies, composed of one or two single chains, wherein each single chain comprises or consists of a variable heavy chain region (or VH) linked to constant domains. Exemplary antibodies comprise or consist of any of the scVHAb or HCAb further described herein. Antibodies described herein may comprise or consist of antibody domains which are of an IgG type (e.g., an IgG1, IgG2, IgG3, or IgG4 subtype), IgA1, IgA2, IgD, IgE, or IgM type, or their murine counterparts, IgG1, IgG2a/c, IgG2b, IgG3, IgA, IgD, IgE or IgM.

In accordance therewith, an antibody is typically understood as a protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as immunoglobulin variable region genes. Light chains (LC) are classified as either kappa or lambda. Heavy chains (HC) are classified as gamma, mu, alpha, delta, or epsilon, which in turn define the immunoglobulin classes, IgG, IgM, IgA, IgD and IgE, respectively.

In a typical IgG antibody structure, HC or LC each contains at least two domains connected to each other to produce a pair of binding site domains. In specific cases, a heavy chain may incorporate a LC constant domain, yet still be considered a HC, e.g., being devoid of a light chain variable domain or region.

The HC of an antibody may comprise a hinge region connecting one or two antigen-binding arms of the antibody to an Fc part. In particular, the scVHAb described herein may suitably comprise a hinge region as a C-terminal extension, such as to connect the scVHAb to further elements that comprise a peptide/polypeptide sequence. Exemplary antibody constructs may contain antibody constant domains, such as of an Fc connected through the hinge region.

The hinge region may be a naturally-occurring heavy chain hinge region of an immunoglobulin, e.g., of an IgG1 or an IgG3, or an artificial hinge region comprising or consisting of a number of consecutive amino acids which is of about the same length (+/−20%, or +/−10%) as a naturally-occurring one. Preferred hinge regions comprise one or more, e.g., 2, 3, or 4 cysteine residues which may form disulphide bridges to another hinge region thereby obtaining a dimeric construct.

The antibody described herein may comprise one or more antibody domains that are either shortened or extended, e.g., using linking sequences or a linker. Such linkage is specifically by recombinant fusion or chemical linkage. Specific linkage may be through linking the C-terminus of one domain to the N-terminus of another domain, e.g., wherein one or more amino acid residues in the terminal regions are deleted to shorten the domain size or extended to increase flexibility of the domains.

Specifically, the shortened domain sequence comprises a deletion of the C-terminal and/or N-terminal region, such as to delete at least 1, 2, 3, 4, or 5, up to 6, 7, 8, 9, or 10 amino acids.

A domain extension by a linker may be through an amino acid sequence that originates from the N- or C-terminal region of an immunoglobulin domain that would natively be positioned adjacent to the domain, such as to include the native junction between the domains. Alternatively, the linker may contain an amino acid sequence originating from the hinge region. However, the linker may as well be an artificial sequence, e.g., rich in or consisting of a plurality of Gly and Ser amino acids.

The term "antigen-binding site" or "binding site" refers to the part of an antibody that participates in antigen binding. The antigen binding site in a natural antibody is formed by amino acid residues of the N-terminal variable ("V") regions of the heavy ("H") and/or light ("L") chains, or the variable domains thereof. Three highly variable stretches within the V regions of a heavy chain (and optionally a light chain), referred to as "hypervariable regions", are interposed between more conserved flanking stretches known as framework regions. The antigen-binding site provides for a surface that is complementary to the three-dimensional surface of a bound epitope or antigen, and the hypervariable regions are referred to as "complementarity-determining regions", or "CDRs." The binding site incorporated in the CDRs is herein also called "CDR binding site".

The term "CDR region" or respective sequences refers to the variable antigen-binding region of a variable antibody domain, such as a VH or VHH domain, which includes varying structures capable of binding interactions with antigens. Antibody domains with CDR regions can be used as such or integrated within a larger proteinaceous construct, thereby forming a specific region of such construct with binding function. The varying structures can be derived from natural repertoires of binding proteins such as immunoglobulins, specifically from antibodies or immunoglobulin-like molecules. The varying structures can as well be produced by randomisation techniques, in particular those described herein. These include mutagenized CDR loop regions of antibody variable domains, in particular CDR loops of immunoglobulins.

Typically, an antibody having an antigen-binding site with a specific CDR structure is able to specifically bind a target antigen, i.e., specifically recognizing such target antigen through the CDR loops of a pair of VH/VL domains.

In a HC antibody, the antigen-binding site is characterized by a specific CDR structure only consisting of the VH-CDR1, VH-CDR2, and VH-CDR3 loops. Such an antigen-binding site is understood to be native, or of a native structure and/or conformation, if produced by an animal, e.g., a transgenic non-human animal as described herein. Though the antigen-binding site can be artificially produced, because engineered by recombination techniques synthesizing new structures, the incorporation of respective genes encoding the respective antibody into a transgenic non-human animal results in the production of new synthetic antibodies which have a native conformation.

Such native conformation can be further affinity matured by any in vivo or in vitro technique of affinity maturation, thereby producing polyclonal and/or monoclonal antibodies comprising an artificial antigen-binding site characterized by a native conformation, and further characterized by a high affinity of specifically binding its target antigen.

The term "antibody" shall apply to antibodies of animal origin, such as mammalian, including human, murine, rabbit, and rat, or avian, such as chicken, which term shall particularly include recombinant antibodies that are based on a sequence of animal origin, e.g., mouse sequences.

The term "antibody" further applies to fully human antibodies.

The term "fully human" as used with respect to an immunoglobulin is understood to include antibodies having variable and constant regions derived from human germline immunoglobulin sequences. A human antibody may include amino acid residues not encoded by human germline immunoglobulin sequences (e.g., mutations introduced by random or site-specific mutagenesis in vitro or by somatic mutation in vivo), for example in the CDRs. Human antibodies include antibodies isolated from human immunoglobulin or antibody libraries or from animals transgenic for one or more human immunoglobulins.

A human immunoglobulin is preferably selected or derived from the group consisting of IgA1, IgA2, IgD, IgE, IgG1, IgG2, IgG3, IgG4 and IgM.

A murine immunoglobulin is preferably selected or derived from the group consisting of IgA, IgD, IgE, IgG1, IgG2A, IgG2B, IgG2C, IgG3 and IgM.

The term "antibody" further applies to chimeric antibodies, with mixed sequences that originate from different species, such as sequences of murine and human origin.

Specifically, the term "antibody" applies to antibodies produced by transgenic non-human animals, e.g., from mice, which comprise human antigen-binding regions and non-human (e.g., murine) constant regions or framework sequences.

The term "chimeric" as used with respect to an immunoglobulin or an antibody refers to those molecules wherein one portion of an antibody chain is homologous to corresponding sequences in immunoglobulins derived from a particular species or belonging to a particular class, while the remaining segment of the chain is homologous to corresponding sequences in another species or class. Typically, the variable region mimics the variable regions of immunoglobulins derived from one species of mammals, while the constant portions are homologous to sequences of immunoglobulins derived from another. In one example, the variable region can be derived from presently known sources using readily available B-cells from human host organisms in combination with constant regions derived from, for example, non-human cell preparations.

The term "antibody" further applies to a monoclonal antibody, specifically a recombinant antibody, which term includes all types of antibodies and antibody structures that are prepared, expressed, created or isolated by recombinant means, such as antibodies originating from animals, e.g., mammalians including human, that comprises genes or sequences from different origin, e.g., chimeric, humanized antibodies, or hybridoma derived antibodies. Further examples refer to antibodies isolated from a host cell transformed to express the antibody, or antibodies isolated from a recombinant, combinatorial library of antibodies or antibody domains, or antibodies prepared, expressed, created or isolated by any other means that involve splicing of antibody gene sequences to other DNA sequences.

The term "antibody" is understood to include functionally active variants of new or existing (herein referred to as "parent") molecules, e.g., naturally occurring immunoglobulins. It is further understood that the term includes antibody variants and shall also include derivatives of such molecules as well. A derivative is any combination of one or more antibodies and or a fusion protein in which any domain of the antibody, e.g., an antibody domain comprising the antigen-binding site of the VH domain, or the VH domain, may be fused at any position to one or more other proteins, such as to other antibodies, e.g., a binding structure comprising CDR loops, a receptor polypeptide, but also to other ligands, enzymes, toxins and the like. The antibodies as described herein can be specifically used as isolated polypeptides or as combination molecules, e.g., through recombination, fusion or conjugation techniques, with other peptides or polypeptides.

A derivative of the antibody may also be obtained by association or binding to other substances by various chemical techniques such as covalent coupling, electrostatic interaction, disulphide bonding, etc. The other substances bound to the antibodies may be lipids, carbohydrates, nucleic acids, organic and inorganic molecules or any combination thereof (e.g., PEG, prodrugs or drugs). A derivative may also comprise an antibody with the same amino acid sequence but made completely or partly from non-natural or chemically modified amino acids. In a specific embodiment, the antibody is a derivative comprising an additional tag allowing specific interaction with a biologically acceptable compound. There is not a specific limitation with respect to the tag usable in the present invention, as far as it has no or tolerable negative impact on the binding of the immunoglobulin to its target. Examples of suitable tags include His-tag, Myc-tag, FLAG-tag, Strep-tag, Calmodulin-tag, GST-tag, MBP-tag, and S-tag. In another specific embodiment, the antibody is a derivative comprising a label. The term "label" as used herein refers to a detectable compound or composition which is conjugated directly or indirectly to the antibody so as to generate a "labeled" antibody. The label may be detectable by itself, e.g., radioisotope labels or fluorescent labels, or, in the case of an enzymatic label, may catalyze chemical alteration of a substrate compound that is detectable.

A derivative of an antibody is e.g., derived from a parent antibody or antibody sequence, such as a parent antigen-binding (e.g., CDR) or framework (FR) sequence, e.g., mutants or variants obtained by e.g., in silico or recombinant engineering or else by chemical derivatization or synthesis.

The term "variant" shall specifically encompass functionally active variants. The functional variants of an antibody as described herein are particularly functional with regard to the specificity of antigen-binding.

The term "variant" shall particularly refer to antibodies, such as mutant antibodies or fragments of antibodies, e.g., obtained by mutagenesis methods, in particular to delete, exchange, introduce inserts or deletions into a specific antibody amino acid sequence or region or chemically derivatize an amino acid sequence, e.g., in the constant domains to engineer improved antibody stability, enhanced effector function or half-life, or in the variable domains to modulate antigen-binding properties, e.g., by affinity maturation techniques available in the art. Any of the known mutagenesis methods may be employed, including point mutations at desired positions, e.g., obtained by randomization techniques, or domain deletion as used for scVHAb or HCAb engineering. In some cases, positions are chosen randomly, e.g., with either any of the possible amino acids or a selection of preferred amino acids to randomize the antibody sequences. The term "mutagenesis" refers to any art recognized technique for altering a polynucleotide or polypeptide sequence. Preferred types of mutagenesis include error prone PCR mutagenesis, saturation mutagenesis, or other site directed mutagenesis.

The functional activity of an antibody in terms of antigen-binding is typically determined in an ELISA assay, BIAcore assay, Octet BLI assay, or flow cytometry-based assay when the antigen is expressed on a cell surface or intracellularly.

Functionally active variants may be obtained, e.g., by changing the sequence of a parent antibody, e.g., a monoclonal antibody having a specific native structure of an immunoglobulin, such as an IgG1 structure, to obtain a variant having the same specificity in recognizing a target antigen but having a structure which differs from the parent structure, e.g., to modify any of the antibody domains to introduce specific mutations or to produce a fragment of the parent molecule.

Specific functionally active variants comprise one or more functionally active CDR variants or a parent antibody, each of which comprises at least one point mutation in the parent CDR sequence, and comprises or consists of the amino acid sequence that has at least 60% sequence identity with the parent CDR sequence, preferably at least 70%, at least 80%, at least 90% sequence identity.

A specific variant is e.g., a functionally active variant of the parent antibody, wherein the parent CDR sequences are incorporated into human framework sequences, wherein optionally 1, 2, 3, or 4 amino acid residues of each of the parent CDR sequences may be further mutated by introducing point mutations to improve the stability, specificity and affinity of the parent or humanized antibody.

Specifically, the antibody may comprise a functionally active CDR variant of any of the CDR sequences of a parent antibody, wherein the functionally active CDR variant comprises at least one of a) 1, 2, or 3 point mutations in the parent CDR sequence, preferably wherein the number of point mutations in each of the CDR sequences is either 0, 1, 2, or 3; and/or
b) 1 or 2 point mutations in any of the four C-terminal or four N-terminal, or four centric amino acid positions of the parent CDR sequence; and/or
c) at least 60% sequence identity with the parent CDR sequence;

preferably wherein the functionally active variant antibody comprises at least one of the functionally active CDR variants as described herein. Specifically, the functionally active variant antibody comprising one or more of the functionally active CDR variants has a specificity to bind the same epitope as the parent antibody.

According to a specific aspect, a point mutation is any of an amino acid substitution, deletion and/or insertion of one or more amino acids.

"Percent (%) amino acid sequence identity" with respect to antibody sequences is defined as the percentage of amino acid residues in a candidate sequence that are identical with the amino acid residues in the specific polypeptide sequence, after aligning the sequence and introducing gaps according to methods well known in the art, such as CLUSTALW (Chenna et al., Nucleic Acids Res., 31:3497, 2003), if necessary, to achieve the maximum percent sequence identity, and not considering any conservative substitutions as part of the sequence identity. Those skilled in the art can determine appropriate parameters for measuring alignment, including any algorithms needed to achieve maximal alignment over the full length of the sequences being compared.

An antibody variant is specifically understood to include homologs, analogs, fragments, modifications or variants with a specific glycosylation pattern, e.g., produced by glycoengineering, which are functional and may serve as functional equivalents, e.g., binding to the specific targets and with different functional properties. An antibody may be glycosylated or unglycosylated. For example, a recombinant antibody as described herein may be expressed in an appropriate mammalian cell to allow a specific glycosylation of the molecule as determined by the host cell expressing the antibody, or in a prokaryotic cell that lacks the glycosylation machinery, resulting in an unglycosylated protein.

The term "beta sheet" or "beta strand" of an antibody domain, in particular of a constant antibody domain, is herein understood in the following way. An antibody domain typically consists of at least two beta strands connected laterally by at least two or three backbone hydrogen bonds, forming a generally twisted, pleated sheet. A beta strand is a single continuous stretch of amino acids of typically 3 to 10 amino acids length adopting such an extended conformation and involved in backbone hydrogen bonds to at least one other strand, so that they form a beta sheet. In the beta sheet, the majority of beta strands are arranged adjacent to other strands and form an extensive hydrogen bond network with their neighbors in which the N—H groups in the backbone of one strand establish hydrogen bonds with the C═O groups in the backbone of the adjacent strands.

The structure of antibody constant domains, such as a CL (Cκ, Cλ,), CH1, CH2 or CH3 domain, is similar to that of variable domains, consisting of beta-strands connected by loops, some of which contain short alpha-helical stretches. The framework is mostly rigid and the loops are comparatively more flexible, as can be seen from the x-ray crystallographic B factors of various Fc crystal structures. An antibody constant domain typically has seven beta strands forming a beta-sheet (A-B-C-D-E-F-G), wherein the beta strands are linked via loops, three loops being located at the N-terminal tip of the domain (A-B, C-D, E-F), and further three loops being located at the N-terminal tip of the domain (B-C, D-E, F-G). A "loop region" of a domain refers to the portion of the protein located between regions of beta strands (for example, each CH3 domain comprises seven beta sheets, A to G, oriented from the N- to C-terminus).

Specifically, a pair of antibody domains, such as constant antibody domains, e.g., the CL/CH1 domain pair comprised in the scVHAb or HCAb described herein, or any antibody domain pairs of the Fc, is produced by connecting a binding surface involving the A, B and E strands, herein also referred to as the beta-sheet region of a first antibody domain which is brought into contact (i.e., paired) with the beta-sheet region of a second domain to produce a dimer.

In certain embodiments, antibody domains may be comprise wild-type amino acid sequences such as originating from animals (including human beings), or artificial comprising mutations, e.g., can have at least a portion of one or more beta strands replaced with heterologous sequences, such as to include mutations which facilitate pairing with another domain, e.g., interdomain disulfide bridges, such as connecting beta-sheet regions of two antibody domains, knob and/or hole mutations, or strand-exchange.

Specific domain mutations can include the incorporation of new (additional) amino acid residues, e.g., Cys residues, which are capable of forming additional interdomain or interchain disulfide bridges to stabilize a) an antibody domain by an additional intradomain disulfide bonds, and/or
b) a domain pair by an interdomain disulfide bridge between a CL domain and a CH1 domain, e.g., in an antibody construct further described herein; and/or
c) two chains of antibody domains by additional interchain disulfide bridging.

Disulfide bonds are usually formed from the oxidation of thiol groups of two cysteines or other thiol forming amino acids or from the oxidation of thiol groups of amino acid analogues to form artificial disulfide bridges by linking the S-atoms of the amino acid side chains. Specifically, cysteine may be inserted (as an additional amino acid or an amino acid substitution) between a pair of domains that warrant the additional cysteine modifications to thereby produce a stabilized domain pair by disulfide bond formation.

A "pair" of antibody domains is understood as a set of two antibody domains in a certain arrangement, wherein one has an area on its surface or in a cavity that it specifically binds to and is therefore complementary to an area on the other one. Antibody domains may associate to form a pair of domains through contact of a beta-sheet region. Such a domain pair is also referred to as a (hetero- or homo-) dimer, which is e.g., associated by electrostatic interaction, recombinant fusion or covalent linkage, placing two domains in direct physical association. Specifically described herein is a CL/CH1 dimer of a scVHAb, which is a cognate pair of a CL domain and a CH1 domain. For stability reasons, such a CL/CH1 pair is particularly further connected through the peptide linker L2, thereby turning the pair into a single covalent polypeptide chain. In addition, a covalent disulfide bridge between the CL and CH1 domains can be introduced, stabilizing the pair of domain interactions The term "cognate" with respect to a pair of associated domains or domain dimers is understood as domains, each of which has a mutually complementary binding interface to create an interdomain contact surface on each of the domains. Upon contacting each other, the pair of domains is formed through association of these contact surfaces.

Antibodies may be produced by first screening the antigen-binding sites formed by folding the CDR sequences in each binding site of an antibody library to select specific binders. As a next step, the selected library members may serve as a source of CDR sequences (or parent CDR sequences, which may be further modified to modulate the antigen binding and even phenotypic properties) which may be used to engineer any kind of antibody constructs, e.g., full-length immunoglobulins or antigen-binding fragments thereof.

A library of antibodies (such as comprising a repertoire of specific antibody constructs recognizing the same target antigen, or a naïve library of antibodies which is produced by a certain animal or breed, e.g., the transgenic non-human animal described herein, which library comprises a repertoire of antibodies recognizing different target antigens) refers to a set or a collection of antibodies (e.g., scVHAbs or HCAbs described herein), each antibody being displayed appropriately in the chosen display system or containments.

Specific display systems couple a given protein, herein the antibody, e.g., scVHAbs or HCAbs described herein, with its encoding nucleic acid, e.g., its encoding mRNA, cDNA or genes. Thus, each member of a library comprises a nucleic acid encoding the antibody which is displayed thereon. Display systems encompass, without being limited to, cells, virus such as phages, ribosomes, eukaryotic cells such as yeast, DNAs including plasmids, and mRNAs.

Any antibody gene diversity library may be used for such purposes, which, e.g., includes a high number of individual library members, to create a diversity of antibody sequences, or employing preselected libraries, which are e.g., enriched in stabilized or functionally active library members. For example, a display system can be enriched in library members that bind to a certain target.

Libraries can be constructed by well-known techniques, involving, for example, chain-shuffling methods. For heavy chain shuffling, the antibodies are cloned into a vector containing, e.g., a human VH gene repertoire to create phage antibody library transformants. Further methods involve site-directed mutagenesis of CDRs of the antibodies, or CDR randomization where partial or entire CDRs are randomized, using either total randomization of targeted residues with the application of NNK codon-containing mutagenic oligonucleotides, or partial randomization of the targeted residues using parsimonious mutagenesis, where the oligonucleotides at positions encoding for targeted amino acid residues contain a mixture biased towards the original nucleotide base. Alternatively, the library can be constructed using error-prone PCR, with the application of dNTP analogs, error-prone polymerase, or the addition of $Mn^{2+}$ ions in the PCR reaction.

Various techniques are available for the manufacture of genes encoding the designs of human antibody library construction. It is possible to produce the DNA by a completely synthetic approach, in which the sequence is divided into overlapping fragments which are subsequently prepared as synthetic oligonucleotides These oligonucleotides are mixed together and annealed to each other by first heating to ca. 100° C. and then slowly cooling down to ambient temperature. After this annealing step, the synthetically assembled gene can be either cloned directly or it can be amplified by PCR prior to cloning. This is particularly desirable when a large single-pot human library is desirable and enormous resources are available for the construction process.

Specific methods employ phage, phagemid and/or yeast libraries for direct binder selection and internalizing phage antibody selection. Further methods for site directed mutagenesis can be employed for generation of the library insert, such as the Kunkel method (Kunkel, Proc. Natl. Acad. Sci. USA., 82:488, 1985) or the Dpnl method [Weiner, et al., Gene 151:119, 1994).

A "naïve library" refers to a library of polynucleotides (or polypeptides encoded by such polynucleotides) that has not been interrogated for the presence of antibodies having specificity to a particular antigen. A "naïve library" also refers to a library that is not restricted to, or otherwise biased or enriched for, antibody sequences having specificity for any group of antigens, or for a particular antigen. A naïve library is thus distinct from a "maturation library" (such as, for example, an "affinity maturation library").

A naïve library may also comprise a "preimmune" library, which refers to a library that has sequence diversity similar to naturally-occurring antibody sequences before such naturally occurring sequences have undergone antigen selection. Such preimmune libraries may be designed and prepared so as to reflect or mimic the pre-immune repertoire, and/or may be designed and prepared based on rational design informed by the collection of V, D, and J genes, and other large databases of heavy chain sequences (e.g., publicly known germline sequences). In certain embodiments of the invention, cassettes representing the possible V, D, and J diversity found in the human or non-human repertoire, as well as junctional diversity (i.e., N1 and N2), are synthesized de novo as single or double-stranded DNA oligonucleotides.

A "maturation library" refers to a library that is designed to enhance or improve at least one characteristic of an antibody sequence that is identified upon interrogation of a library, such as a naïve library or a preimmune library, for the presence of antibody sequences having specificity for the antigen. Such maturation libraries may be generated by incorporating nucleic acid sequences corresponding to: one or more CDRs; one or more antigen binding regions; one or more VH regions; and/or one or more heavy chains; obtained from or identified in an interrogation of a naïve library into libraries designed to further mutagenize in vitro or in vivo to generate libraries with diversity introduced in the context of an initial (parent) antibody.

As a different example of array technology, B-cell cloning can be used that yields genes encoding antibody constructs described herein, at manually or computer-addressable locations in an array of B-cells. Robotics or manual methods can be used to manipulate this array to re-array only cells expressing a certain type of antibodies and/or those that specifically recognize a certain target.

In certain embodiments, B-cell cloning, e.g., from suitably immunized non-human transgenic animals, such as those described herein, which are genetically engineered to produce antibodies, or mammalian cell expression libraries are used, or alternatively a large population of stably transformed mammalian cells are generated by the standard methods and robotic tools of antibody and protein engineering. Individual clones are kept viable in addressable wells arrayed on plates in suitable incubators and/or under long-term storage conditions, e.g., that may comprise freezing cell suspensions in liquid nitrogen with storage at −135° C., or under other acceptable conditions that allow recovery of the stored cell lines.

The term "repertoire" as used herein shall refer to a collection of variants, such as variants characterized by a diversity of target epitope or antigen specificities. Typically, the structure of an antibody (also called "scaffold") is the same in such repertoire, yet with a variety of different CDR sequences.

As is well-known in the art, there are a variety of display and selection technologies that may be used for the identification and isolation of proteins with certain binding characteristics and affinities, including, for example, display technologies such as cellular and non-cellular methods and in particular mobilized display systems. Among the cellular systems, the phage display, virus display, yeast or other eukaryotic cell display, such as mammalian or insect cell display may be used. Mobilized systems relate to display systems in a soluble format, such as in vitro display systems, among them ribosome display, mRNA display or nucleic acid display.

Screening the library for library members displaying an antigen-binding structure able to bind the target may be done by any suitable method. The screening step may comprise one or several rounds of selection.

Any screening method suitable for identifying antibodies able to bind the target antigen may be used. In particular, the rounds of selection may comprise incubating the library in the presence of said target so as to select the antibodies that bind said antigen, or an epitope thereof.

Once antibodies with the desired structure are identified, such antibodies can be produced by methods well-known in the art, including, for example, hybridoma techniques or recombinant DNA technology.

In the hybridoma method, an appropriate non-human host animal, such as a rodent or mouse, is immunized to activate lymphocytes that produce or are capable of producing antibodies that will specifically bind to the protein used for immunization. Alternatively, lymphocytes may be immunized in vitro. Lymphocytes then are fused with plasmacytoma cells using a suitable fusing agent, such as polyethylene glycol, to form a hybridoma cell.

Culture medium in which hybridoma cells are growing is assayed for production of monoclonal antibodies directed against the antigen. Preferably, the binding specificity of monoclonal antibodies produced by hybridoma cells is determined by flow cytometry, immunoprecipitation or by an in vitro binding assay, such as an enzyme-linked immunosorbent assay (ELISA).

According to another specific example, recombinant monoclonal antibodies can be produced by isolating the DNA encoding the required antibody chains and transfecting a recombinant host cell with the coding sequences for expression, using well-known recombinant expression vectors, e.g., the plasmids or expression cassette(s) comprising the nucleotide sequences encoding the antibody sequences. Recombinant host cells can be prokaryotic and eukaryotic cells.

According to a specific aspect, the coding nucleotide sequence may be used for genetic manipulation to humanize the antibody or to improve the affinity, or other characteristics of the antibody. For example, the constant region may be engineered to resemble human constant regions. It may be desirable to genetically manipulate the antibody sequence to obtain greater affinity to the target antigen. It will be apparent to one of skill in the art that one or more polynucleotide changes can be made to the antibody and still maintain its binding ability to the target (epitope or antigen).

The production of antibody molecules, by various means, is generally well understood. Various techniques relevant to the production of antibodies are provided in, e.g., Harlow, et al., Antibodies: A Laboratory Manual, 2$^{nd}$ Ed., Cold Spring Harbor Laboratory Press, Cold Spring Harbor, N.Y., (2014).

Monoclonal antibodies can e.g., be produced using any method that produces antibody molecules by continuous cell lines in culture. Examples of suitable methods for preparing monoclonal antibodies include the hybridoma methods of Kohler, et al., Nature 256:495, 1975) and the human B-cell hybridoma method [Kozbor, J. Immunol. 133:3001, 1984; and Brodeur, et al., 1987, in Monoclonal Antibody Production Techniques and Applications, LB Schook, ed., (Marcel Dekker, Inc., New York), pp. 51-63].

The term "target" as used herein shall refer to epitopes or antigens.

The term "antigen" as used herein shall in particular include all antigens and target molecules that have been shown to be recognised by a binding site of an antibody (at least one paratope) as a result of exposure of the antigen to the immune system of an animal or to a library of antibodies. Specifically, preferred antigens as targeted by the antibody described herein are those molecules that have already been proven to be or are capable of being immunologically or therapeutically relevant, especially those, for which a clinical efficacy has been tested.

The term "antigen" is used to describe a whole target molecule or a fragment of such molecule, especially substructures, e.g., a polypeptide or carbohydrate structure of targets. Such substructures, which are often referred to as "epitopes", e.g., B-cell epitopes, T-cell epitopes), can be immunologically relevant, i.e., are also recognizable by natural or monoclonal antibodies.

The term "epitope" as used herein shall in particular refer to a molecular structure present at the interface between the antigen and a specific antibody wherein the antibody surface of interaction with the epitope is referred to as the "paratope". Chemically, an epitope may be composed of a carbohydrate sequence or structure, a peptide sequence or set of sequences in a discontinuous epitope, a fatty acid or an oligo- or polynucleotide. Where the antigenic molecule is an organic, biochemical or inorganic substance it is referred to as a "hapten". Epitopes or haptens may consist of derivatives or any combinations of the above substances. If an epitope is a polypeptide, it will usually include at least 3 amino acids, preferably 8 to 50 amino acids, and more preferably between about 10-20 amino acids in the peptide. Epitopes can be either linear or discontinuous epitopes. A linear epitope is comprised of a single segment of a primary sequence of a polypeptide or carbohydrate chain. Linear epitopes can be contiguous or overlapping. Discontinuous epitopes are comprised of amino acids or carbohydrates brought together by folding the polypeptide to form a tertiary structure and the amino acids are not necessarily adjacent to one another in the linear sequence. Specifically, epitopes are at least part of diagnostically relevant molecules, i.e., the absence or presence of an epitope in a sample is qualitatively or quantitatively correlated to either a disease or to the health status of a patient or to a process status in manufacturing or to environmental and food status. Epitopes may also be at least part of therapeutically relevant molecules, i.e., molecules that can be targeted by the specific binding domain, which changes the course of the disease.

As used herein, the term "specificity" or "specific binding" refers to a binding reaction which is determinative of the cognate ligand of interest in a heterogeneous population of molecules. Thus, under designated conditions (e.g., immunoassay conditions), the antibody binds to its particular target and does not bind in a significant amount to other molecules present in a sample. The specific binding means that binding is selective in terms of target identity, high, medium or low binding affinity or avidity, as selected. Selective binding is usually achieved if the binding constant or binding dynamics is at least 10-fold different than a competing target in the sample, preferably the difference is at least 100-fold, and more preferred a least 1000-fold.

A specific binding does not exclude certain cross-reactivity with similar antigens, or the same antigens of a different species (analogues). For example, a binding entity may also preferably cross-react with rodent or primate targets analogous to human targets to facilitate preclinical animal studies.

The term "locus" as used herein refers to a DNA coding sequence or segment of DNA that code for an expressed product, i.e., a genomic sequence, such as part of a genome of a host organism, or part of a vector, e.g., integrated at a target site, such as at defined restriction sites or regions of homology.

Restriction sites can be designed to ensure insertion of an expression cassette in the proper reading frame. Typically, foreign (herein also referred to as exogenous) DNA is inserted at one or more restriction sites of a vector DNA, and then is carried by the vector into a host cell along with the transmissible vector DNA.

Typically, a locus encompasses at least one gene. The term "locus" does not imply that a gene is actively transcribed or intact. Genes may be encompassed that have been inactivated.

In specific embodiments described herein, the transgenic animal's endogenous kappa and lambda light chain loci are non-functional by one or more modifications, such as loss-of function mutations, or deletion of endogenous κ and/or λ light chain loci, or parts thereof.

Exemplary suitable modifications are understood as follows. To inactivate the kappa chain locus, the entire 3.2 Mb genomic region between Vκ2-137, the most C distal Vκ gene segment, and Jκ5, the most Cκ proximal Jκ is deleted by a recombinase mediated cassette exchange (RMCE) strategy. This is done by insertion of appropriate targeting sequences upstream of Vκ2-137 and downstream of Jκ5, followed by in vitro Cre-mediated deletion of the intervening genomic region. A similar strategy is used to inactivate the lambda chain locus. The entire 194 Kb region containing the mouse lambda V gene segments (IgIV) is deleted by RMCE. In this case, the appropriate targeting sequences are inserted upstream of IgIV2 and downstream of IgIV1, followed by in vitro Cre-mediated deletion of the intervening genomic region.

A locus may be engineered to express exons encoding an antibody, such as further described herein.

A recombinant locus can be created using various conventional techniques for site-specific editing and/or recombination. Preferably, a modified locus is generated by inserting a piece of DNA (referred to here as the "donor DNA") containing gene segments encoding, e.g., CL-L2-CH1 into a modified version of a non-human animal immunoglobulin locus such as a heavy chain locus of a host organism (referred to here as the "acceptor allele"). The acceptor allele may contain recognition sites for a site-specific DNA recombinase, such as the Cre recombinase (a loxP site and a mutated version of the loxP site). The donor DNA may be flanked by the same Cre recombinase recognition sites (at both, the 5'-end and the 3'-end, e.g., on one side there is a loxP site and on the other there will be a mutated version of the loxP site). The Cre recombinase may be used to catalyze the insertion of the donor DNA into the acceptor allele.

In an alternative embodiment, gene segments are introduced into an immunoglobulin locus primarily, if not exclusively, by homologous recombination. In such an embodiment, targeting sequences or vectors are employed that are comprised of genomic targeting homology arms flanking a nucleic acid sequence comprising antibody encoding gene segments (i.e., a nucleotide sequence at both, the 5'-end and the 3'-end, which is homologous to and capable of hybridizing with a target sequence). These genomic homology arms facilitate insertion of the antibody encoding DNA into an immunoglobulin locus, such as DNA that encodes the immunoglobulin heavy chain.

The term "targeting sequence" refers to a sequence that is homologous to DNA sequences in the genome of a cell that flank or occur adjacent to the region of an immunoglobulin genetic locus that is to be modified. The flanking or adjacent sequence may be within the locus itself or upstream or downstream of coding sequences in the genome of the host cell. Targeting sequences are inserted into recombinant DNA vectors for use in cell transfections such that sequences to be inserted into the cell genome, such as the sequence of a recombination site, are flanked by the targeting sequences of the vector.

In many instances in which homologous recombination is employed to accomplish a genetic change in a genome, such as an insertion or a deletion, a further modification would involve the use of engineered site-specific endonucleases to increase the likelihood that a desired outcome can be accomplished. Such endonucleases are of value because they can be engineered to be highly specific for unique sequences in a target genome and because they cause double-stranded DNA breaks at the sites they recognize. Double-stranded breaks promote homologous recombination with targeting vectors that carry targeting homology with DNA in the immediate vicinity of the breaks. Thus, the combination of a targeting vector and a site-specific endonuclease that cleaves DNA within or close to the region targeted by a vector typically results in much higher homologous recombination efficiency than use of a targeting vector alone. Furthermore, it is possible to facilitate the creation of a genomic deletion through use of one or more site-specific endonucleases and a targeting vector comprised of two targeting homology arms in which one arm targets one side of the region to be deleted and the other arm targets the other side.

Site-specific recombination differs from general homologous recombination in that short specific DNA sequences, which are required for the recombinase recognition, are the only sites at which recombination occurs. Site-specific recombination requires specialized recombinases to recognize the sites and catalyze the recombination at these sites. A number of bacteriophage- and yeast-derived site-specific recombination systems, each comprising a recombinase and specific cognate target sites, have been shown to work in eukaryotic cells for the purpose of DNA integration and are therefore applicable for use as described herein. These include the bacteriophage P1 Cre/lox, yeast FLP-FRT system, and the Dre system of the tyrosine family of site-specific recombinases. Such systems and methods of use are well-described in the prior art. The recombinase-mediated cassette exchange (RMCE) procedure is facilitated by usage of the combination of wild-type and mutant loxP (or FRT, etc.) sites together with the appropriate recombinase (e.g., Cre or Flp), and negative and/or positive selection. RMCE will occur when the sites employed are identical to one another and/or in the absence of selection, but the efficiency of the process is reduced because excision rather than insertion reactions are favored, and (without incorporating positive selection) there will be no enrichment for appropriately mutated cells.

Other systems of the tyrosine family such as bacteriophage lambda Int integrase, HK2022 integrase, and in addition systems belonging to the separate serine family of recombinases such as bacteriophage phiC31, R4Tp901 integrases are known to work in mammalian cells using their respective recombination sites and are also applicable for use as described herein.

The methods described herein specifically utilize site-specific recombination sites that utilize the same recombinase, but which do not facilitate recombination between the sites. For example, a loxP site and a mutated loxP site can be integrated into the genome of a host, but introduction of Cre into the host will not cause the two sites to undergo recombination; rather, the loxP site will recombine with another loxP site, and the mutated site will only recombine with another likewise mutated loxP site.

Two classes of variant recombinase sites are available to facilitate recombinase-mediated cassette exchange. One harbors mutations within the 8 bp spacer region of the site, while the other has mutations in the 13-bp inverted repeats.

Spacer mutants such as lox511 (Hoess, et al., Nucleic Acids Res., 14:2287, 1986), Iox5171 and lox2272 (Lee and Saito, Gene, 216:55, 1998), m2, m3, m7, and mil (Langer, et al., Nucleic Acids Res., 30:3067, 2002) recombine readily with themselves but have a markedly reduced rate of recombination with the wild-type site. Examples of the use of mutant sites of this sort for DNA insertion by recombinase-mediated cassette exchange can be found in Baer and Bode, Curr. Opin. Biotechnol., 12:473, 2001.

Inverted repeat mutants represent a second class of variant recombinase sites. For example, loxP sites can contain altered bases in the left inverted repeat (LE mutant) or the right inverted repeat (RE mutant). A LE mutant, lox71, has 5 bp on the 5' end of the left inverted repeat that is changed from the wild type sequence to TACCG (Araki, Nucleic Acids Res., 25:868, 1997). Similarly, the RE mutant, lox66, has the five 3'-most bases changed to CGGTA. Inverted repeat mutants can be used for integrating plasmid inserts into chromosomal DNA. For example, the LE mutant can be used as the "target" chromosomal loxP site into which the "donor" RE mutant recombines. After recombination, a donor piece of DNA that contained a RE site will be found inserted in the genome flanked on one side by a double mutant site (containing both the LE and RE inverted repeat mutations) and on the other by a wild-type site (Lee and Sadowski, Prog. Nucleic Acid Res. Mol. Biol., 80:1, 2005). The double mutant is sufficiently different from the wild-type site that it is unrecognized by Cre recombinase and the inserted segment therefore cannot be excised by Cre-mediated recombination between the two sites.

In certain aspects, site-specific recombination sites can be introduced into introns or intergenic regions, as opposed to coding nucleic acid regions or regulatory sequences. This may avoid inadvertently disrupting any regulatory sequences or coding regions necessary for proper gene expression upon insertion of site-specific recombination sites into the genome of the animal cell.

Introduction of the site-specific recombination sites may be achieved by conventional homologous recombination techniques. Such techniques are described in references such as e.g., Sambrook and Russell (2001) *Molecular cloning: a laboratory manual*, 3*d* ed. (Cold Spring Harbor, N.Y.: Cold Spring Harbor Laboratory Press) and Nagy, (2003) *Manipulating the mouse embryo: a laboratory manual,* 3d ed. (Cold Spring Harbor, N.Y.: Cold Spring Harbor Laboratory Press).

Specific recombination into the genome can be facilitated using vectors designed for positive or negative selection as known in the art. In order to facilitate identification of cells that have undergone the replacement reaction, an appropriate genetic marker system may be employed, and cells selected by, e.g., use of a selection medium. However, in order to ensure that the genome sequence is substantially free of extraneous nucleic acid sequences at or adjacent to the two end points of the replacement interval, desirably the marker system/gene can be removed following selection of the cells containing the replaced nucleic acid.

The recombinase may be provided as a purified protein or may be expressed from a construct transiently expressed within the cell in order to provide the recombinase activity. Alternatively, the cell may be used to generate a transgenic animal, which may be crossed with an animal that expresses said recombinase, in order to produce progeny that lack the marker gene and associated recombination sites.

Herein the term "endogenous", with reference to a gene, indicates that the gene is native to a cell, i.e., the gene is present at a particular locus in the genome of a non-modified cell. An endogenous gene may be a wild type gene present at that locus in a wild type cell (as found in nature). An endogenous gene may be a modified endogenous gene if it is present at the same locus in the genome as a wild type gene. An example of such a modified endogenous gene is a gene into which a foreign nucleic acid is inserted. An endogenous gene may be present in the nuclear genome, mitochondrial genome, etc.

In an alternative embodiment, gene segments are introduced into an immunoglobulin locus, by a CRISPR/Cas9 technology using a non-homologous end joining approach, e.g., see He, et al., Nuc. Acids Res., 44:e85, 2016, rather than by homology directed repair typically used with this system.

"Vectors" used herein are defined as DNA sequences that are required for the transcription of cloned recombinant nucleotide sequences, i.e., of recombinant genes and the translation of their mRNA in a suitable host organism. A vector includes plasmids and viruses and any DNA or RNA molecule, whether self-replicating or not, which can be used to transform, transduce or transfect a cell. A vector may include autonomously replicating nucleotide sequences as well as genome integrating nucleotide sequences. Expression vectors may additionally comprise an origin for autonomous replication in the host cells or a genome integration site, one or more selectable markers (e.g., an amino acid synthesis gene or a gene conferring resistance to antibiotics such as puromycin, Zeocin™ kanamycin, G418 or hygromycin), a number of restriction enzyme cleavage sites, a suitable promoter sequence and a transcription terminator, which components are operably linked together.

A common type of vector is a "plasmid", which generally is a self-contained molecule of double-stranded DNA that can readily accept additional (foreign) DNA and which can readily be introduced into a suitable host cell. A plasmid often contains coding DNA and promoter DNA and has one or more restriction sites suitable for inserting foreign DNA. Specifically, the term "plasmid" refers to a vehicle by which a DNA or RNA sequence (e.g., a foreign gene) can be introduced into a host cell, so as to transform the host and promote expression (e.g., transcription and translation) of the introduced sequence.

The term "host cell" as used herein shall refer to primary subject cells transformed to produce a particular recombinant protein, such as an antibody as described herein, and any progeny thereof. It should be understood that not all progeny are exactly identical to the parental cell (due to deliberate or inadvertent mutations or differences in environment), however, such altered progeny are included in these terms, so long as the progeny retain the same functionality as that of the originally transformed cell. The term "host cell line" refers to a cell line of host cells as used for expressing a recombinant gene to produce recombinant polypeptides such as recombinant antibodies. The term "cell line" as used herein refers to an established clone of a particular cell type that has acquired the ability to proliferate over a prolonged period of time. Such host cell or host cell line may be maintained in cell culture and/or cultivated to produce a recombinant polypeptide.

The term "isolated" or "isolation" as used herein with respect to a nucleic acid, an antibody or other compound shall refer to such compound that has been sufficiently separated from the environment with which it would naturally be associated, so as to exist in "substantially pure" form. "Isolated" does not necessarily mean the exclusion of artificial or synthetic mixtures with other compounds or materials, or the presence of impurities that do not interfere with the fundamental activity, and that may be present, for example, due to incomplete purification. In particular, isolated nucleic acid molecules as described herein are also meant to include those chemically synthesized.

With reference to nucleic acids as described herein, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism. When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An "isolated nucleic acid" (either DNA or RNA) may further represent a molecule produced directly by biological or synthetic means and separated from other components present during its production.

With reference to polypeptides or proteins, such as isolated antibodies, the term "isolated" shall specifically refer to compounds that are free or substantially free of material with which they are naturally associated such as other compounds with which they are found in their natural environment, or the environment in which they are prepared, e.g., cell culture, when such preparation is by recombinant DNA technology practiced in vitro or in vivo. Isolated compounds can be formulated with diluents or adjuvants and still for practical purposes be isolated—for example, the polypeptides or polynucleotides can be mixed with pharmaceutically acceptable carriers or excipients when used in diagnosis or therapy.

Antibodies described herein are particularly provided in the isolated form, which are substantially free of other antibodies directed against different target antigens and/or comprising a different structural arrangement of antibody domains. Still, an isolated antibody may be comprised in a combination preparation, containing a combination of the isolated antibody, e.g., with at least one other antibody, such as monoclonal antibodies or antibody fragments having different specificities.

Specifically, the antibody as described herein is provided in substantially pure form. The term "substantially pure" or "purified" as used herein shall refer to a preparation comprising at least 50% (w/w), preferably at least 60%, 70%, 80%, 90%, or 95% of a compound, such as a nucleic acid molecule or an antibody. Purity is measured by methods appropriate for the compound (e.g., chromatographic methods, polyacrylamide gel electrophoresis, HPLC analysis, and the like).

The antibody as described herein may specifically be used in a pharmaceutical composition. Therefore, a pharmaceutical composition is provided which comprises an antibody as described herein and a pharmaceutically acceptable carrier or excipient. These pharmaceutical compositions can be administered in accordance with the present invention as a bolus injection or infusion or by continuous infusion. Pharmaceutical carriers suitable for facilitating such means of administration are well-known in the art.

Pharmaceutically acceptable carriers generally include any and all suitable solvents, dispersion media, coatings, isotonic and absorption delaying agents, and the like that are physiologically compatible with an immunoglobulin provided by the invention. Further examples of pharmaceutically acceptable carriers include sterile water, saline, phosphate buffered saline, dextrose, glycerol, ethanol, and the like, as well as combinations of any thereof.

Additional pharmaceutically acceptable carriers are known in the art and described in, e.g., Remington's Pharmaceutical Sciences (Gennaro, AR, ed., Mack Printing Co). Liquid formulations can be solutions, emulsions or suspensions and can include excipients such as suspending agents, solubilizers, surfactants, preservatives, and chelating agents.

Exemplary formulations as used for parenteral administration include those suitable for subcutaneous, intramuscular or intravenous injection as, for example, a solution, emulsion or suspension.

The term "therapeutically effective amount", used herein with respect to administration of a compound, e.g., an antibody as described herein, is a quantity or activity sufficient to effect beneficial or desired results, including clinical results, when administered to the subject. As such, an effective amount or synonymous quantity thereof depends upon the context in which it is being applied.

An effective amount is intended to mean that amount of a compound that is sufficient to treat, prevent or inhibit such diseases or disorders. In the context of disease, therapeutically effective amounts of the antibody as described herein are specifically used to treat, modulate, attenuate, reverse, or affect a disease or condition that benefits from the interaction of the antibody with its target antigen.

The amount of the compound that will correspond to such an effective amount will vary depending on various factors, such as the given drug or compound, the pharmaceutical formulation, the route of administration, the type of disease or disorder, the identity of the subject or host being treated, and the like, but can nevertheless be routinely determined by one skilled in the art.

The term "recombinant" refers to a polynucleotide or polypeptide that does not naturally occur in a host cell. A recombinant molecule may contain two or more naturally-occurring sequences that are linked together in a way that does not occur naturally. A recombinant cell contains a recombinant polynucleotide or polypeptide. If a cell receives a recombinant nucleic acid, the nucleic acid is "exogenous" to the cell.

The term "recombinant" particularly means "being prepared by or the result of genetic engineering". Alternatively, the term "engineered" is used. For example, an antibody or antibody domain may be modified to produce a variant by engineering the respective parent sequence to produce an engineered antibody or domain. A recombinant host specifically comprises an expression vector or cloning vector, or it has been genetically engineered to contain a recombinant nucleic acid sequence, in particular employing nucleotide sequence foreign to the host. A recombinant protein is produced by expressing a respective recombinant nucleic acid in a host. The term "recombinant antibody", as used herein, includes immunoglobulins and in particular antibodies that are prepared, expressed, created, or isolated by recombinant means, such as a) antibodies isolated from an animal (e.g., a non-human animal, such as a mouse) that is transgenic or transchromosomal for human immunoglobulin genes or a hybridoma prepared therefrom, b) antibodies isolated from a host cell transformed to express the antibody, e.g., from a transfectoma, c) antibodies isolated from a recombinant, combinatorial antibody library, and d) antibodies prepared, expressed, created or isolated by any other means that involve splicing of, e.g., human immunoglobulin gene sequences to other DNA sequences. Such recombinant antibodies comprise antibodies engineered to include rearrangements and mutations that occur, for example, during antibody maturation.

"Site-specific recombination" refers to a process of recombination between two compatible recombination sites including any of the following three events:

a) deletion of a preselected nucleic acid flanked by the recombination sites;
b) inversion of the nucleotide sequence of a preselected nucleic acid flanked by recombination sites, and
c) reciprocal exchange of nucleic acid regions proximate to recombination sites located on different nucleic acid molecules. It is to be understood that this reciprocal exchange of nucleic acid segments results in an integration event if one or both of the nucleic acid molecules are circular.

The term "transgene" is used herein to describe genetic material that has been or is about to be artificially inserted into the genome of a cell, and particularly a cell of a host animal. The term "transgene" as used herein refers to a nucleic acid molecule, e.g., a nucleic acid in the form of an expression construct and/or a targeting vector.

"Transgenic animal" is meant a non-human animal, usually a mammal or avian, e.g., a rodent, particularly a mouse or rat, although other mammals are envisioned, having an exogenous nucleic acid sequence present as a chromosomal or extrachromosomal element in a portion of its cells or stably integrated into its germ line DNA (i.e., in the genomic sequence of most or all of its cells).

In certain aspects of the embodiments, the transgenic animals of the invention further comprise human immunoglobulin regions. For example, numerous methods have been developed for replacing endogenous mouse immunoglobulin regions with human immunoglobulin sequences to create partially- or fully-human antibodies for drug discovery purposes. Examples of such mice include those described in, for example, U.S. Pat. Nos. 7,145,056; 7,064,244; 7,041,871; 6,673,986; 6,596,541; 6,570,061; 6,162,963; 6,130,364; 6,091,001; 6,023,010; 5,593,598; 5,877,397; 5,874,299; 5,814,318; 5,789,650; 5,661,016; 5,612,205; and 5,591,669.

In the particularly favored aspects, the transgenic animals of the invention comprise chimeric immunoglobulin segments as described in US Pub. No. 2013/0219535 by Wabl and Killeen. Such transgenic animals have a genome comprising an introduced partially human immunoglobulin region, where the introduced region comprising human variable region coding sequences and non-coding variable sequences based on the endogenous genome of the non-human vertebrate. Preferably, the transgenic cells and animals of the invention have genomes in which part or all of the endogenous immunoglobulin region is removed.

In another favored aspect, the genomic contents of animals are modified so that their B cells are capable of expressing more than one functional VH domain per cell, i.e., the cells produce bispecific antibodies, as described in WO2017035252A1.

The foregoing description will be more fully understood with reference to the following examples. Such examples are, however, merely representative of methods of practicing one or more embodiments of the present invention and should not be read as limiting the scope of invention.

EXAMPLES

EXAMPLE 1: Estimation of minimum linker 2 length based on the crystal structure of an IgG Fab fragment. Linker 2 (L2, FIG. 2) connects CL (Cκ or Cλ) to CH1. Based on the Fab structure shown in FIG. 3 [PDB 2XKN, crystal structure of the Fab fragment of the EGFR (epidermal growth factor receptor) antibody 7A7, an IgG1κ mAb], the distance to be bridged to connect the COOH-terminus of Cκ and the $NH_2$-terminus of CH1 is 40.9 Å (indicated by the dashed line in FIG. 3). Due to the relative position of Cκ and CH1, the linker has to be longer in order to connect the C- and N-termini. The theoretical length of a (GGGGS [SEQ ID NO:35]$)_4$ linker is 76 Å, which is less than twice the coverage of the distance between the two termini (81.8 Å). Therefore, the minimum suggested linker length in this case is (GGGGS [SEQ ID NO:35]$)_4$ and the maximum is (GGGGS [SEQ ID NO:35]$)_{16}$.

EXAMPLE 2: In vitro testing of expression vectors encoding HCAbs Prior to generation of transgenic mice expressing the scVHAb or HCAb, a variety of expression vectors encoding the transmembrane and secreted forms of the HCAb were constructed and tested for expression in vitro. These various constructs differ in several respects—L2 length, composition of CL (Cκ, Cλ1 or Cλ2), composition of CH (IgG1 or IgG2a), and the order of the CL and CH1 domains in the encoded HCAb protein (NH-VH-Cκ-L2-CH1-CH2-CH3-TM-COOH versus NH—VH-CH1-L2-Cκ-CH2-CH3-TM-COOH). Several positive and negative control vectors were also constructed and tested: Positive controls known to be expressed on the cell surface—a conventional H2L2 IgG antibody, a camel-like IgG lacking the CH1 domain and any LC, a scFV IgG antibody with a linked Vκ and VH but no CL or CH1. Negative control not expressed on the cell surface—a conventional IgG antibody but with no LC (H2L0).

The expression vectors were transfected into HEK 293T cells using Lipofectamine 2000 (Invitrogen). An expression vector encoding human CD4 with a myc-tag was co-transfected and hCD4 expression was used as a control for transfection efficiency. Additionally, all HEK 293T cells were co-transfected with a construct expressing both mouse CD79a and CD79b (Igα/Igβ), which are co-receptors required for the surface expression of antigen receptors including membrane-bound forms of HCAb (Wienands and Engles, Int. Rev. Immunol., 20:679, 2001). After 20-24 hrs, the cells were stained for cell surface hCD4, mouse IgG1 (mIgG1) and mouse κ light chain (mIgκ) and analyzed by flow cytometry for detection of cell surface and intracellular HCAb and hCD4 protein expression. For western blot (WB) detection of cell-associated myc, GAPDH and HCAb and secreted HCAb, cells were lysed and supernatants were collected 40-48 hrs after transfection. The same supernatants were also used to quantify secreted HCAb by ELISA.

The HCAb Containing Cκ is Expressed on the Cell Surface.

FIG. 4 depicts the expression vectors used in the first round of experiments. Positive controls: 1. Conventional H2L2 IgG antibody, 2. Camel-like IgG lacking the CH1 domain and LC, 3. scFV IgG antibody with a linked Vκ and VH but no CL or CH1. HCAb described herein: 4. NH-VH-Cκ-L2-CH1-CH2-CH3-TM-COOH. HCAb described herein but with the order of the Cκ and CH1 domains reversed in the HCAb: 5. NH—VH-CH1-L2-Cκ-CH2-CH3-TM-COOH. Neqative control: Conventional IgG antibody with no LC (H2L0).

FIG. 5 depicts analysis of cell surface expression of proteins of interest by flow cytometry. The frequency of cells expressing hCD4 was similar in all the transfected cell lines (range 61-64%), indicating a similar transfection efficiency in all cases (top row). As expected (middle row), the positive controls, conventional mIgG1 (1), camel-like Ab (2) and the scFv (3) were all expressed on the cell surface. The HCAb described herein (4) was similarly expressed; however, if the order of the Cκ and CH1 domains in the HCAb was reversed (5), there was no longer any cell surface expression. The mean fluorescent intensity (MFI) of cell surface mIgG1 staining, which correlates with expression levels, varied with the different constructs (Table 1). The negative control, conventional IgG1 with no light chains (6) was not expressed on the cell surface. As expected, expression of surface mIgκ was only observed with constructs 1 and 4 since they are the only surface-expressed HCAb containing CK. To ensure that the lack of cell surface mIgG1 expression was not because the protein was being degraded inside the cells, the transfectants were fixed, permeabilized and stained for intracellular proteins with the same panel of antibodies (FIG. 6, the MFI of intracellular mIgG1 staining for these samples is shown in Table 2). Cells transfected with constructs 5 and 6 contained abundant intracellular mIgG1 heavy chain but it was not expressed on the cell surface. Therefore, some active mechanism must be retaining these molecules inside of the cell. For the H2L0 HCAb encoded by construct 6, this retention is known to be caused by association of the partially unfolded CH1 domain with the ER chaperone BiP (Haas and Wabl, Nature, 306:387, 1983; Bole, et al., J Cell Biol. 102:1558, 1986).

TABLE 1

Mean Fluorescence Intensity (MFI) of cell surface mIgG1 staining. Data are from the flow cytometry analysis in FIG. 5.

| Construct Number | MFI |
|---|---|
| 1 | 3841 |
| 2 | 2729 |
| 3 | 5310 |
| 4 | 2965 |

TABLE 2

Mean Fluorescence Intensity (MFI) of intracellular mIgG1 staining. Data are from the flow cytometry analysis in FIG. 6.

| Construct Number | MFI |
|---|---|
| 1 | 5696 |
| 2 | 4240 |
| 3 | 6003 |
| 4 | 16467 |
| 5 | 1590 |
| 6 | 5736 |

HCAbs Containing Cλ1 or Cλ2 are Also Expressed on the Cell Surface.

The effect of altering the CL domain in the HCAb was also tested using the constructs depicted in FIG. 7A. Positive control construct 1 encodes the camel-like IgG1 and constructs 2-4 encode the HCAb described herein containing Cκ, Cλ1 and Cλ2, respectively. All HCAbs were expressed on the cell surface (FIG. 8, middle row) although the MFI varied (Table 3). Cλ3 was not tested here but the results are expected to be the same as with Cλ2 since the amino acid sequences of Cλ2 and Cλ3 are nearly identical (99% amino acid identity). A schematic of the fusion gene encoding construct 3 is shown in FIG. 7B. The VH exon in this construct is encoded by VH3-11, DH2-21 and JH4, the CL exon is encoded by Cλ1 and the CH and hinge (H) exons are from IgG1. Those skilled in the art will recognize that any VH, DH, JH, CL, or CH gene can be inserted to replace the respective components of the construct depicted here.

TABLE 3

Mean Fluorescence Intensity (MFI) of cell surface mIgG1 staining. Data are from the flow cytometry analysis in FIG. 8.

| Construct Number | MFI |
|---|---|
| 1 | 3072 |
| 2 | 2169 |
| 3 | 4565 |
| 4 | 3400 |

Secretion of the HCAbs

HEK 293T cells were also transfected with the secretory form of the constructs depicted in FIGS. 7A and 7B to test for HCAb secretion by WB (FIG. 9 and FIG. 10) and enzyme-linked immunoassay (ELISA, FIG. 12). The effect of changing the L2 length from 6 to 10 repeats and of changing the CH domain from IgG1 to IgG2a was also examined in these experiments. WB controls for transfection efficiency (anti-Myc antibody) and loading controls (anti-GAPDH antibody) are shown in FIG. 11.

The camel-like Ab showed the best secretion as evaluated by WB (FIG. 9 left, lane 1, non-reducing conditions, FIG. 10 left, lane 1, reducing conditions). Of the HCAb constructs examined, the one encoding mIgG1 with Cλ1 and a linker of 10 GGGGS (SEQ ID NO:35) repeats showed the best secretion (FIG. 9 left, lane 4, non-reducing conditions, FIG. 10 left, lane 4, reducing conditions). Increasing the linker length from 6 to 10 repeats also improved secretion of the VH-Cκ HCAb (compare lanes 2 and 3 in FIG. 9, left panel), presumably by improving folding of the hybrid HCAb molecule and its release from ER chaperones. HCAb secretion may be improved even more by further increasing the linker length. The relatively low level of HCAb secretion compared to the camel-like Ab may be due to the formation of intracellular protein complexes of the HCAb. These high molecular weight bands can be seen to be more abundant in the cell lysates of mIgG1 HCAb-expressing transfectants than in the camel-like lysates (FIG. 9, compare lane 1 with lanes 2-5 in the right panel). These are disulfide-linked complexes and not non-specific aggregates since they disappear under reducing conditions (FIG. 10, right panel).

An ELISA assay was used to quantify the HCAb in the same supernatants analyzed by WB (FIG. 12). In agreement with the WB data, the mIgG1 with Cλ1 and a linker of 10 GGGGS (SEQ ID NO:35) repeats showed the best secretion among the HCAbs (~840 ng/ml), which was only ~3.8 fold less than the camel-like antibody.

Example 3: Use of Homologous Recombination to Introduce a Mouse CL-L2-CH1-H-CH2-CH3 S-TM Gene Cassette into the Endogenous Mouse Igh Locus Upstream of Ighm for the Production of HCAbs An exemplary method for the introduction of the CL-L2-CH1-H-CH2-CH3_S-TM gene cassette for the generation of HCAbs is illustrated in FIG. 13.

The targeting vector is depicted in FIGS. 13A and 13B. (Note that the segments labeled A. and B. and connected by a dashed line in this figure are contiguous in the targeting vector.) The CL component of the cassette can encode either Cκ or Cλ (CM1, Cλ2 or Cλ3). (Note that the Linker 1-containing cassette, L1-CL-L2-CH1-H-CH2-CH3_S-TM, also described herein, can be introduced in an identical fashion.)

Two essential components of the homologous recombination targeting vector are the short homology arm (SHA) and the long homology arm (LHA), which share sequence identify with homologous DNA segments that flank the region of the endogenous locus that is being modified (FIG. 13C). In this case, the SHA consists of human JH2-JH6 gene segments flanked by the corresponding mouse Jh noncoding sequences (SEQ ID NO:2). The LHA consists of the entire Ighm gene, starting in the 5' intron and terminating at the 3' UTR (SEQ ID NO:21). Other notable features of the targeting vector beginning at the 5' end include: 1) Pgk_TK_pA (SEQ ID NO:1), a Herpes simplex virus (HSV) thymidine kinase (TK) gene driven by the phosphoglycerate kinase promoter (Pgk) and including a polyA site (pA). This element is used for negative selection with ganciclovir against cells that have integrated the targeting vector, but not by homologous recombination; such cells will retain the HSV-TK gene and be killed. 2) T3 promoter (SEQ ID NO:3) for the T3 bacteriophage RNA polymerase. This DNA-dependent RNA polymerase is highly specific for the T3 phage promoter. The 99 KD enzyme catalyzes in vitro RNA synthesis, which allows for rapid cloning of VDJ rearrangements from small numbers of B cells or hybridomas. 3) CAG_PuroR_pA, a puromycin resistance gene driven by the strong CAG promoter and including a polyA site (SEQ ID NO:5). This element is used for positive selection of cells that have integrated the targeting vector based on puromycin resistance. 4) Note that cells that have stably integrated the targeting vector into their genome will be resistant to both ganciclovir and puromycin. 5) Note that the CAG_PuroR_pA element is flanked by FRT sites (SEQ ID NO:4 and SEQ ID NO:6) that can be used, after identification of properly targeted ES cell clones, to remove this element in vitro or in vivo by supplying FIp recombinase. The Ep enhancer (SEQ ID NO:7) is included upstream of the CL-L2-CH1-H-CH2-CH3_S-TM gene cassette to promote transcription of the locus. This is followed in the targeting vector by the Ighm LHA (SEQ ID NO:21). The targeting vector lacks the μ switch (S) region present in the endogenous Igh locus so that the targeted locus will also lack the S region and thus be unable to undergo isotype switching. The targeting vector is introduced into the ES cells by electroporation. Cells are grown in media supplemented with ganciclovir and puromycin. Surviving isolated ES cell clones are then monitored for successful gene targeting by genomic PCR using widely practiced gene targeting strategies with primers located within, 5' and 3' of the newly introduced CL-L2-CH1-H-CH2-CH3_S-TM gene cassette. Proper integration of the targeting cassette is furtherer verified by genomic southern blots using a probe that maps to DNA sequence flanking the 5' side of the SHA, a second probe that maps to DNA sequence flanking the 3' side of the LHA and a third probe that maps within the novel DNA between the two arms of genomic identity in the vector. (The structure of the correctly targeted locus is depicted in FIGS. 13D and 13E. Note that the segments labeled D. and E. and connected by a dashed line in the figure are contiguous in the Igh locus in the ES cells.)

Karyotypes of PCR- and Southern blot-verified clones of ES cells are analyzed using an in situ fluorescence hybridization procedure designed to distinguish the most commonly arising chromosomal aberrations that arise in mouse ES cells. Clones with such aberrations are excluded from further use. ES cell clones that are judged to have the expected correct genomic structure based on the PCR and Southern blot data, and that also do not have detectable chromosomal aberrations based on the karyotype analysis, are selected for further use.

ES cell clones carrying the properly targeted CL-L2-CH1-H-CH2-CH3_S-TM gene cassette in the mouse heavy chain locus are microinjected into mouse blastocysts from strain DBA/2 to create partially ES cell-derived chimeric mice according to standard procedures. Male chimeric mice with the highest levels of ES cell-derived contribution to their coats are selected for mating to female mice. The female mice of choice here are of C57B1/6NTac strain, which carry a transgene encoding the Flp recombinase in their germline. Offspring from these matings are analyzed for the presence of the CL-L2-CH1-H-CH2-CH3_S-TM gene cassette and for loss of the FRT-flanked puromycin resistance gene. (FIGS. 13F and 13G. Note that the segments labeled F. and G. and connected by a dashed line in the figure are contiguous in the Igh locus in in vivo.) Correctly targeted mice are used to establish a colony of mice.

Example 4: Use of Homologous Recombination to Introduce a Mouse CL-L2-CH1_S-TM Gene Cassette into the Endogenous Mouse Igh Locus Upstream of Ighm for the Production of scVHAbs This example is identical in all aspects to Example 3 except that the genetically modified mice produce scVHAbs instead of HCAbs. This is accomplished by modifying the gene cassette (targeting vector) to have the structure CL-L2-CH1_S-TM instead of CL-L2-CH1-H-CH2-CH3_S-TM. The structure and sequence of the targeting vector is otherwise the same as in Example 3, as are the methods used to introduce the vector into ES cells, to select and analyze for correct homologous recombination, and to establish a colony of mice. (Note that the Linker 1-containing cassette, L1-CL-L2-CH1_S-TM, also described herein, can be introduced in an identical fashion.)

Example 5: Use of Recombinase Mediated Cassette Exchange (RMCE) to Introduce a Mouse CL-L2-CH1-H-CH2-CH3_S-TM Gene Cassette into the Endogenous Mouse Igh Locus Upstream of Ighm for the Production of HCAbs

Example 5A: Creation of the RMCE Acceptor Allele

The object here is to introduce a puro_TK fusion gene flanked upstream by a mutant FRT site and a mutant LoxP site and downstream by WT FRT and Lox P sites into a region of the endogenous Igh locus downstream of Ep and upstream of Ighm (FIG. 14B). In this configuration, the mutant and WT FRT or LoxP sites are unable to recombine in the presence of Flp or Cre recombinases but can integrate a piece of donor DNA that has the corresponding mutant and WT sites at its 5' and 3' ends, respectively (FIG. 14A). The puro_TK fusion gene is introduced by homologous recombination using the same SHA and LHA as in FIG. 13. An additional feature of the targeting vector is the presence of a diphtheria toxin A (DTA) gene (SEQ ID NO:34) at the 5' end, upstream of the SHA. This element is used for negative selection against cells that have integrated the targeting vector but not by homologous recombination; such cells retain the DTA gene and are killed when the toxin is expressed.

The targeting vector is introduced into the ES cells by electroporation, and cells are grown in media supplemented with puromycin. Surviving isolated ES cell clones are then monitored for successful gene targeting by genomic PCR using widely practiced gene targeting strategies with primers located within, 5' and 3' of the newly introduced puro_TK fusion gene cassette. The structure of the targeted locus is furtherer verified by genomic southern blots using a probe that maps to DNA sequence flanking the 5' side of the SHA, a second probe that maps to DNA sequence flanking the 3' side of the LHA and a third probe that maps within the novel DNA between the two arms of genomic identity in the vector. (The structure of the correctly targeted locus is depicted in FIG. 14C.

Karyotypes of PCR- and Southern blot-positive clones of ES cells are analyzed using an in situ fluorescence hybridization procedure designed to distinguish the most commonly arising chromosomal aberrations that arise in mouse ES cells. Clones with such aberrations are excluded from further use. ES cell clones that are judged to have the expected correct genomic structure based on the PCR and Southern blot data—and that also do not have detectable chromosomal aberrations based on the karyotype analysis—are selected for further use as described below.

Example 5B: Introduction of the CL-L2-CH1-H-CH2-CH3_S-TM Gene Cassette by Recombinase Mediated Cassette Exchange (RMCE)

The RMCE targeting vector (FIG. 15A) is identical in sequence to the homologous region shown in FIGS. 13A and 13B, except that the vector is flanked on the 5' end by mutant FRT and LoxP sites and on the 3' end by WT FRT and LoxP sites. (Note that the L1-CL-L2-CH1-H-CH2-CH3_S-TM cassette also described herein can be introduced in an identical fashion.)

The vector is introduced into the RMCE-modified ES cells (FIG. 15B) created in Example 5A together with a vector for transient expression of CRE or Flp recombinase and the targeting vector is integrated, resulting in the genomic structure illustrated in FIGS. 15C and 15D. (Note that the segments labeled C. and D. and connected by a dashed line in the figure are contiguous in the Igh locus in vivo.) ES cell that have not correctly integrated the targeting vector by RMCE retain the Puro_TK gene and are killed by adding ganciclovir to the growth media.

Surviving isolated ES cell clones are then monitored for successful gene targeting by genomic PCR using widely practiced gene targeting strategies with primers located within, 5' and 3' of the newly introduced CL-L2-CH1-H-CH2-CH3_S-TM gene cassette. The structure of the targeted locus is furtherer verified by genomic southern blots using a probe that map to DNA sequence flanking the 5' side, the 3' side, and within the novel DNA.

Karyotypes of PCR- and Southern blot-positive clones of ES cells are analyzed using an in situ fluorescence hybridization procedure designed to distinguish the most commonly arising chromosomal aberrations that arise in mouse ES cells. Clones with such aberrations are excluded from further use. ES cell clones that are judged to have the expected correct genomic structure based on the PCR and Southern blot data—and that also do not have detectable chromosomal aberrations based on the karyotype analysis—are selected for further use.

ES cell clones carrying the properly targeted CL-L2-CH1-H-CH2-CH3_S-TM gene cassette in the mouse heavy chain locus are microinjected into mouse blastocysts from strain DBA/2 to create partially ES cell-derived chimeric mice according to standard procedures. Male chimeric mice with the highest levels of ES cell-derived contribution to their coats are selected for mating to female mice. Offspring from these matings are analyzed for the presence of the CL-L2-CH1-H-CH2-CH3_S-TM gene cassette. Correctly targeted mice are used to establish a colony of mice.

Example 6: Use of Recombinase Mediated Cassette Exchange (RMCE) to Introduce a Mouse CL-L2-CH1_S-TM Gene Cassette into the Endogenous Mouse Igh Locus Upstream of Ighm for the Production of scVHAbs This example is identical in all aspects to Example 5 except that the genetically modified mice produce scVHAbs instead of HCAbs. This is accomplished by modifying the targeting vector to have the structure CL-L2-CH1_S-TM instead of CL-L2-CH1-H-CH2-CH3_S-TM. The structure and sequence of the targeting vector is otherwise the same as in Example 5, as are the methods used to introduce the vector into ES cells, to select and analyze for correct homologous recombination, and to establish a colony of mice. (Note that the L1-CL-L2-CH1_S-TM cassette also described herein can be introduced in an identical fashion.)

The invention claimed is:

1. A single chain heavy chain variable domain (VH) antibody (scVHAb) comprising an antigen-binding part consisting of a VH domain, and said scVHAb further comprising an immunoglobulin light chain constant domain (CL) and an immunoglobulin heavy chain constant domain 1 (CH1), in the order from N-terminus to C-terminus: VH-L1-CL-L2-CH1, wherein L1 is optional, wherein L1 and L2 are each, independently, peptidic linkers; and wherein L2 is a peptidic linker with a length of 25-50 amino acids having a sequence consisting of glycine and serine in any combination; and wherein CL is paired with CH1 through beta-sheet contact thereby obtaining a CL/CH1 dimer.

2. The scVHAb of claim 1, wherein the CL is either Cκ or Cλ.

3. The scVHAb of claim 2, wherein, the Cλ is selected from the group consisting of Cλ1, Cλ2 and Cλ3.

4. The scVHAb of claim 1, wherein L1 is an amino acid sequence of 3-40 amino acids length.

5. The scVHAb of claim 4, wherein L1 consists of:

a) a sequence of glycine and/or serine in any combination; or b) a VH framework sequence.

6. The scVHAb of claim 1, wherein the C-terminus of the antigen-binding part is fused to a hinge region and further immunoglobulin constant domains, which comprise, in the order from N-terminus to C-terminus, at least CH2-CH3, thereby forming an extended scVHAb comprising, from the N-terminus to the C-terminus, VH-L1-CL-L2-CH1-hinge-CH2-CH3.

7. A heavy chain antibody (HCAb) comprising two extended scVHAbs of claim 6, wherein the CH2-CH3 domains of a first extended scVHAb are paired with the CH2-CH3 domains of a second extended scVHAb, thereby forming an Fc region.

8. A repertoire of antibodies comprising the scVHAb of claim 1, wherein said repertoire is obtainable by cloning genes encoding the antibodies comprising the scVHAb of claim 1 from B cells or by secreting the antibodies by a variety of mammalian plasmacytes.

9. The repertoire of claim 8, wherein the plasmacytes are of rodent origin.

10. The repertoire of claim 9, wherein the plasmacytes are of mouse origin.

* * * * *